US012653868B2

(12) United States Patent (10) Patent No.: US 12,653,868 B2
Cruz et al. (45) Date of Patent: Jun. 16, 2026

(54) USES OF A2 DOMAIN OF VON WILLEBRAND FACTOR

(71) Applicant: BAYLOR COLLEGE OF MEDICINE, Houston, TX (US)

(72) Inventors: Miguel Angel Cruz, Pearland, TX (US); Trung Nguyen, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 1074 days.

(21) Appl. No.: 17/595,245

(22) PCT Filed: May 14, 2020

(86) PCT No.: PCT/US2020/032944
§ 371 (c)(1),
(2) Date: Nov. 12, 2021

(87) PCT Pub. No.: WO2020/232277
PCT Pub. Date: Nov. 19, 2020

(65) Prior Publication Data
US 2022/0193204 A1     Jun. 23, 2022

Related U.S. Application Data

(60) Provisional application No. 62/847,454, filed on May 14, 2019.

(51) Int. Cl.
| | |
|---|---|
| *A61K 38/36* | (2006.01) |
| *A61K 31/155* | (2006.01) |
| *A61K 31/19* | (2006.01) |
| *A61K 31/401* | (2006.01) |
| *A61K 31/436* | (2006.01) |
| *A61K 31/5025* | (2006.01) |
| *A61K 31/519* | (2006.01) |
| *A61K 31/553* | (2006.01) |
| *A61K 31/704* | (2006.01) |
| *A61K 31/7052* | (2006.01) |
| *A61K 31/7056* | (2006.01) |
| *A61P 7/02* | (2006.01) |

(52) U.S. Cl.
CPC ............ *A61K 38/36* (2013.01); *A61K 31/155* (2013.01); *A61K 31/19* (2013.01); *A61K 31/401* (2013.01); *A61K 31/436* (2013.01); *A61K 31/5025* (2013.01); *A61K 31/519* (2013.01); *A61K 31/553* (2013.01); *A61K 31/704* (2013.01); *A61K 31/7052* (2013.01); *A61K 31/7056* (2013.01); *A61P 7/02* (2018.01)

(58) Field of Classification Search
CPC ...... A61K 38/36; A61K 31/155; A61K 31/19;
A61K 31/401; A61K 31/436; A61K
31/5025; A61K 31/519; A61K 31/553;
A61K 31/704; A61K 31/7052; A61K
31/7056; A61P 7/02
See application file for complete search history.

(56) References Cited

U.S. PATENT DOCUMENTS

| | | |
|---|---|---|
| 2009/0118161 A1 | 5/2009 | Cruz |
| 2016/0263148 A1 | 9/2016 | Pun et al. |

FOREIGN PATENT DOCUMENTS

| | | |
|---|---|---|
| WO | 2005004793 A2 | 1/2005 |

OTHER PUBLICATIONS

Hu et al., "Characteristics of SARS-CoV-2 and COVID-19," Nature Rev Microbiol. 19:141-154 (2021) (Year: 2021).*
Yu et al, "Surface vimentin is critical for the cell entry of SARS-CoV," J Biomed Sci 23:14 (2016) (Year: 2016).*
Grobler et al, "Covid-19: The Rollercoaster of Fibrin(Ogen), D-Dimer, Von Willebrand Factor, P-Selectin and Their Interactions with Endothelial Cells, Platelets and Erythrocytes," Int'l J Mol Sci 21:5168 (2020) (Year: 2020).*
Drumm et al, Genetic Variation and Clinical Heterogeneity in Cystic Fibrosis, Annu. Rev. Pathol. Mech. Dis., 2012, 7, pp. 267-282 (Year: 2012).*
Yampolsky et al, The Exchangeability of Amino Acids in Proteins, Genetics, 2005, 170, pp. 1459-1472. (Year: 2005).*
Nguyen et al., entitled "A recombinant fragment of von Willebrand factor reduces fibrin-rich microthrombi formation in mice with endotoxemia", Thromb Res., May 2015, vol. 135, No. 5, pp. 1025-1030.

(Continued)

*Primary Examiner* — Julie Ha
*Assistant Examiner* — Kristina M Hellman
(74) *Attorney, Agent, or Firm* — Norton Rose Fulbright US LLP

(57) ABSTRACT

Embodiments of the disclosure encompass methods and compositions for maintaining a healthy fibrin network in an individual. The disclosure includes methods of targeting fibrin in an individual for the purpose of restoring fibrin that is subject to a level of fibrinolysis that is deleterious, such as excessive or reduced with respect to the general population. Such modifications of fibrin in an individual may include direct targeting of fibrin with the A2 domain of von Willebrand factor or a functional derivative or fragment thereof. In specific embodiments, the methods restore to a normal level any imbalance between coagulation and inflammation.

19 Claims, 51 Drawing Sheets

Specification includes a Sequence Listing.

(56) References Cited

OTHER PUBLICATIONS

Nguyen T. et al: "Abstract PD-017 : Rrecombinant Von Willebrand Factor A2 Polypetide Attenuates Organ Injuries in a Pordine Model of Methicillin-Resistant *Staphylococcus aureus* (MRSA) Sepsis-Induced Disseminated Intravascular Coagulations (Dic)", Pediatric Critical Care Medicine, vol. 19, Jun. 1, 2018 (Jun. 1, 2018), pp. 34-35.

Fasipe et al. "Extracellular Vimentin/VWF (von Willebrand Factor) Interaction Contributes to VWF String Formation and Stroke Pathology", Stroke. 2018;49:2536-2540, American Heart Association.

Weinberg, J. Brice et al: "Extravascular fibrin formation and dissolution in synovial tissue of patients with osteoarthritis and rheumatoid arthritis", Arthritis & Rheumatism, vol. 34, No. 8, Aug. 1, 1991 (Aug. 1, 1991), pp. 996-1005.

Kwasny-Krochin et al: "Unfavorably altered fibrin clot properties in patients with active rheumatoid arthritis", Thrombosis Research, Elsevier, Amsterdam, NL, vol. 126, No. 1, Jul. 1, 2010 (Jul. 1, 2010), pp. e11-e16.

* cited by examiner

Vehicle Control                    WT A2

Peptide containing
the E1567 residue

Peptide containing the E1567 residue

USES OF A2 DOMAIN OF VON WILLEBRAND FACTOR

CROSS-REFERENCE TO RELATED APPLICATIONS

This application is a national phase under 35 U.S.C. § 371 of International Application No. PCT/US2020/032944, filed May 14, 2020, which claims priority to U.S. Provisional Patent Application Ser. No. 62/847,454, filed May 14, 2019, the entire contents of each of which are incorporated herein by reference in their entirety.

STATEMENT REGARDING FEDERALLY SPONSORED RESEARCH OR DEVELOPMENT

This invention was made with government support under HL72886 and GM112806 awarded by National Institutes of Health (NIH). The government has certain rights in the invention.

TECHNICAL FIELD

Embodiments of the disclosure concern at least the fields of cell biology, molecular biology, biochemistry, and medicine.

BACKGROUND

Persistent inflammation during sepsis activates the coagulation and thrombotic pathways leading to a prothrombotic and antifibrinolytic state. The resultant widespread fibrin deposition in small to mid-size blood vessels leads to organ ischemia and dysfunction 1. The presence of widespread fibrin deposition is a hallmark of disseminated intravascular coagulation (DIC) that can occur in 29-50% of septic patients and is associated with an increased mortality[2-4]. DIC is widely accepted as one of the pathophysiologic mechanisms for the development of multiple organ dysfunction syndrome (MODS) during sepsis as a result of a "dysregulated host response to infection"[5]. Although the treatment for sepsis includes source-control, antibiotics, and hemodynamic resuscitation, no therapy currently exists for sepsis-induced DIC other than supportive care.

Fibrinogen plays an essential role in hemostasis and thrombosis. During coagulation, thrombin converts fibrinogen to fibrin forming the insoluble end-product of the coagulation pathway (reviewed in[6]). A number of conditions, including coagulation factors, plasma components, blood cells, and blood flow contribute to the formation, structure and stability of the resultant fibrin clot (reviewed in[7]). It is well appreciated that alterations in the fibrin clot profile is directly associated with different clinical pathologies, such as thinner or thicker fibers being associated with bleeding or thrombosis, respectively[8-12]. Therefore, the development of medical interventions to modify the fibrin clot structure and stability to prevent pathologic hemorrhage and thrombosis in systemic inflammation is an unmet medical need.

In an endotoxemic murine model, a recombinant A2 domain of human von Willebrand factor (VWF), the A2 protein, decreased mortality from 60 to 0%, and attenuated disseminated microvascular thromboses[13]. The present disclosure characterizes fibrin modulation and provides a solution to a long felt need in the art related to medical conditions associated with fibrin dysregulation, such as stroke and thrombosis.

Further, the A2 protein can modulate interaction between viral particles and cell surface receptors. In 2019, the Centers for Disease Control and Prevention (CDC) started monitoring the outbreak of a new coronavirus, SARS-CoV-2, which causes COVID-19. SARS-CoV-2, can lead to severe acute respiratory syndrome and life-threatening forms of pneumonia. Authorities first identified the virus in Wuhan, China. Since then, the virus has spread to nearly every country, leading the World Health Organization (WHO) to declare this as a pandemic. As of Apr. 22, 2020, over 2.5 million people have contracted the virus worldwide, and it has caused over 170,000 deaths. In the United States alone, the virus has affected over 800,000 people, resulting in more than 45,000 deaths.

SARS-CoV-2 infects cells using the spike protein (S), with current reports suggesting angiotensin-converting enzyme 2 (ACE2) and vimentin on the host cell as the points of contact (1, 2). SARS-CoV-2 S shares ~76% homology with SARS-CoV S, the spike protein on the coronavirus causing severe acute respiratory syndrome (SARS; SARS-CoV) (3). SARS-CoV S requires binding to both ACE2 and cell surface vimentin to enter cells (4), suggesting that SARS-CoV-2 may also interact with cell surface vimentin to bind to and infect cells.

Thus, the present disclosure characterizes the association of the A2 protein with cell surface receptors, for example vimentin, and provides a solution to the need for treatment of certain medical conditions, including at least coronavirus infections such as SARS-CoV-2 which can lead to life-threatening complications, for example.

BRIEF SUMMARY

The present disclosure is directed to methods and compositions for preserving or maintaining a fibrin network in an individual with a medical condition associated fibrin or dysregulation thereof. The methods and compositions concern targeting of fibrin by the A2 protein or functional fragments or derivatives thereof for the purpose of maintaining the fibrin network or reversing impairment of the fibrin network. The targeting of fibrin by A2 protein or functional fragments or derivatives thereof attenuates or lessens the severity of medical conditions in which fibrinolysis, for example, is directly or indirectly associated with the medical condition. The methods of the disclosure improve or reverse dysregulated coagulation and disseminated fibrin deposition, in specific embodiments.

The present disclosure elucidates the mechanism by which the A2 protein improves survival and attenuates DIC, for example. In addition, it was determined whether the administration of the A2 protein to septic animals (12 and 24 hours post-bacteremia) could attenuate microvascular thrombosis and organ injuries in a pre-clinical porcine model of human pathogenic methicillin-resistant *Staphylococcus aureus* (MRSA) sepsis-induced DIC without increasing bleeding. The A2 protein modifies the fibrin structure, thereby modulating clot degradation. In addition, infusion of the A2 protein diminished formation of microvascular thromboses, organ injury, and D-dimer levels without increasing bleeding in MRSA-associated septic pigs.

Embodiments of methods encompass targeting fibrin to maintain or repair a fibrin network in an individual, comprising the step of delivering to the individual an effective amount of the A2 domain of von Willebrand factor or a functional derivative or fragment thereof. The method may be further defined as modifying the structure of fibrin in the individual. The method may be further defined as increasing the rate of fibrin polymerization in the individual. In specific embodiments, the A2 domain or a functional derivative or fragment thereof interacts directly with the fibrin. The method reduces the consumption of one or more coagulation factors in the individual, in specific cases. The individual may or may not have excessive fibrinolysis compared to a standard or control population. In some cases, the individual has dysregulated activated coagulation or is at risk for having dysregulated activated coagulation. In some cases, the individual has thrombosis or is at risk for having thrombosis and/or the individual may have sepsis or is at risk for having sepsis. In specific cases, the sepsis induces disseminated intravascular coagulation (DIC). The sepsis may be caused by bacterial, viral or fungal infection in the individual. In specific embodiments, the sepsis is induced by methicillin resistant *Staphylococcus aureus* (MRSA). The individual may or may not exhibits at least one symptom of sepsis, such as fever, systemic inflammation, tachycardia, or a combination thereof. In specific embodiments, the individual has disseminated intravascular coagulation. The individual may be pregnant and or may have one of more of the following: cancer, has traumatic brain injury, trauma induced coagulopathy, hypoxic-ischemic brain injury, stroke, myocardial infarction, sepsis-induced multiple organ dysfunction syndrome, inflammatory bowel disease, antiphospholipid syndrome, rheumatoid arthritis, chronic obstructive pulmonary disease, diabetes mellitus, end stage renal disease, malignancy, liver cirrhosis, deep vein thrombosis, pulmonary embolism, reperfusion injury, liver ischemic reperfusion, kidney ischemic reperfusion, microvascular thrombosis and/or organ injuries in systemic inflammation. The individual may be a healthy individual or asymptomatic.

Furthermore, coronavirus binding of cell surface receptors plays a central role in viral infection, leading to morbidity and mortality, and embodiments of the disclosure concern methods and compositions for prevention or treatment thereof. Coronavirus infection can lead to medical conditions including severe acute respiratory syndrome (SARS) or respiratory infections, which can in turn lead to pneumonia, organ failure, respiratory failure, blood clots, heart conditions such as cardiomyopathies, acute kidney injury, and further viral and bacterial infections. Embodiments of the disclosure concern methods and compositions for treating coronavirus infections, including those associated with any medical condition. Particular embodiments of the disclosure utilize the A2 domain of von Willebrand factor or functionally active fragments or derivatives thereof for treating coronavirus infections or any medical condition in which the blocking of viral particles from binding cell surface receptors is beneficial. In specific embodiments, the medical condition is treated, or at least one symptom is improved upon, following blockage of coronavirus binding to cell surface receptors.

In specific embodiments, the A2 domain of von Willebrand factor or functionally active fragments or derivatives thereof results in an improvement of at least one symptom of a medical condition in which coronavirus infection is involved. In particular embodiments, the medical condition is SARS or a respiratory infection. In particular embodiments, SARS or the respiratory infection can lead to life-threatening complications including but not limited to pneumonia, organ failure, blood clots, respiratory failure, heart conditions such as cardiomyopathies, acute kidney injury, or further viral and bacterial infections, for example.

In one embodiment, there is a method of treating or preventing coronavirus infection in an individual, comprising the step of delivering to the individual a therapeutically effective amount of the A2 domain or a functionally active fragment and/or functionally active derivative or variant thereof. In another embodiment, there is a composition for treating or preventing coronavirus infection in an individual comprising a therapeutically effective amount of the A2 domain or a functionally active fragment and/or functionally active derivative or variant thereof. In some embodiments, the coronavirus is SARS-CoV-2. The coronavirus infection may further comprise SARS or a respiratory infection, and SARS or respiratory infection may comprise pneumonia, organ failure, blood clots, respiratory failure, heart conditions such as cardiomyopathies, acute kidney injury, further viral and bacterial infections, or a combination thereof. The individual may have dysregulated activated coagulation or may be at risk for having dysregulated activated coagulation.

In specific embodiments, blocking the interaction between any protein or part of SARS-CoV-2 (including the S protein) with vimentin is useful for preventing or attenuating SARS-CoV-2 infection in an individual. In certain embodiments, the A2 domain prevents interaction between SARS-CoV-2 and vimentin to prevent uptake or infection by the virus. In some embodiments, the A2 domain prevents interaction between SARS-CoV-2 and rod domain of vimentin (rhRod) to prevent update or infection by the virus. In specific aspects, the A2 domain or a functionally active fragment or derivative thereof binds SARS-CoV S-ACE2, and in particular cases the A2 domain interferes with host-virus interactions to result in a therapeutic or preventative effect. In particular cases, the A2 domain prevents interaction between SARS-CoV-2 and vimentin and/or rhRod and prevents or reduces infection of SARS-CoV-2 in an individual. In at least some cases, the A2 domain blocks binding of the SARS-CoV-2 spike protein by vimentin and/or rhRod.

An individual may be provided a second therapy for the medical condition being treated with the A2 domain. The second therapy may comprise antibiotics, antivirals, convalescent serum, immune modulators, anticoagulants, fluids, oxygen, a corticosteroid, antibodies, GSnP-6, sialyl Lewis X analog, anti-proliferatives, calcineurin inhibitors, anti-signaling compounds, or a combination thereof.

Any method of the disclosure may further comprise testing for (including resulting in a diagnosis of) a medical condition associated with coronavirus infection or testing for presence of the virus. Any individual may or may not be symptomatic and/or may or may not have been exposed to a coronavirus-infected individual. When an individual is symptomatic, they may or may not have one or more of fever, cough, shortness of breath or difficulty breathing, tiredness, aches, chills, sore throat, loss of smell, loss of taste headache, diarrhea, and vomiting. The individual may or may not have pneumonia or acute respiratory distress syndrome (ARDS).

In specific embodiments, the A2 domain or a functionally active fragment or derivative thereof is delivered to the individual intravenously, intradermally, transdermally, intrathecally, intraarterially, intraperitoneally, intranasally, intravaginally, intrarectally, topically, intramuscularly, subcutaneously, mucosally, orally, topically, locally, by inhalation, by injection, by infusion, via catheter, and/or via lavage, and the A2 domain or a functionally active fragment or derivative thereof may be delivered to the individual once a day, more than once a day, more than once a week, more than once a month, or more than once a year. The A2 domain or a functionally active fragment or derivative thereof may be delivered to the individual once or multiple times, and in any case the A2 domain or a functionally active fragment or derivative thereof may be provided to an individual by constant infusion. Compositions of the disclosure may further include a pharmaceutically acceptable carrier.

In a further embodiment, there is a kit for treating or preventing coronavirus infection in an individual, comprising a composition comprising the A2 domain or functionally active fragments or variants thereof disclosed herein and a second therapy for coronavirus infection or prevention, said composition and second therapy housed in one or more suitable containers. The composition can further comprise a pharmaceutically acceptable carrier.

In particular embodiments, the A2 domain comprises sequence selected from the group consisting of SEQ ID NO:1, SEQ ID NO:2, SEQ ID NO:3, SEQ ID NO:16, SEQ ID NO:17, SEQ ID NO:18, SEQ ID NO:19, and SEQ ID NO:20. The A2 domain may comprise a functional fragment comprising at least at least 90%, 91%, 92%, 93%, 94%, 95%, 96%, 97%, 98%, or 99% identity to SEQ ID NO:1, SEQ ID NO:2, SEQ ID NO:3, SEQ ID NO:16, SEQ ID NO:17, SEQ ID NO:18, SEQ ID NO:19, or SEQ ID NO:20. The A2 domain may have 1, 2, 3, 4, or 5 amino acid differences with respect to SEQ ID NO:1, SEQ ID NO:2, SEQ ID NO:3, SEQ ID NO:16, SEQ ID NO:17, SEQ ID NO:18, SEQ ID NO:19, or SEQ ID NO:20.

It is specifically contemplated that any limitation discussed with respect to one embodiment of the disclosure may apply to any other embodiment of the disclosure. Furthermore, any composition of the disclosure may be used in any method of the disclosure, and any method of the disclosure may be used to produce or to utilize any composition of the disclosure. Aspects of an embodiment set forth in the Examples are also embodiments that may be implemented in the context of embodiments discussed elsewhere in a different Example or elsewhere in the application, such as in the Brief Summary, Detailed Description, Claims, and Brief Description of the Drawings.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The novel features of the methods and compositions of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings (also "Figure" and "FIG." herein), of which:

FIG. 1A, crystal structure of the A2 domain. The amino acid residue E1567 analyzed in this study is also depicted and as a point of reference, it also shows the location of the ADAMTS-13 cleavage site. FIG. 1B, increasing concentrations of either WT A2 protein or A2 mutant were incubated with immobilized thrombin-generated fibrin in microtiter wells. The A2 mutant had a significant lower binding activity for fibrin (half-maximal binding of $1.03\pm0.079$ μM) than that of WT A2 protein (half-maximal binding of $0.06\pm0.004$ μM). Each point in the graph represents the mean±SEM of three determinations, $*p<0.05$. Similarly, the binding of the two A2 variants to FIG. 1C—A1 domain of VWF, and FIG. 1D—vimentin are shown. The A2 mutant had a binding activity for both ligands comparable to that of WT A2 protein. FIG. 1E, the use of monoclonal antibody and FIG. 1F, CD thermal unfolding show that the overall structure of the A2 protein was not altered by the mutation E1567A. FIG. 1F also shows the assessment of two different batches of WT A2 protein.

FIGS. 2A-2D. The A2 protein alters and incorporates into the fibrin clot structure. FIG. 2A, confocal microscopy images of fibrin clots at magnification of 200× formed in plasma from healthy human donor. Note that the effect of the A2 protein on the resultant clot structure (right panel) is evident as compared to plasma incubated with vehicle control (left panel). FIG. 2B, the WT A2 protein clearly altered the resultant fibrin structure as compared to plasma treated with vehicle control and A2 mutant. FIG. 2C, representative of 3D confocal microscopy images of fibrin clots formed in whole blood from a healthy human donor mixed with either vehicle control or WT A2 protein (0.5 μM) conjugated to fluorescent antibodies in the 488 spectral range (e.g., ALEXA FLUOR®488). Fibrin was visualized by supplementing whole blood with 1% of human fibrinogen conjugated to fluorescent antibodies in the 647 spectral range (e.g., ALEXA FLUOR® 647). In comparison to the treatment of vehicle control, the A2 protein clearly modified the resultant fibrin structure. In addition, the A2 protein did not interact with the blood cells present in the mixture as compared to vehicle control containing dye only. FIG. 2D, a higher (300×) magnification demonstrates the incorporation of the A2 protein (right panel) into the fibrin structure (left panel).

FIG. 3A, bar graph shows the significant effect of the A2 protein on delaying fibrin lysis using a thromboelastometry system (e.g., ROTEM®). Represents three experiments from using whole blood of two healthy human donors. FIG. 3B, fibrin was formed from fibrinogen supplemented with plasminogen, tPA, and vehicle control or WT A2 protein or A2 mutant (4.0 μM) and turbidity was measured at λ 405 nm. The tracings shown are representative of 4 experiments. FIG. 3C, Coomasie Blue stain of a protein gel showing the differential effect of the WT A2 protein on the resultant fibrin degradation products (FDPs) analyzed under non-reduced conditions. Gel shows the intermediate FDP fragments Y, D, and E. FIG. 3D, densitometry data analysis of FDPs assessed as in FIG. 3C from three separated experiments. FIG. 3E, immunoblot as in FIG. 3C using a polyclonal anti-human fibrinogen confirmed the increase of fragment Y in the present of WT A2 protein. FIG. 3F, the same bands as in FIG. 3E were probed with a monoclonal anti-high molecular weight FDP antibody. In comparison to conditions containing vehicle control or A2 mutant, the antibody had a poor reactivity with the fragment Y derived from the condition with WT A2 protein (representative of three separate experiments).

FIGS. 4A-4D The A2 protein exerts its beneficial effect via fibrin in vivo. FIG. 4A, survival curve depicting the effect of A2 mutant (n=12) in LPS-treated mice as compared to LPS-treated mice with either WT A2 protein (n=10) or saline (n=6). Difference is statistically significant (p<0.05). FIG. 4B, kidneys were harvested at 24 hours after the administration of LPS to mice and stained for fibrin. Dark staining depicts the fibrin deposition (arrow) and randomized areas were selected for analysis using ImageJ. FIG. 4C, in comparison to mice treated with the WT A2 protein, an increase fibrin deposition was notable for mice that received saline or the A2 mutant. FIG. 4D, notably, the fluorescence intensity of the fibrin clot formed in plasma from an endotoxemic mouse treated with A2 protein (right panel) was higher than that without the treatment (left panel). Representative of three experiments using three different mice per group.

FIGS. 5A-5B The A2 protein does not disrupt primary hemostasis. FIG. 5A, thrombosis kinetics were assessed by a light-dye injury model using intravital microscopy. Vessel occlusion was recorded in minutes. Data shown as mean±SE, n=8 per group. FIG. 5B, representative of 3 different citrated healthy whole blood containing 8% fluorescently labeled human fibrinogen and vehicle control or A2 protein (4.0 μM). The blood was perfused over a surface coated with collagen Type III (50 μg/ml) at high shear stress (60 dyn/cm$^2$). Buildup of the fluorescently-labeled fibrin and platelets was recorded during the 10-min perfusion.

FIGS. 6A-6E. The A2 protein was beneficial in septic pigs. FIG. 6A, there was established a clinically relevant 70 h-porcine model of MRSA-sepsis-induced DIC model. FIG. 6B, gross examination of kidneys demonstrating that the intervention with A2 protein 24 h after bacterial inoculation reduced organ damage in a dose dependent manner. FIG. 6C, similarly, the A2 protein was beneficial in reducing organ damage in liver. FIG. 6D, immunostaining for fibrin deposition (dark staining) in kidney glomeruli from septic pigs treated with saline (left) or A2 protein (3.5 mg/kg)(right). FIG. 6E, H&E staining showing bleeding in liver tissue from septic pig treated with saline (left) or A2 protein (3.5 mg/kg)(right).

FIG. 7A, D-dimer levels at 70 h after MRSA inoculation were significantly reduced in pigs intervened with the A2 protein (4 males, 2 females) as compared to septic pigs that only received saline (6 males, 2 females). FIG. 7B, notably, the fluorescence intensity of the fibrin clot formed in plasma from a septic pig treated with A2 protein (right panel) was higher than that without the treatment (middle panel) but comparable to the clot formed in plasma from a healthy pig (left panel). Representative of three experiments using three different pigs per group.

FIG. 10A. As described for FIG. 2, additional confocal microscopy images of fibrin clots at magnification of 200× formed in plasma from healthy human donors. The A2 protein affected the resultant clot structure (two right panels) in a dose dependent manner. FIG. 10B. Similar to FIG. 10A but using plasma from two septic patients at different days in the intensive care unit (magnification of 200×). The A2 protein (right column) was also effective in changing the fibrin clot structure as compared to the corresponding plasma mixed with vehicle control (left column).

FIG. 15A. Crystal structure of the A2 domain. The amino acid residue E1567 analyzed in this study is depicted as a point of reference; also shown is an ADAMTS-13 cleavage site. FIG. 15B. Increasing concentrations of either the WT A2 protein or A2 mutant were incubated with immobilized thrombin-generated fibrin in microtiter wells. The A2 mutant had significantly lower binding activity for fibrin (half-maximal binding, 1.03±0.079 μM) than the WT A2 protein (half-maximal binding, 0.06±0.004 μM). Each point in the graph represents the mean f standard error of the mean of 3 determinations. Use of monoclonal antibody (FIG. 15C) and circular dichroism thermal unfolding (FIG. 15D) shows that the overall structure of the A2 protein was not altered by the mutation E1567A. FIG. 15D. Assessment of 2 different batches of the WT A2 protein. *P<0.05. Abs, absorbance; n.s., not significant.

FIG. 16A. Fibrin was formed from using 10% healthy human plasma and vehicle control or the A2 protein (0-0.5 μM), and turbidity was measured at λ 405 nm. The tracings shown are the average of 4 separate experiments. The baseline for fibrin polymerization in different experimental groups is normalized to time 0. FIG. 16B. Bar graph shows the significant effect of the A2 protein in reducing the time to peak maximal absorbance in panel A. This represents 4 experiments using plasma from 2 healthy human donors (n=4 paired participants).P<0.05 vs control (no A2), *P<0.007 vs control. OD, optical density.

FIG. 17A. Confocal microscopy images of fibrin clots at a magnification of ×200 formed in plasma from healthy human donors. Note that the effect of the A2 protein (0.25 μM) on the resultant clot structure (right) is evident as compared with plasma incubated with vehicle control (left). Scale bars, 10 μM. FIG. 17B. The WT A2 protein clearly altered the resultant fibrin structure as compared with plasma treated with vehicle control and the A2 mutant. Scale bars, 50 μM.

FIG. 18A. Representative of 3-dimensional confocal microscopy images of fibrin clots formed in whole blood from a healthy human donor mixed with either vehicle control or the A2 protein (0.5 μM) conjugated to fluorescent antibodies in the 488 spectral range (e.g., ALEXA FLUOR® 488). Fibrin was visualized by supplementing whole blood with 1% human fibrinogen conjugated to fluorescent antibodies in the 647 spectral range (e.g., ALEXA FLUOR® 647). In comparison with the treatment of vehicle control, the A2 protein clearly modified the resultant fibrin structure. In addition, the A2 protein did not interact with the blood cells present in the mixture as compared with vehicle control containing dye only. Colocalization of fibrin and the A2 protein is identified by arrows in the right panel. Scale bars, 10 μM. FIG. 18B. A higher (300×) magnification demonstrates the incorporation of the A2 protein (top middle panel) into the fibrin structure (top left panel). The arrowheads point to the A2 protein bound to fibrin branching. In contrast, the A2 mutant did not increment the size of pores (bottom left panel) or formed clusters in fibrin branching (bottom middle panel). Colocalization of fibrin and the A2 protein is viewed at 300× magnification (top right) as overlapping the fibrin fibers. In contrast, there is less colocalization or overlapping of the A2 mutant with the fibrin fibers (bottom right). Scale bars, 10 μM.

FIG. 19A. Survival curve depicting the effect of the A2 mutant (n=12) in LPS-treated mice as compared with LPS-treated mice with either the WT A2 protein (n=10) or saline (n=6). The difference is statistically significant (P<0.05). FIG. 19B. Kidneys were harvested at 24 hours after the administration of LPS to mice and stained for fibrin. Dark staining depicts the fibrin deposition (arrows), and randomized areas were selected for analysis using ImageJ. FIG. 19C. In comparison with mice treated with the WT A2 protein, an increased fibrin deposition was notable for mice that received saline or the A2 mutant (n=10 per group, unpaired subjects). The difference between the WT A2 and control or the A2 mutant protein was significant. A.U., arbitrary unit.

FIGS. 20A and 20B. Confocal images of the fibrin structure in endotoxemic plasma collected at 2 hours after the injection of the A2 variants or vehicle control were analyzed using ImageJ. FIG. 20A. Notably, larger pores were observed in the resultant fibrin clot in plasma from mice treated with the WT A2 protein (right) in comparison with mice treated with vehicle control or the A2 mutant (left or middle, respectively; n=3 unpaired subjects). Representative of 3 experiments using 3 different mice per group. Scale bars, 10 μM. FIG. 20C. Plasma samples from LPS-treated mice were obtained at 2 hours after IP injection of A2 protein (4.0 mg/kg) or saline. Fibrin polymerization was measured by turbidity at 405 nm.

Turbidity curves represent the average of 6 separate experiments for each condition tested: with A2 protein or saline. *P=0.036 vs control or mutant, ***P<0.0001. NS, not significant.

Figure 21:
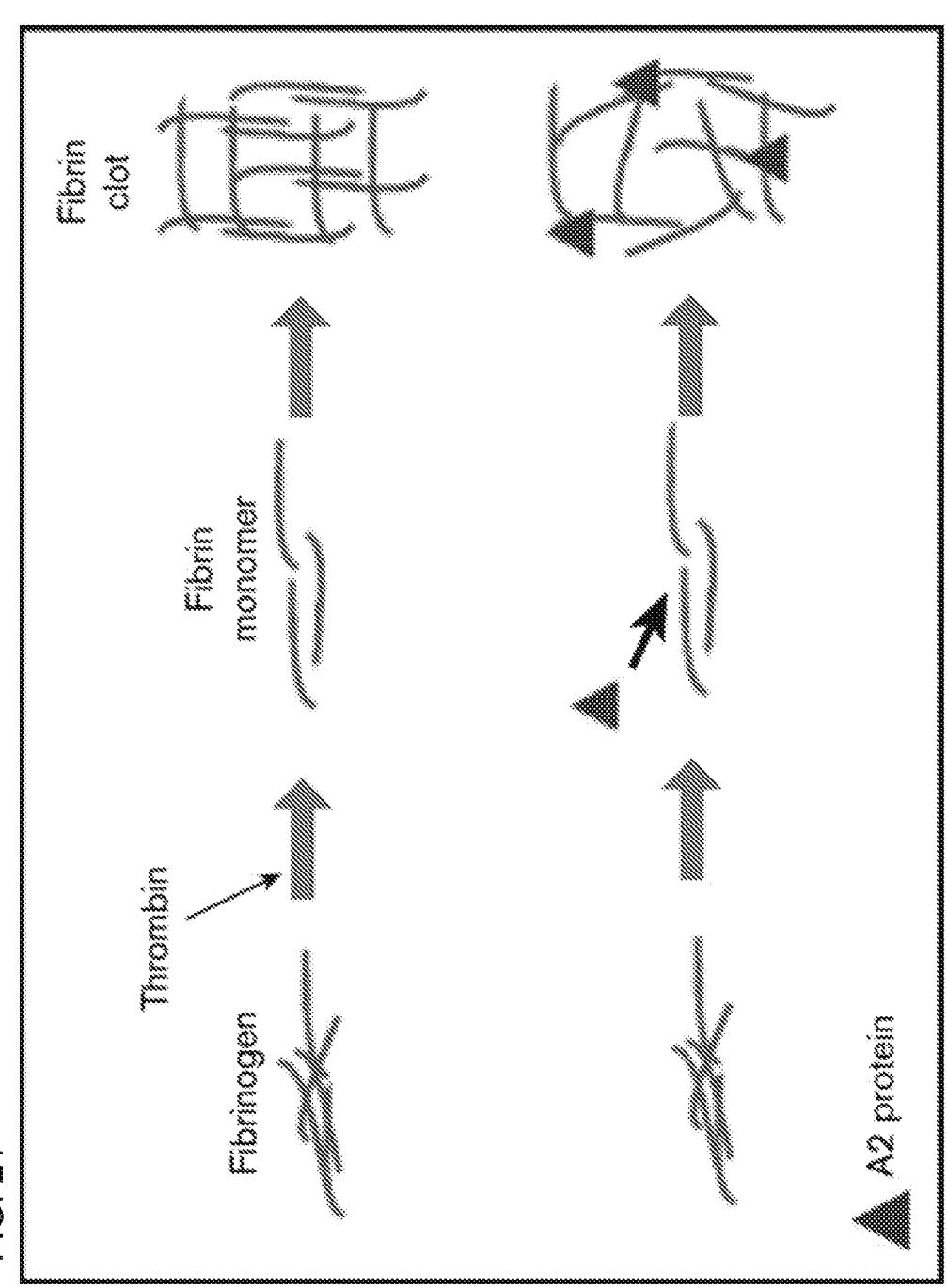

FIG. 21. Illustration of targeting fibrin formation directly as a novel approach to reduce microvascular thrombosis in systemic inflammation.

Figure 22:
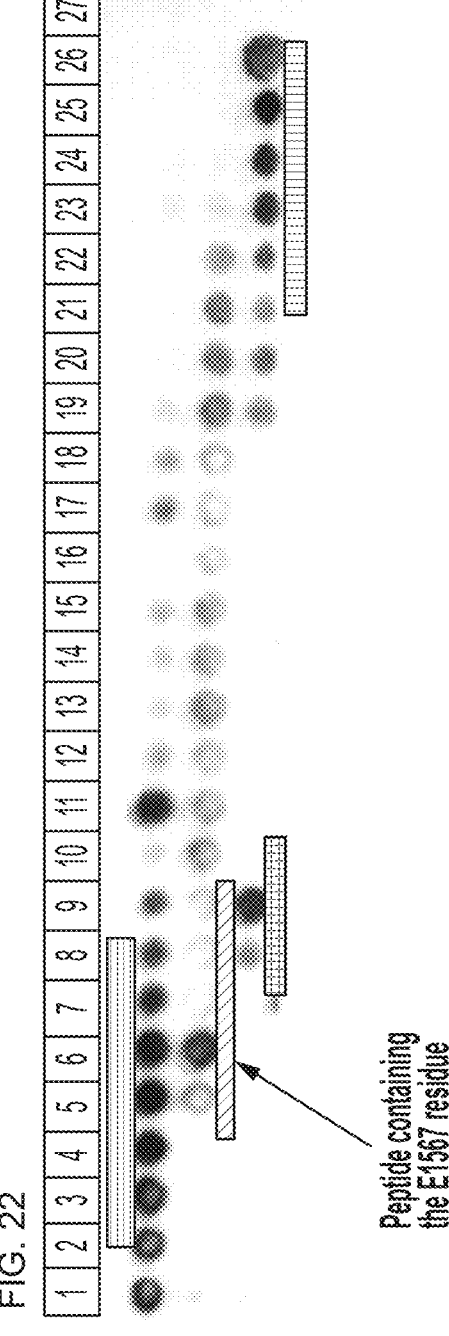

FIG. 22. Interaction of fibrin with the A2 protein using peptide spot array. The biotinylated fibrin bound to cellulose-bound peptide array was detected with avidin-HRP. The spots were analyzed using densitometry. The high intensity spots are marked with textured bars representing putative binding sites for fibrin.

Figure 23:
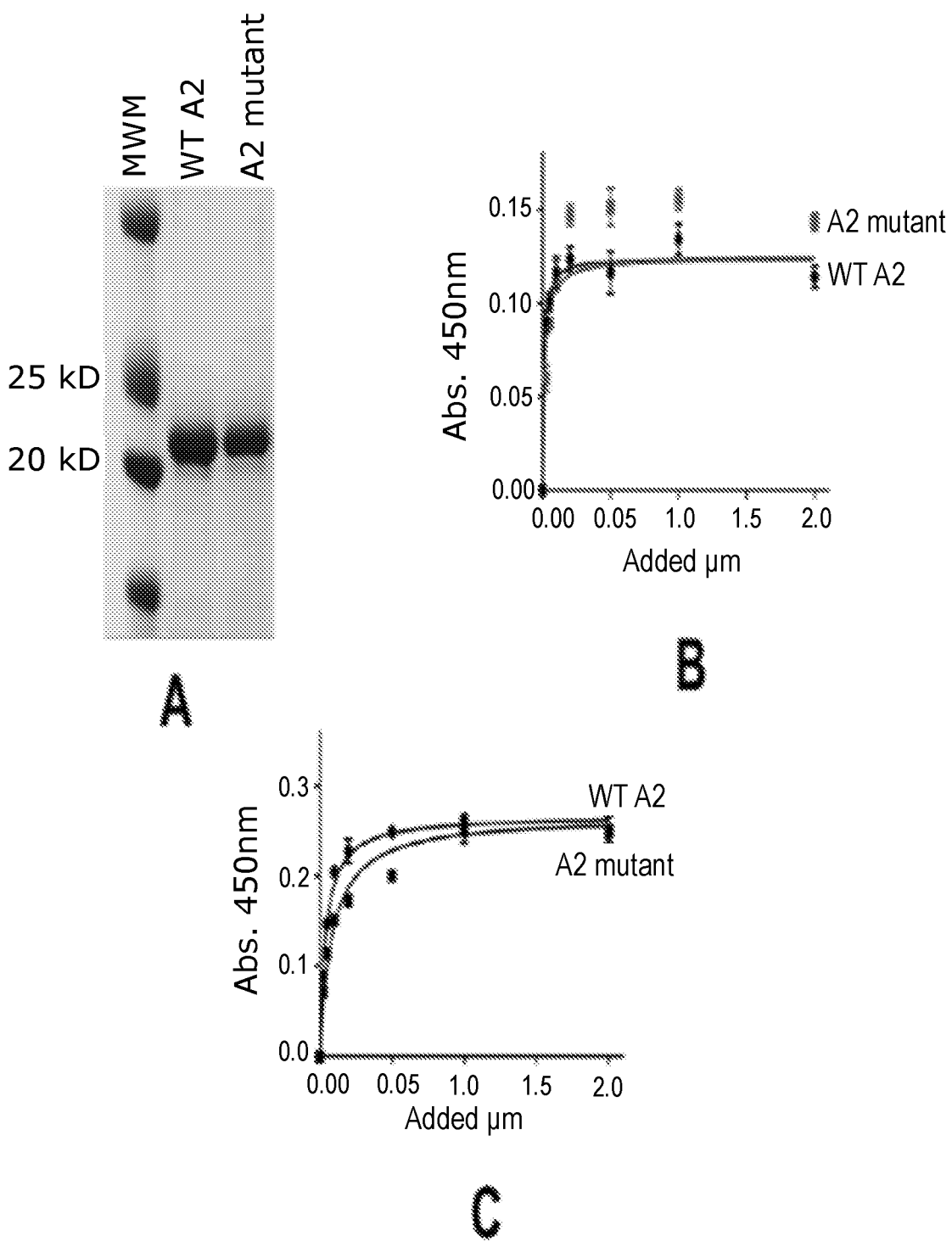

FIGS. 23A-23C. FIG. 23A. Coomasie Blue stained SDS-PAGE showing the purified WT A2 protein and A2 (E1567A) mutant under reduced conditions. The binding of the two A2 variants to (FIG. 23B) A1 domain of VWF, and (FIG. 23C) vimentin are shown. The A2 mutant had a binding activity for both ligands comparable to that of WT A2 protein.

Figure 16:
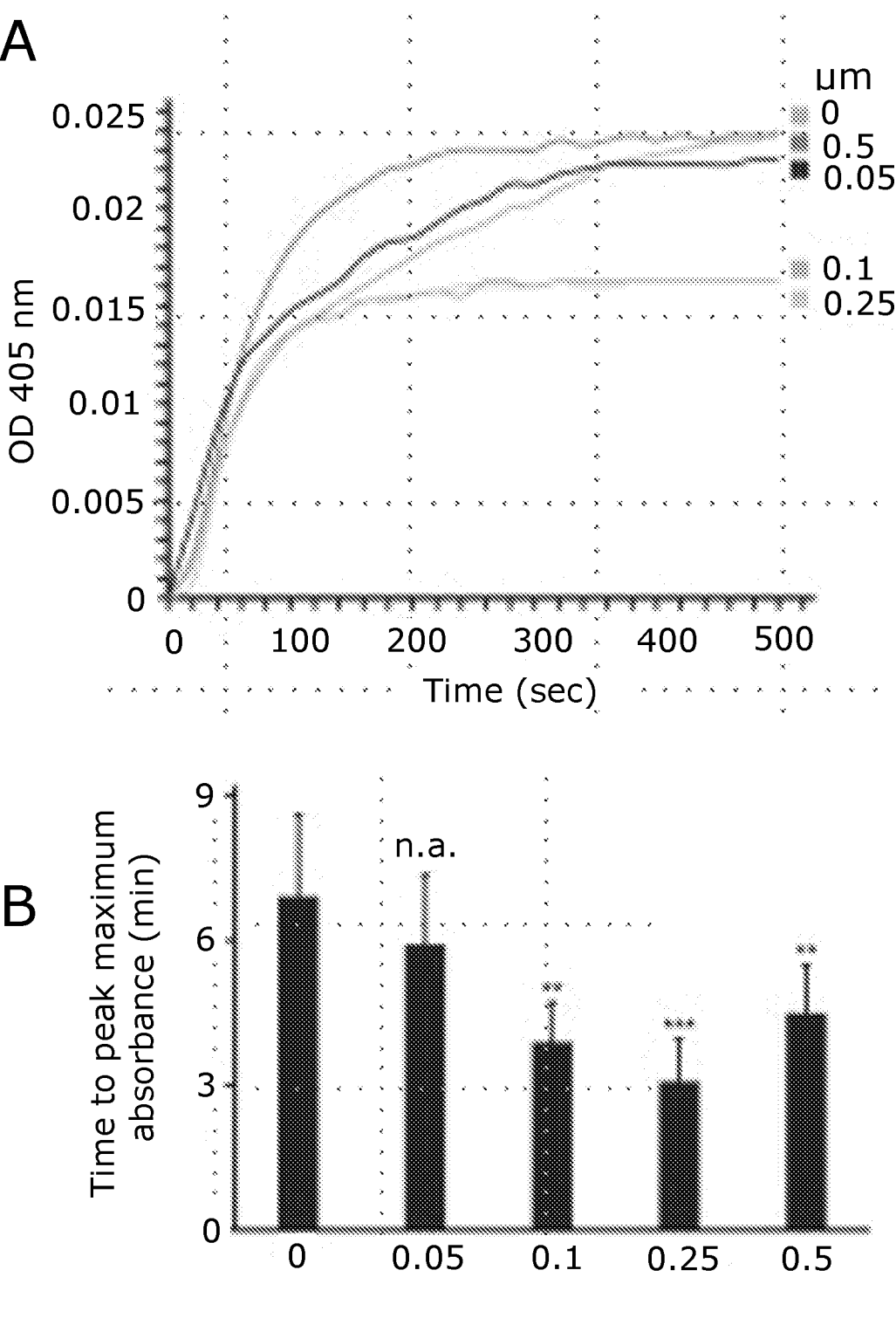
FIGS. 16A-16B. The A2 protein modulates the rate of fibrin formation in vitro.
Figure 24:
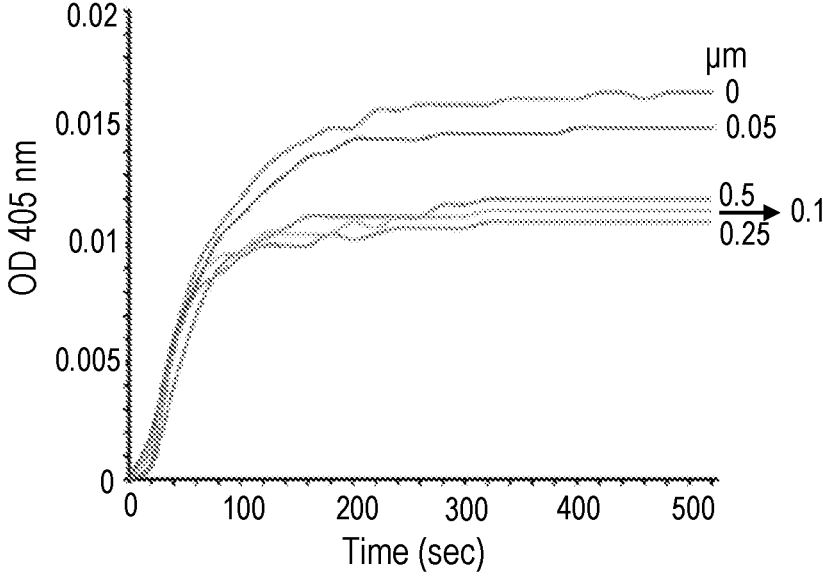
Figure 24:
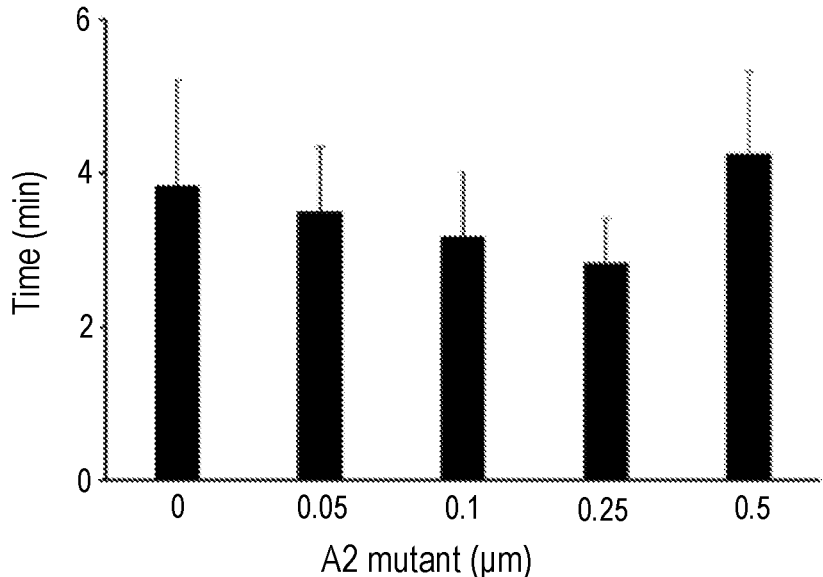

FIGS. 24A-24B. FIG. 24A. As described for FIG. 16, the A2 mutant did not modulate the rate of fibrin formation in vitro. FIG. 24A fibrin was formed from using 10% healthy human plasma and vehicle control or A2 protein (0-0.5 μM) and turbidity was measured at λ 405 nm. The tracings shown are the average of four separate experiments. The initial rate of change (slope) were equivalent at all the tested concentrations of A2 mutant. FIG. 24B, bar graph shows the non-significant effect of the mutant A2 protein on the time to peak maximal absorbance in FIG. 24A. This represents four experiments using plasma from two healthy human donors (n=4 paired subjects). N.S. (p>0.3) for all tested conditions versus control (no A2).

Figure 17:
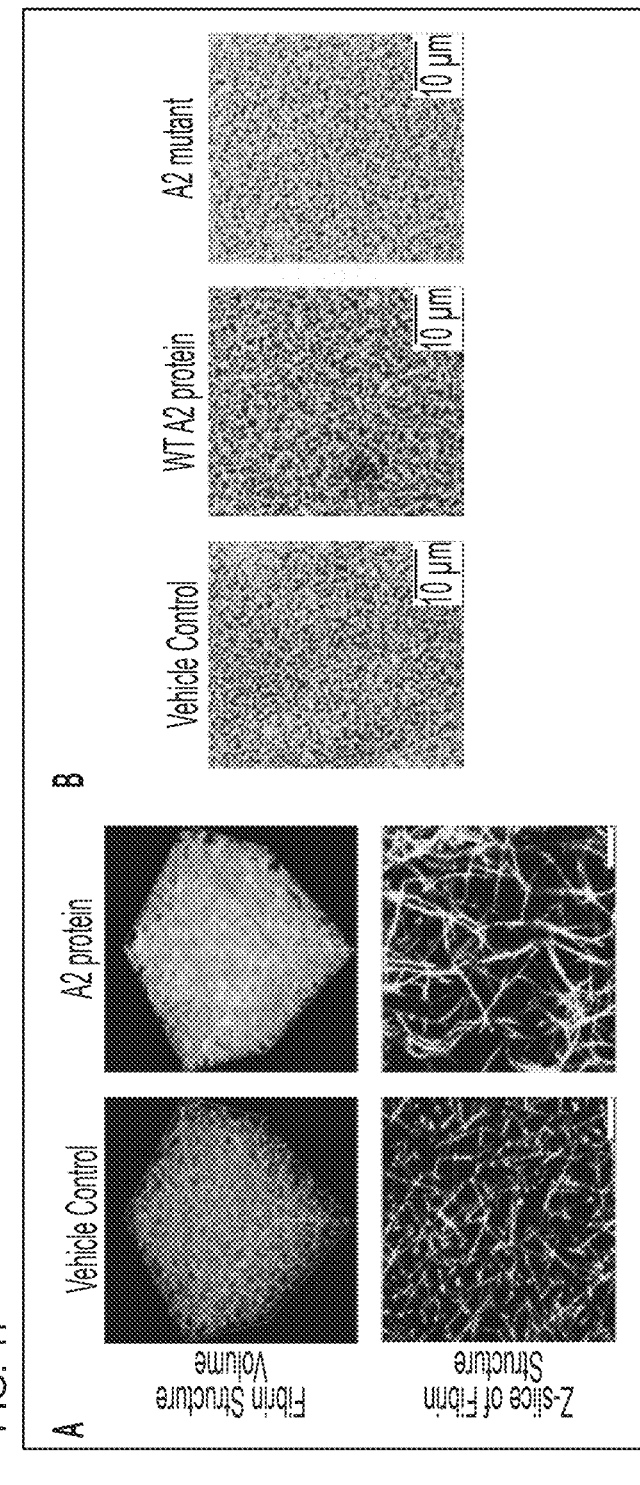
FIGS. 17A-17B. The effect of the A2 protein on the fibrin clot structure.
Figure 25:
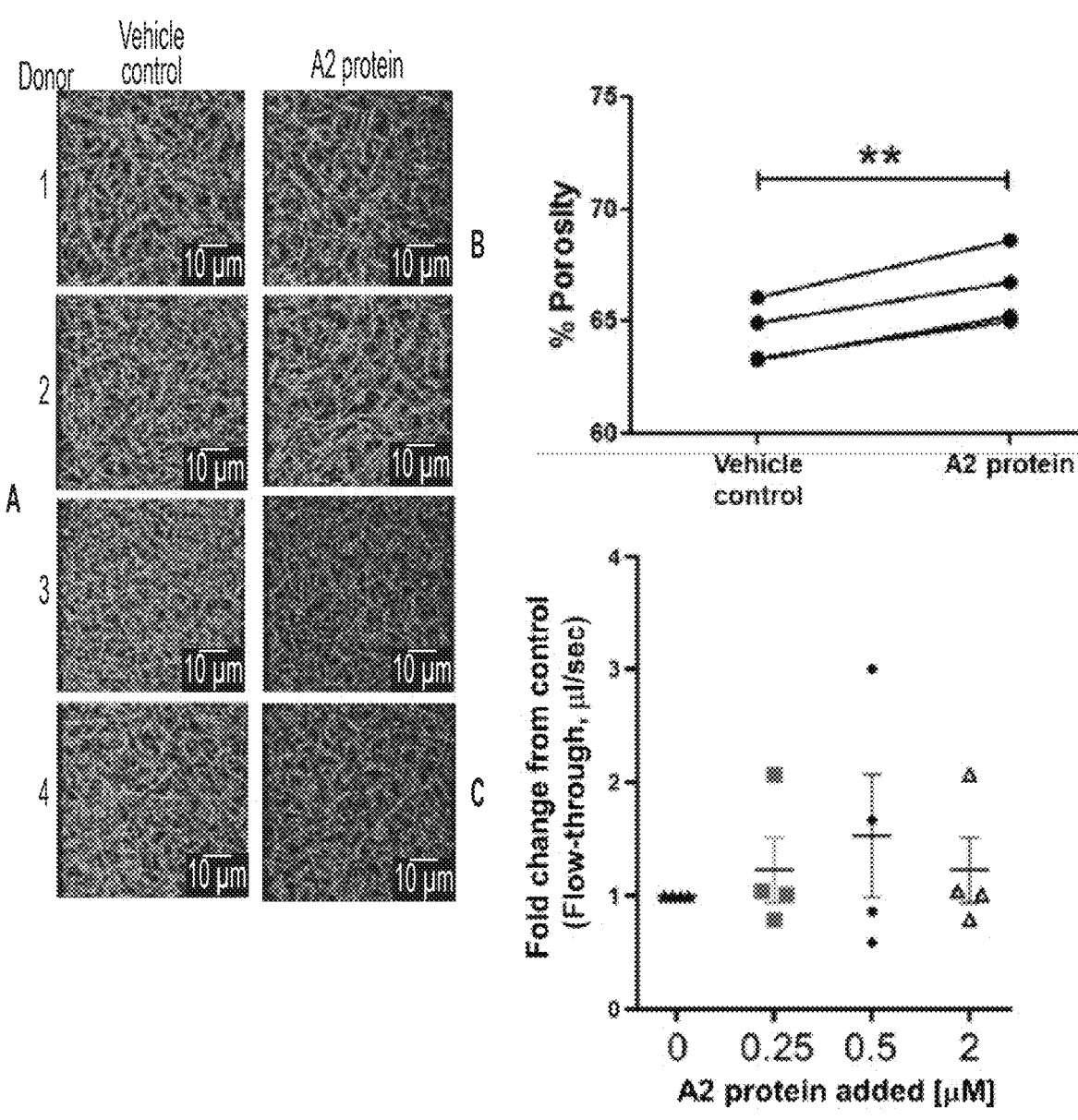

FIGS. 25A-25C. As described for FIG. 17, FIG. 25A shows additional confocal microscopy images of fibrin clots at magnification of 200× formed in plasma from healthy human donors. The A2 protein (0.5 μM) affected the resultant clot structure (right panels). FIG. 25B. Graph depicting the quantitative analysis of the fibrin porosity shown in A. ImageJ was used to measure the dark areas within the resultant confocal images of the fibrin networks. (n=4 paired subjects) p<0.005 versus control. FIG. 25C**. Fold change from control, 0 μM, (flow-through, μl per second) as a function of added A2 protein for fibrin clots (200 μl) formed by incubation (20 min, 22° C.) of 40% plasma from healthy donors with 1 U/ml thrombin. Error bars represent the mean f standard deviation for four measurements with each clot. N.S. (p>0.5) for the two tested conditions versus control (no A2).

Figure 26:
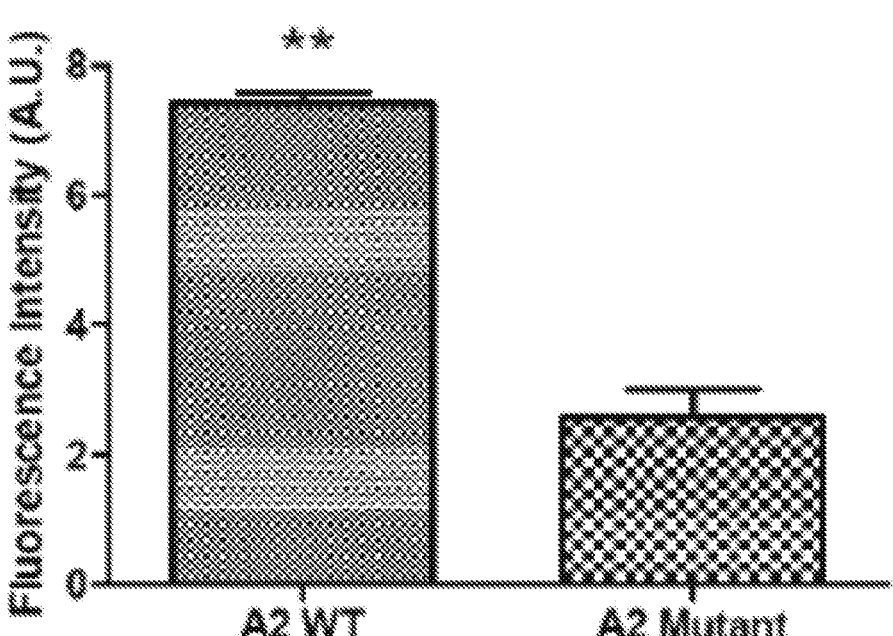

FIG. 26. Graph depicting the quantitative analysis of the A2 protein or A2 mutant incorporated into the fibrin network at 300× magnification as in FIG. 25B. ImageJ was used to measure the fluorescence intensity within the resultant confocal images of the fibrin networks. (n=3 paired subjects) **p<0.0088 versus control.

Figure 27:
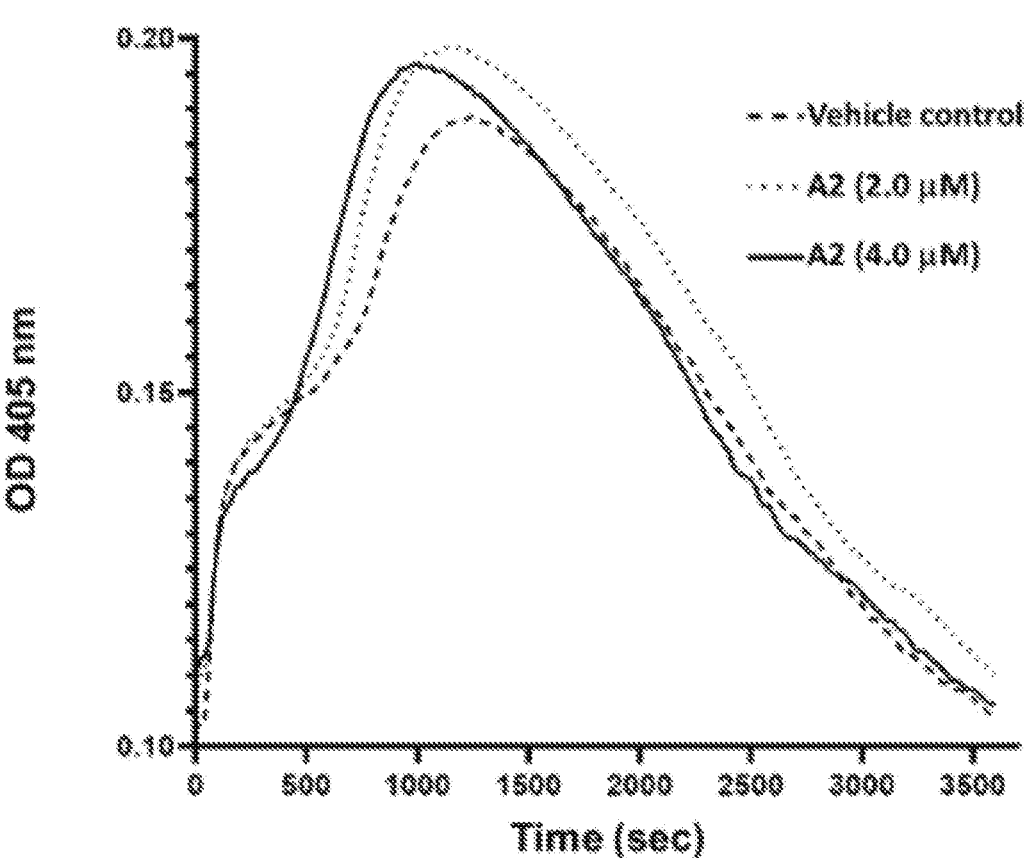

FIG. 27. The A2 protein does not significantly disrupt fibrinolysis in healthy human plasma in vitro. Fibrin was formed from using healthy human plasma supplemented with tPA, and vehicle control or WT A2 protein. Turbidity was measured at λ 405 nm. The tracings shown are representative of 3 experiments.

Figure 28:
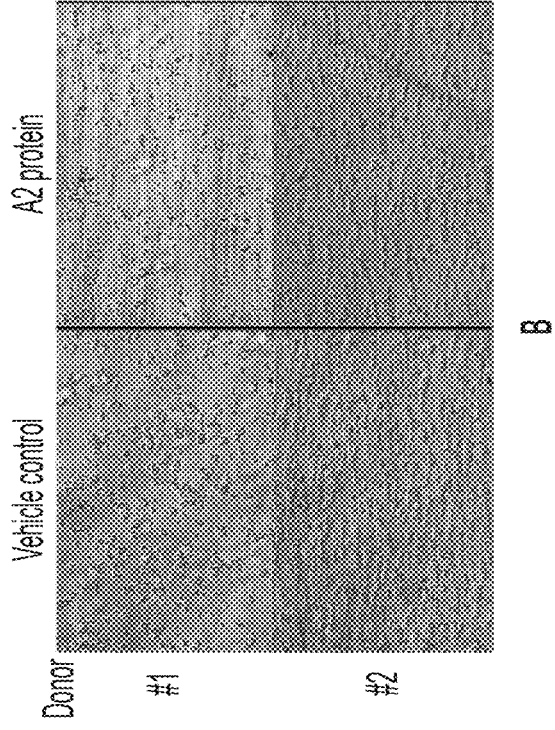
Figure 28:
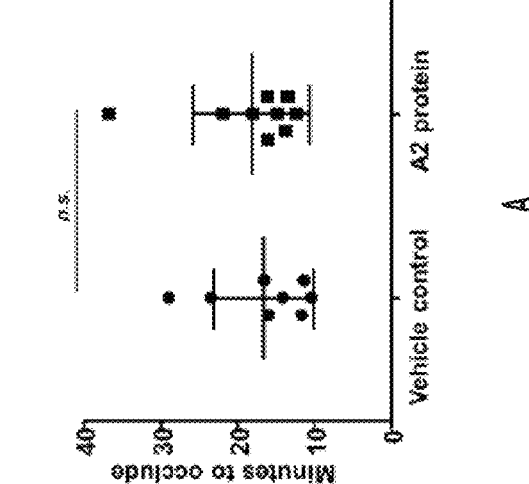

FIG. 28A-28B. FIG. 28A. Thrombosis kinetics were assessed by a light-dye injury model using intravital microscopy. Vessel occlusion was recorded in minutes. Data shown as mean±SE, n=8 per group. FIG. 28B. Vehicle control or A2 protein (4.0 μM). The blood was perfused over a surface coated with collagen Type III (50 µg/ml) at high shear stress (60 dyn/cm²). Buildup of the platelets was recorded during the 10-min perfusion.

Figure 29:
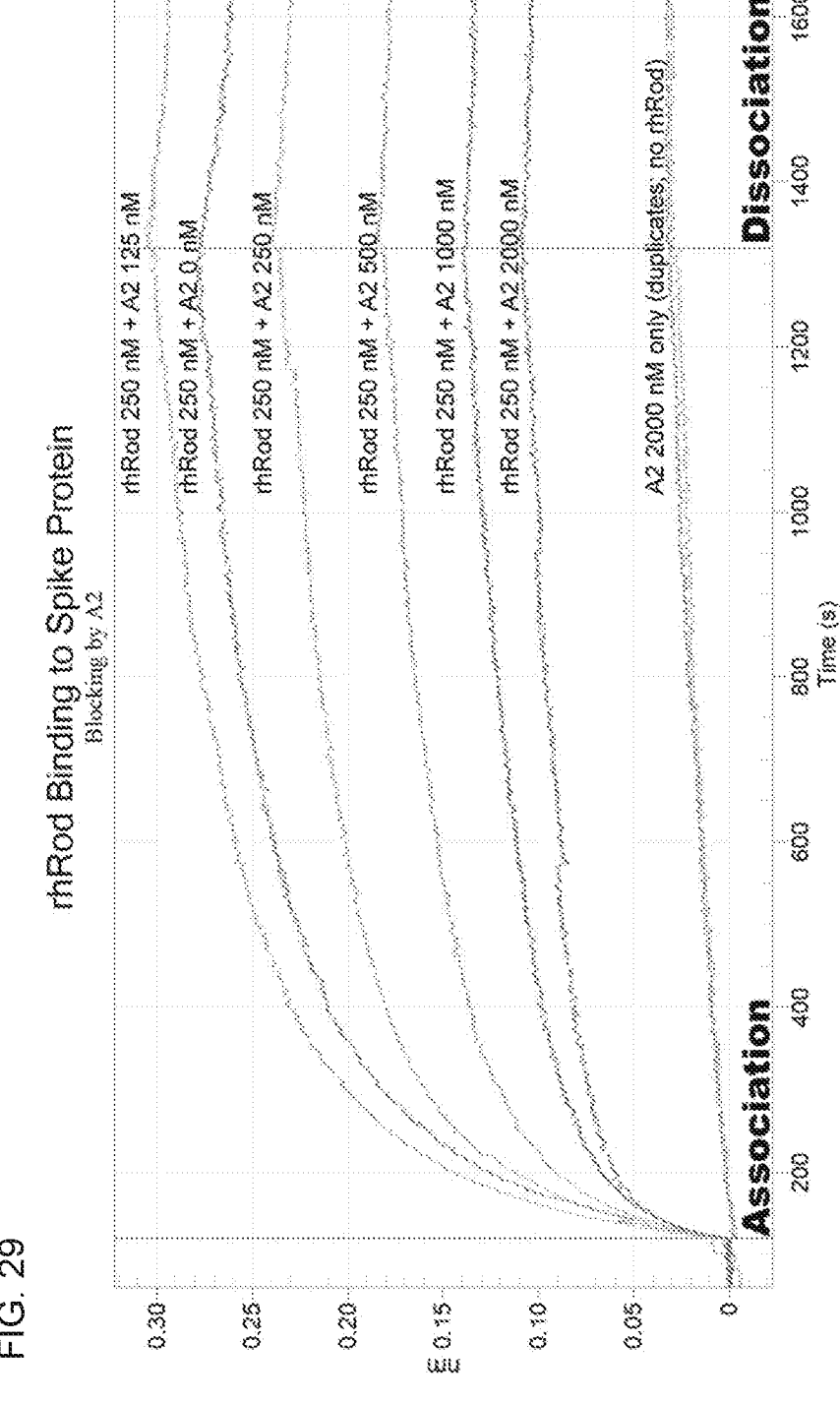

FIG. 29. Recombinant A2 domain of VWF blocks the binding of SARS-CoV-2 spike protein to the recombinant rod domain of vimentin.

DETAILED DESCRIPTION

I. Exemplary Definitions

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Recitation of ranges of values herein are merely intended to serve as a shorthand method of referring individually to each separate value falling within the range, unless other-wise indicated herein, and each separate value is incorporated into the specification as if it were individually recited herein.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "subject," as used herein, generally refers to an individual having a or at risk of having a medical condition, including a medical condition associated with fibrin or dysregulation thereof. A subject can be an animal. The subject can be any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as one or more infectious diseases, one or more genetic disorders, one or more cancers, a pregnant subject, or any combination thereof. The disease may be genetic or pathogenic. The subject may be asymptomatic. The subject may or may not have been diagnosed with the medical condition. The subject may be a healthy individual. The term "individual" may be used interchangeably, in at least some cases. The "subject" or "individual", as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants and includes in utero individuals. It is not intended that the term connote a need for medical treatment, therefore, an individual may voluntarily or involuntarily be part of experimentation whether clinical or in support of basic science studies.

As used herein, the phrase "subject in need thereof" or "individual in need thereof" refers to a subject or individual, as described infra, that suffers or is at a risk of suffering (e.g, pre-disposed such as genetically pre-disposed, or subjected to environmental conditions that pre-dispose, etc.) from the diseases or conditions listed herein (e.g, thrombosis, sepsis, coronavirus infection).

As used herein, the term "therapeutically effective amount" is synonymous with "effective amount", "therapeutically effective dose", and/or "effective dose" refers to an amount of an agent sufficient to ameliorate at least one symptom, behavior or event, associated with a pathological, abnormal or otherwise undesirable condition, or an amount sufficient to prevent or lessen the probability that such a condition will occur or re-occur, or an amount sufficient to delay worsening of such a condition. Effective amount can also mean the amount of a compound, material, or composition comprising a compound of the present disclosure that is effective for producing some desired effect, e.g., prevention of thrombosis and/or sepsis, prevention of binding of coronavirus to cell surface receptors. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly. Further, one of skill in the art recognizes that an amount may be considered effective even if the medical condition is not totally eradicated but improved partially. For example, the medical condition may be halted or reduced or its onset delayed, a side effect from the medical condition may be partially reduced or completed eliminated, and so forth.

As used herein, the terms "treatment," "treat," or "treating" refers to intervention in an attempt to alter the natural course of the individual or cell being treated, and may be performed either for prophylaxis or during the course of pathology of a disease or condition such as for example thrombosis; sepsis comprising disseminated intravascular coagulation (DIC), fever, systemic inflammation, tachycardia, or a combination thereof; and/or coronavirus infection comprising pneumonia, organ failure, blood clots, respiratory failure, heart conditions such as cardiomyopathies, acute kidney injury, further viral and bacterial infections, or a combination thereof. Treatment may serve to accomplish one or more of various desired outcomes, including, for example, preventing occurrence or recurrence of disease, alleviation of symptoms, and diminishment of any direct or indirect pathological consequences of the disease, lowering the rate of disease progression, amelioration or palliation of the disease state, remission or improved prognosis, and/or producing some desired effect, e.g., prevention of thrombosis and/or sepsis, prevention of binding of coronavirus to cell surface receptors. The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel.

General Embodiments Related to Fibrin and the A2 Domain

The present disclosure includes methods and compositions related to medical conditions indirectly or directly associated with fibrin, dysregulation of fibrin, and any imbalances thereof. In particular embodiments, the methods and compositions relate to medical conditions indirectly or directly associated with fibrinolysis at a level that is deleterious to the health of the individual, such as is indicated by one or more symptoms associated therewith. The methods allow for maintaining fibrin network in the individual. The methods include treatment and preventative steps for avoiding fibrinolysis levels that are deleterious to the health of the individual and also of fibrin networks having structure that is lacking appropriate maintenance.

Particular methods of the disclosure include the targeting of fibrin to maintain or repair a fibrin network in an individual. Such targeting to establish, preserve, reform, improve, reconstruct, or otherwise alter a fibrin network in an individual utilizes part or all of an effective amount of the A2 domain of von Willebrand factor or a functional derivative or fragment thereof. Use of A2 or a functional derivative or fragment thereof allows for targeting of the fibrin network, for example to modify the structure of fibrin in an individual in need thereof. In specific cases at least, the A2 or a functional derivative or fragment thereof improves a fibrin network in an individual by directly binding the fibrin network.

Methods of the disclosure allow for increasing the rate of fibrin polymerization in an individual. In at least certain methods, the methods reduce the consumption of one or more coagulation factors in the individual, including preventing overconsumption of one or more coagulation factors. The methods allow for tempering pro-inflammatory responses of any kind, including those associated with coagulation. Specific methods of the disclosure improve imbalance between coagulation and inflammation of any kind including at least that associated with DIC.

In certain methods of the disclosure, the individual has excessive fibrinolysis compared to a standard or control population, including compared to the general population or to a level previously identified in the individual.

Embodiments of the disclosure encompass the targeting of fibrin to attenuate any deleterious medical condition associated with fibrin, such as DIC, sepsis, sepsis-induced DIC, sepsis-induced multiple organ dysfunction syndrome, pregnancy, myocardial infarction, cancer, traumatic brain injury, hypoxic-ischemic brain injury, trauma induced coagulopathy, stroke, inflammatory bowel disease, antiphospholipid syndrome, rheumatoid arthritis, chronic obstructive pulmonary disease, diabetes mellitus, end stage renal disease, malignancy, liver cirrhosis, deep vein thrombosis, pulmonary embolism, reperfusion injury, liver ischemic reperfusion, kidney ischemic reperfusion, microvascular thrombosis and/or organ injuries in systemic inflammation. Methods include maintaining a fibrin network in an individual by delivering to the individual an effective amount of the A2 domain of von Willebrand factor or a functional derivative or fragment thereof. Methods encompass targeting of fibrin to maintain or repair or preserve a fibrin network in an individual by delivering to the individual an effective amount of the A2 domain of von Willebrand factor or a functional derivative or fragment thereof.

Embodiments of the disclosure include targeting the fibrin clot structure to reduce microvascular thrombosis, such as in systemic inflammation. Delivery of the A2 protein reduces microvascular thrombosis, micro-hemorrhages and D-dimer levels in an individual with fibrinolysis dysregulation, including with sepsis, such as MRSA sepsis.

Methods of attenuating DIC (from small blood clots that develop throughout the bloodstream, blocking small blood vessels, leading to increased clotting that depletes the platelets and clotting factors needed to control bleeding, resulting in excessive bleeding) are included herein, including by targeting of fibrin with an effective amount of the A2 domain of von Willebrand factor or a functional derivative or fragment thereof.

Methods of the disclosure encompass modifying fibrin clot structure and stability to prevent hemorrhage and/or thrombosis upon directed targeting of the fibrin with an effective amount of the A2 domain of von Willebrand factor or a functional derivative or fragment thereof. The directed targeting may be a purpose of the methods of the disclosure and encompass methods in which the effective amount of the A2 domain of von Willebrand factor or a functional derivative or fragment thereof are provided to the individual for the explicit purpose of targeting fibrin.

Direct interaction with fibrin in specific aspects of the disclosure include in certain embodiments the modifying of a fibrin clot structure, including a fibrin clot structure that is more susceptible for fibrinolysis. Methods of delaying clot formation are encompassed herein by direct targeting of fibrin with A2 domain of von Willebrand factor or a functional derivative or fragment thereof.

Methods of the disclosure reduce the extent of microvascular thrombosis and fibrin deposition caused for any reason. The A2 domain or a functional derivative or fragment thereof diminishes fibrin deposition, fibrin-rich microthrombi formation, micro-hemorrhages, and organ injuries in an individual, including following MRSA infection and/or sepsis.

The targeting of fibrin with A2 domain or a functional derivative or fragment thereof includes methods of attenuating organ injuries associated with systemic inflammation and/or sepsis, including without causing increasing bleeding or impairing primary hemostasis. The fibrin-targeting methods protect an individual from MRSA or one or more symptoms, including systemic inflammation, fever, and/or tachycardia.

Methods of the disclosure include embodiments that reduce or prevent consumption of one or more coagulation factors (including any one or more of Factor I (fibrinogen); Factor II (prothrombin); Factor III (tissue thromboplastin (tissue factor)); Factor IV (ionized calcium (Ca++)); Factor V (labile factor or proaccelerin); Factor VI; Factor VII (stable factor or proconvertin); Factor VIII (antihemophilic factor); Factor IX (plasma thromboplastin component, Christmas factor); Factor X (Stuart-Prower factor); Factor XI (plasma thromboplastin antecedent); Factor XII (Hageman factor); or Factor XIII (fibrin-stabilizing factor). The coagulation factor consumption that is prevented or reduced in methods of the disclosure may be for any reason, including for DIC, sepsis, sepsis-induced DIC, sepsis-induced multiple organ dysfunction syndrome, pregnancy, myocardial infarction, cancer, traumatic brain injury, hypoxic-ischemic brain injury, trauma induced coagulopathy, stroke, inflammatory bowel disease, antiphospholipid syndrome, rheumatoid arthritis, chronic obstructive pulmonary disease, diabetes mellitus, end stage renal disease, malignancy, liver cirrhosis, deep vein thrombosis, pulmonary embolism, reperfusion injury, liver ischemic reperfusion, kidney ischemic reperfusion, microvascular thrombosis and/or organ injuries in systemic inflammation.

Methods and compositions of the disclosure encompass prevention and treatment of one or more thrombotic disorders. In healthy people, homeostatic balance exists between procoagulant (clotting) forces and anticoagulant and fibrinolytic forces. Numerous genetic, acquired, and environmental factors can tip the balance in favor of coagulation, leading to the pathologic formation of thrombi in veins (e.g., deep venous thrombosis [DVT]), arteries (e.g., myocardial infarction, ischemic stroke), or cardiac chambers. Thrombi can obstruct blood flow at the site of formation or detach and embolize to block a distant blood vessel (e.g., pulmonary embolism, embolic stroke). Methods and compositions of the disclosure prevent or delay the aforementioned coagulation, obstruction of blood flow (including at the site of formation or upon detachment), embolization, and so forth. Methods and compositions of the disclosure can also prevent or delay dysregulated activated coagulation. As used herein, "dysregulated activated coagulation" refers to an uncontrolled and/or uninhibited coagulation system in which the normal physiological events that occur in the coagulation cascade are defective or excessively reacting leading to excessive clotting and/or both clotting and bleeding.

II. General Embodiments Related to Coronavirus and the A2 Domain

In particular embodiments, the disclosure concerns compositions, methods, and systems that modulate coronavirus infection in an individual, including viral interaction with cells and/or tissues. One way to block viral interaction with cells is through inhibiting the binding of the virus to cell surface receptors. The A2 domain of von Willebrand factor contains a cleavage site, which is important for scission of von Willebrand factor down to size to facilitate platelet adhesion. As described herein, the A2 protein can also prevent or inhibit binding of viral proteins, including coronavirus spike protein, by cell surface receptors including vimentin or the rod domain thereof (rhRod) and/or ACE2.

In certain aspects, coronavirus infections are related to SARS or respiratory infections. SARS or respiratory infections are associated with a variety of complications or medical conditions, including at least pneumonia, organ failure, blood clots, respiratory failure, heart conditions such as cardiomyopathies, acute kidney injury, further viral and bacterial infections, or a combination thereof. In particular embodiments of the disclosure, there is a decrease morbidity and mortality from pneumonia, organ failure, blood clots, respiratory failure, heart conditions such as cardiomyopathies, acute kidney injury, and/or further viral and bacterial infections by modulating coronavirus infection, especially because there are no effective therapies to prevent or treat this disease. Without wishing to be bound by theory, the A2 domain can inhibit coronavirus infection and the resulting complications by blocking viral infiltration into the lungs. Specifically, the A2 domain can prevent or inhibit interactions between coronavirus spike proteins and cell surface receptors such as vimentin or the rod domain thereof (rhRod) and/or ACE2. Thus, by modulating viral infection, one can reduce morbidity and mortality from coronavirus, resulting SARS or respiratory infections, and complications or medical conditions including pneumonia, organ failure, respiratory failure, blood clots, heart conditions such as cardiomyopathies, acute kidney injury, and/or further viral and bacterial infections.

Coronaviruses make up a large family of viruses that can infect birds and mammals, including humans, according to the World Health Organization (WHO). These viruses have been responsible for several outbreaks around the world, including the severe acute respiratory syndrome (SARS) pandemic of 2002-2003 and the Middle East respiratory syndrome (MERS) outbreak in South Korea in 2015. Most recently, a novel coronavirus (SARS-CoV-2, also known as SARS-associated coronavirus 2 or COVID-19) triggered an outbreak in China in December 2019.

Coronaviruses constitute the subfamily Orthocoronavirinae, in the family Coronaviridae, order Nidovirales, and realm Riboviria. They have characteristic club-shaped spikes that project from their surface, which in electron micrographs create an image reminiscent of the solar corona, from which their name derives. The average diameter of the virus particles is around 120 nm (0.12 μm). The diameter of the envelope is ~80 nm (0.08 μm) and the spikes are ~20 nm (0.02 μm) long. Beneath a coronavirus's spiked exterior is a round core shrouded in a viral envelope. The core contains genetic material that the virus can inject into vulnerable cells to infect them.

The viral envelope consists of a lipid bilayer where the membrane (M), envelope (E), and spike (S) structural proteins are anchored. Inside the envelope, there is the nucleocapsid of helical symmetry which is formed from multiple copies of the nucleocapsid (N) protein, which are bound to the positive-sense single-stranded RNA genome in a continuous beads-on-a-string type conformation. The genome size of coronaviruses ranges from approximately 26 to 32 kilobases, one of the largest among RNA viruses. The genome organization for a coronavirus is 5'-leader-UTR-replicase/transcriptase-spike (S)-envelope (E)-membrane (M)-nucleocapsid (N)-3'UTR-poly (A) tail. The open reading frames 1a and 1b, which occupy the first two-thirds of the genome, encode the replicase/transcriptase polyprotein. The replicase/transcriptase polyprotein self cleaves to form nonstructural proteins. The later reading frames encode the four major structural proteins: spike, envelope, membrane, and nucleocapsid. Interspersed between these reading frames are the reading frames for the accessory proteins. The number of accessory proteins and their function is unique depending on the specific coronavirus.

The lipid bilayer envelope, membrane proteins, and nucleocapsid protect the virus when it is outside the host cell. The spike proteins extend from within the core to the viral surface and allow the virus to recognize and bind specific cells in the body. When the spike engages a receptor on a host cell, a cascade is triggered, resulting in the merger of the virus with the cell which allows the virus to release its genetic material and overtake the cell's processes to produce new viruses.

Several coronaviruses utilize animals as their primary hosts and have evolved to infect humans, too. Precursors to both SARS and MERS coronaviruses appear in bats. The SARS virus jumped from bats to civets (small, nocturnal mammals) on its way into people, while MERS infected camels before spreading to humans. Evidence suggests that the novel coronavirus also jumped from bats to humans after passing through an intermediate carrier, although scientists have not yet identified the infectious middleman creature. Human coronaviruses were first identified in the mid-1960s. There are four main sub-groupings of coronaviruses, known as alpha, beta, gamma, and delta, and seven coronaviruses that can infect people. The four most common coronaviruses did not jump from animals to humans but rather utilize humans as their natural hosts; these include: 229E (alpha coronavirus); NL63 (alpha coronavirus); OC43 (beta coronavirus); HKU1 (beta coronavirus). Three other human coronaviruses are: MERS-CoV (the beta coronavirus that causes Middle East Respiratory Syndrome, or MERS); SARS-CoV (the beta coronavirus that causes severe acute respiratory syndrome, or SARS); and SARS-CoV-2 (the novel coronavirus that causes coronavirus disease 2019, or COVID-19).

Data has shown that the viruses can spread from person to person among those in close contact (within about 6 feet, or 2 meters). The viruses spread by respiratory droplets released when someone with the virus coughs, sneezes, or talks. These droplets can be inhaled or land in the mouth or nose of a person nearby. They can also spread if a person touches a surface with a virus on it and then touches his or her mouth, nose, or eyes.

Infection begins when the viral spike (S) glycoprotein attaches to its complementary host cell receptor. After attachment, a protease of the host cell cleaves and activates the receptor-attached spike protein. Depending on the host cell protease available, cleavage and activation allows the virus to enter the host cell by endocytosis or direct fusion of the viral envelop with the host membrane. On entry into the host cell, the virus particle is uncoated, and its genome enters the cell cytoplasm. The coronavirus RNA genome has a 5' methylated cap and a 3' polyadenylated tail, which allows the RNA to attach to the host cell's ribosome for translation. The host ribosome translates the initial overlapping open reading frame of the virus genome and forms a long polyprotein. The polyprotein has its own proteases which cleave the polyprotein into multiple nonstructural proteins.

Viral entry is followed by replication of the virus. A number of the nonstructural proteins coalesce to form a multi-protein replicase-transcriptase complex (RTC). The main replicase-transcriptase protein is the RNA-dependent RNA polymerase (RdRp). It is directly involved in the replication and transcription of RNA from an RNA strand. The other nonstructural proteins in the complex assist in the replication and transcription process. The exoribonuclease nonstructural protein, for instance, provides extra fidelity to replication by providing a proofreading function which the RNA-dependent RNA polymerase lacks. One of the main functions of the complex is to replicate the viral genome. RdRp directly mediates the synthesis of negative-sense genomic RNA from the positive-sense genomic RNA. This is followed by the replication of positive-sense genomic RNA from the negative-sense genomic RNA. The other important function of the complex is to transcribe the viral genome. RdRp directly mediates the synthesis of negative-sense subgenomic RNA molecules from the positive-sense genomic RNA. This is followed by the transcription of these negative-sense subgenomic RNA molecules to their corresponding positive-sense mRNAs.

The replicated positive-sense genomic RNA becomes the genome of the progeny viruses. The mRNAs are gene transcripts of the last third of the virus genome after the initial overlapping reading frame. These mRNAs are translated by the host's ribosomes into the structural proteins and a number of accessory proteins. RNA translation occurs inside the endoplasmic reticulum. The viral structural proteins S, E, and M move along the secretory pathway into the Golgi intermediate compartment. There, the M proteins direct most protein-protein interactions required for assembly of viruses following its binding to the nucleocapsid. Progeny viruses are then released from the host cell by exocytosis through secretory vesicles.

The interaction of the coronavirus spike protein with its complement host cell receptor is central in determining the tissue tropism, infectivity, and species range of the virus. Coronaviruses mainly target epithelial cell receptors. They are transmitted from one host to another host, depending on the coronavirus species, by either an aerosol, fomite, or fecal-oral route. Human coronaviruses infect the epithelial cells of the respiratory tract, while animal coronaviruses generally infect the epithelial cells of the digestive tract. SARS coronavirus infects, for example, via an aerosol route, human epithelial cells of the lungs by binding to the angiotensin-converting enzyme 2 (ACE2) receptor.

The WHO has reported that the two groups most at risk of experiencing severe illness due to a coronavirus infection are adults aged 65 years or older and people who have other underlying health conditions including chronic lung disease, serious heart conditions, severe obesity, a compromised immune system, or diabetes. In humans, coronaviruses typically cause a respiratory infection with mild to severe flu-like symptoms, but the exact symptoms vary depending on the type of coronavirus. The four common human coronaviruses can cause people to develop a runny nose, headache, cough, sore throat and fever, according to the CDC. In a subset of individuals, including those with cardiopulmonary disease or a weakened immune system, the viral infection can progress to a more severe lower-respiratory infection such as pneumonia or bronchitis. In comparison, severe MERS and SARS infections often progress to pneumonia. Other symptoms of MERS include fever, coughing, and shortness of breath, while SARS can cause fever, chills and body aches.

SARS-CoV-2 causes symptoms similar to those of other coronaviruses, triggering fever, cough, and shortness of breath in most patients. Rarer symptoms include dizziness, tiredness, aches, chills, sore throat, loss of smell, loss of taste, headache, nausea, vomiting, and diarrhea. Emergency signs or symptoms can include trouble breathing, persistent chest pain or pressure, new confusion, and/or blue lips or face. Complications of SARS-CoV-2 infections can include pneumonia, organ failure, respiratory failure, blood clots, heart conditions such as cardiomyopathies, acute kidney injury, and/or further viral and bacterial infections. Further, in some cases, individuals may have dysregulated activated coagulation or may be at risk for having dysregulated activated coagulation.

Doctors can test for coronavirus infections by analyzing respiratory specimens and serum isolated from blood. The CDC has developed an equivalent diagnostic test for SARS-CoV-2, but its accuracy and specificity for the virus are still being verified. As of yet, there are no available treatments for or vaccines to prevent any human coronavirus. Those who catch a common coronavirus usually recover on their own. Similar regimens are used to relieve the symptoms of more severe coronavirus infections.

Embodiments of the disclosure include methods of delivering a therapeutically effective amount of one or more A2 domain compositions to an individual in need thereof. In specific embodiments, the individual has or is at risk for having coronavirus infection. The individual may have a condition that has as a symptom and/or a mechanism an increase in binding of viral particles to cell surface receptors, for example. Embodiments of the disclosure include treatment or prevention of any medical condition in which modulation of coronavirus infection would be beneficial. In specific embodiments, an individual is provided a therapeutically effective amount of one or more A2 domain compositions for attenuation of coronavirus infection in an individual, including when the individual has dysregulation of physiological processes following coronavirus infection which can lead to SARS or respiratory infections (including COVID-19) and complications including pneumonia, organ failure, respiratory failure, blood clots, heart conditions such as cardiomyopathies, acute kidney injury, and/or further viral and bacterial infections.

In specific embodiments, the medical condition treated or prevented with the A2 domain comprises SARS or respiratory infections which can lead to pneumonia, organ failure, blood clots, respiratory failure, heart conditions such as cardiomyopathies, acute kidney injury, viral and bacterial infections, or a combination thereof.

In particular embodiments, coronavirus infection is not treated with compositions, methods, and systems of the disclosure but instead is prevented, reduced in severity, or there is a delay in onset, for example. In some cases, the the A2 domain treats or prevents the medical condition in the individual by inhibiting coronavirus binding to cell surface receptors such as ACE2 and/or vimentin or the rod domain thereof (rhRod), for example.

Embodiments of the disclosure include compositions and methods that prevent the development of SARS or respiratory infection or the progression from SARS or respiratory infection to pneumonia, organ failure, respiratory failure, blood clots, heart conditions such as cardiomyopathies, acute kidney injury, and/or further viral and bacterial infections, as a result of coronavirus infection. In some cases, once an individual appears to be at risk for developing SARS or respiratory infection, pneumonia, organ failure, respiratory failure, blood clots, heart conditions such as cardiomyopathies, acute kidney injury, and/or further viral and bacterial infections, or requiring intubation, an individual is given an effective amount of one or more A2 domain compositions as part of their care. In some cases, an individual at risk for having dysregulated activated coagulation as a result of SARS is given an effective amount of one or more A2 domain compositions as part of their care. As used herein, "dysregulated activated coagulation" refers to an uncontrolled and/or uninhibited coagulation system in which the normal physiological events that occur in the coagulation cascade are defective or excessively reacting leading to excessive clotting and/or both clotting and bleeding.

In specific cases, delivery of the A2 domain to an individual blocks the binding of coronavirus to cell surface receptors which leads to SARS or respiratory infection. Specific embodiments of the disclosure include compositions and methods in which an A2 domain composition targets the spike proteins of coronavirus. In particular, the A2 domain inhibits viral infection by inhibiting coronavirus binding to cell surface receptors via blocking coronavirus spike protein interactions with cell surface receptors. In particular cases, the A2 domain inhibits the interaction between the vimentin and/or rhRod and coronavirus spike proteins for a therapeutic outcome.

Although in some cases the A2 domain composition is provided as a sole therapy for the individual, in some cases the individual is provided a second therapy. The second therapy may be of any kind, but in specific cases the second therapy is antibiotics, antivirals, convalescent serum from previously infected-individuals recovered from coronavirus, immune modulators, anticoagulants, fluids, oxygen, a corticosteroid, antibodies, GSnP-6, sialyl Lewis X analog, anti-proliferatives, calcineurin inhibitors, anti-signaling compounds, or a combination thereof. The A2 domain compositions may also be a second therapy to attenuate SARS or respiratory infection until the primary process is resolved (e.g., resolution of coronavirus infection)

In particular embodiments, an individual that is at risk for coronavirus infection leading to SARS or respiratory infection or that is known to have coronavirus infection is provided a therapeutically effective amount of one or more A2 domain compositions. In some cases, the individual has been diagnosed with coronavirus infection or SARS or respiratory infection, for example. In some cases, the individual is at risk of contracting coronavirus infection which can lead to SARS or respiratory infection. Risk factors for contracting coronavirus infection which can lead to SARS or respiratory infection include advanced age and/or underlying medical conditions including chronic lung disease, serious heart conditions, severe obesity, a compromised immune system, or diabetes, and an individual characterized by one or more of these risk factors may be provided an effective amount of one or more A2 domain compositions.

In some embodiments, a medical condition is treated or prevented with an A2 domain composition that is delivered to the individual multiple times, such as once a day, more than once a day, one a week, more than once a week, once a month, more than once a month, once a year, or more than once a year. The multiple treatments may or may not have the same formulations and/or routes of administration(s). Any administration may be as a continuous infusion.

The provider skilled in the art of medical care and decision may determine an appropriate end-point for an A2 domain composition therapy based on the specific disease process and clinical course of the patient or individual.

In specific embodiments, an additional viral therapy or preventative may be provided to the individual in combination with the disclosed treatment. In specific embodiments, the additional viral therapy or preventative is for a Coronaviridae family infection (including SARS-CoV-2) selected from the group consisting of Azithromycin, AC-55541, Apicidin, AZ3451, AZ8838, Bafilomycin A1, CCT 365623, Daunorubicin, E-52862, Entacapone, GB110, H-89, Haloperidol, Indomethacin, JQ1, Loratadine, Merimepodib, Metformin, Midostaurin, Migalastat, Mycophenolic acid, PB28, PD-144418, Ponatinib, Ribavirin, RS-PPCC, Ruxolitinib, RVX-208, S-verapamil, Silmitasertib, TMCB, UCPH-101, Valproic Acid, XL413, ZINC1775962367, ZINC4326719, ZINC4511851, ZINC95559591, 4E2RCat, ABBV-744, Camostat, Captopril, CB5083, Chloramphenicol, Chloroquine (and/or Hydroxychloroquine), CPI-0610, Dabrafenib, DBeQ, dBET6, IHVR-19029, Linezolid, Lisinopril, Minoxidil, ML240, MZ1, Nafamostat, Pevonedistat, PS3061, Rapamycin (Sirolimus), Sanglifehrin A, Sapanisertib (INK128/M1N128), FK-506 (Tacrolimus), Tematin 4 (DA3), Tigecycline, Tomivosertib (eFT-508), Verdinexor, WDB002, Zotatifin (eFT226), and a combination thereof.

III. The A2 Domain of Von Willebrand Factor

In particular embodiments of the disclosure, the A2 domain of von Willebrand Factor is employed in any methods of the disclosure. The A2 domain may be utilized as a whole or as a functional fragment thereof. For example, one of skill in the art may employ SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 as a particular embodiment of the A2 domain, or another A2 domain molecule may be used, such as one having conservative substitutions of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. In particular embodiments, there may be 1, 2, 3, 4, 5, 6, 7, 8, 9, 10, 11, 12, 13, 14, 15, or more conservative substitutions in the A2 domain. In other aspects of the disclosure, functional fragments of the A2 domain are used, and one of skill in the art may identify such fragments by standard means in the art. A functional fragment or derivative of A2 domain is one that can still bind to fibrin.

In certain aspects, exemplary synthetic peptides that narrow the N-terminal (half) A2 domain (1481-1605) may be utilized. A similar approach may be used for the C-terminal A2 polypeptide or any other polypeptide. Recombinant A2 domain polypeptide of VWF (published) is as follows: 1481-GLLGVSTLGPKRNSMVLDVAFVLEGSD- KIGEADFNRSKEFMEEVIQRMDVGQDSIHVTV LQYSYMVTVEYPFSEAQSKGDILQRVREIRYQGG-NRTNTGLALRYLSDHSFLVSQGDRE QAPNLVY-MVTGNPAS-DEIKRLPGDIQVVPIGVGPNANVQELERIGWPNAPILI QDF ETLPREAPDLVLQR-1668 (SEQ ID NO:1). The N-terminal (half) of the A2 domain of VWF (new) is as follows: 1481(718)-GLLGVSTLGPKRN-SMVLDVAFVLEGSDKIGEADFNR-SKEFMEEVIQRMDVGQDSIHVTV LQYSYMVTVEY-PFSEAQSKGDILQRVREIRYQGGNRTNTGLALRYLSD HSFLVSQGDRE QAPNLVY-(842)1605 (SEQ ID NO:2).

The C-terminal (half) of the A2 domain of VWF (new) is as follows: 1606(843)-MVTGNPAS-DEIKRLPGDIQVVPIGVGPNANVQELERIGWPNAP-ILIQDFETLPREAPDLVL QR-(905)1668 (SEQ ID NO:3).

The A2 domain may be obtained from the N-terminal region of A2. The A2 domain may be obtained from the C-terminal region of A2. In particular embodiments, functional fragments of the A2 domain may be utilized, such as the following:

```
                                    (SEQ ID NO: 4)
        GLLGVSTLGPKRNSM (SEQ ID NO: 5)
        NSMVLDVAFVLEGSD (SEQ ID NO: 6)
        GSDKIGEADFNRSKE (SEQ ID NO: 7)
        SKEFMEEVIQRMDVG (SEQ ID NO: 8)
        DVGQDSIHVTVLQYS (SEQ ID NO: 9)
        QYSYMVTVEYPFSEA (SEQ ID NO: 10)
        SEAQSKGDILQRVRE (SEQ ID NO: 11)
        VREIRYQGGNRTNTG (SEQ ID NO: 12)
        NTGLALRYLSDHSFL (SEQ ID NO: 13)
        SFLVSQGDREQAPNLVY (SEQ ID NO: 14)
        SKGDILQRVR (SEQ ID NO: 15)
        ILQRVREIRY (SEQ ID NO: 16)
        VREIRYQGGN (SEQ ID NO: 17)
        IGEADFNRSK (SEQ ID NO: 18)
        HVTVLQYSYM
```

The A2 domain may be further defined as a polypeptide comprising at least 70% identity, at least 75% identity, at least 80% identity, at least 85% identity, at least 90% identity, at least 95% identity, at least 97% identity, at least 98% identity, or at least 99% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18.

IV. Pharmaceutical Preparations

Exemplary pharmaceutical compositions of the present invention comprise an effective amount of one or more A2 domains of VWF or functional fragments or derivatives thereof or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one A2 domain of VWF or functional fragments or derivatives thereof or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The A2 domain of VWF or functional fragments or derivatives thereof may comprise different types of carriers depending on whether it is to be administered in solid, liquid or aerosol form, and whether it need be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990, incorporated herein by reference).

The A2 domain of VWF or functional fragments or derivatives thereof may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the composition is combined with the carrier in any convenient and practical manner, i.e., by solution, suspension, emulsification, admixture, encapsulation, absorption and the like. Such procedures are routine for those skilled in the art.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present disclosure may concern the use of a pharmaceutical lipid vehicle compositions that include A2 domain of VWF or functional fragments or derivatives thereof, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the A2 domain of VWF or functional fragments or derivatives thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a particular dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In particular embodiments of the present disclosure, the A2 domain of VWF or functional fragments or derivatives thereof are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, A2 domain of VWF or functional fragments or derivatives thereof may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound A2 domain of VWF or functional fragments or derivatives thereof may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present disclosure may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

V. Kits of the Disclosure

Any of the compositions described herein may be comprised in a kit. In a non-limiting example, an A2 domain of VWF or functional fragments or derivatives thereof may be comprised in a kit. The kits will thus comprise, in suitable container means, an A2 domain of VWF or functional fragments or derivatives thereof and, optionally, an additional agent, such as a carrier or another pharmaceutical composition, including one or more antibiotics.

The kits may comprise a suitably aliquoted A2 domain of VWF or functional fragments or derivatives thereof of the present disclosure. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the an A2 domain of VWF and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The A2 domain compositions or functional fragments or derivatives thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the disclosure may also comprise, and/or be packaged with, an instrument for assisting with the injection/administration and/or placement of the ultimate an A2 domain or functional fragments or derivatives thereof within the body of an animal. Such an instrument may be a syringe, pipette, forceps, and/or any such medically approved delivery vehicle.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Attenuation of Inflammation-Induced Dic Through Targeting of Fibrin

Disseminated intravascular coagulation (DIC) is common in severe sepsis and plays a central role in the development of organ injuries and multiple organ dysfunction syndrome. Currently, the existing anticoagulation strategies increase the risk of bleeding. In the inventors' previous study, the recombinant A2 domain of human von Willebrand factor (VWF) (called A2 protein) attenuated disseminated microvascular thromboses and markedly decreased mortality in mice, when administered 1.5 hours after lipopolysaccharide (LPS) challenge. This intriguing observation led the inventors to explore the mechanisms by which the candidate biologic can attenuate DIC and improve survival. This study used an A2 mutant protein with defective fibrin binding activity, in vitro assays to study fibrin clot formation and degradation and in vivo mice and porcine models of systemic inflammation associated with DIC including LPS and methicillin-resistant *Staphylococcus aureus* (MRSA), respectively. The A2 protein incorporated into fibrin clots, altered the resultant fibrin clot structure and stability and impacted the clot degradation by plasmin. Fibrin clot structure in healthy and septic human plasma was modified by the addition of A2 protein. In contrast, the A2 mutant protein failed to improve the survival of endotoxemic mice. Flow-dependent platelet adhesion to collagen and experimental thrombosis in mice was not affected by the A2 protein. Importantly, the A2 protein effectively reduced microvascular thromboses, micro-hemorrhages, organ injuries and D-dimer levels in a pre-clinical porcine model of MRSA sepsis. The disclosure concerns a novel treatment to attenuate inflammation-induced DIC through targeting fibrin without an increased risk for bleeding.

Systemic inflammation can lead to coagulopathy and disseminated intravascular coagulation (DIC). In prior studies, the recombinant A2 domain of human von Willebrand factor (VWF; A2 protein) attenuated DIC and decreased mortality in lipopolysaccharide (LPS)-treated mice. The inventors performed studies to dissect the mechanism by which the A2 protein moderates DIC. The inventors used confocal microscopy to analyze the fibrin clot structure in plasma from healthy humans and endotoxemic mice, turbidity assays to examine fibrin polymerization, and a murine model for LPS-induced DIC and introduced a loss-of-function mutation into the A2 protein for fibrin. The mutation of the residue E1567 located in the α2 helix of the folded A2 domain of VWF inhibited binding activity for fibrin, possibly mapping a novel region containing a putative binding site for fibrin. The A2 protein increased the initial rate of change of fibrin polymerization, intercalated into the fibrin network, and modified the resultant clot structure in vitro. Furthermore, ex vivo experiments using plasma from mice with endotoxemia treated with the A2 protein revealed an increased rate of fibrin formation and an altered clot structure as compared with plasma from nontreated sick animals. Moreover, and in contrast to the A2 mutant, the A2 protein improved survival and reduced fibrin deposition and microvascular thrombosis in mice with endotoxemia-induced DIC. Importantly, in vivo and in vitro studies indicated that the A2 protein did not affect experimental thrombosis. Thus, the inventors provide evidence for a novel treatment to attenuate systemic inflammation-induced coagulopathy/DIC via targeting fibrin formation (FIG. 21), without an increased risk for bleeding.

Example 2

Examples of Materials and Methods

Animal Studies: All studies were conducted in accordance with the National Institutes of Health's Guide for the Care and Use of Laboratory Animals and approved by the institutional animal care and use committees of BAYLOR COLLEGE OF MEDICINE®.

Reagents: The loss-of-function A2 mutant was constructed by introducing the E1567A mutation into the vector pQE-9/VWF-A2 using the a site-directed mutagenesis kit (e.g., QUIKCHANGE® II XL by STRATAGENE®, CA). The mutation was introduced by PCR using the following primers harboring the mutation (5' primer-GCAGCGGGTGCGAGCGATCCGCTACCAGG (SEQ ID NO:19), and 3' primer-CCTGGTAGCG-GATCGCTCGCACCCGCTGC; SEQ ID NO:20). The recombinant A2 E1567A mutant was identically purified to wild-type (WT) A2 protein. More details on the characterization of the A2-fibrin interaction and the analyses of the A2 mutant are in supplemental methods. Purified recombinant proteins (WT A2 and A2 E1567A mutant) were confirmed and validated as described.[3] Structural integrity of the purified proteins was assessed by using the monoclonal anti-A2 antibody and circular dichroism thermal unfolding as described.[4] Human fibrinogen was obtained from CALBIOCHEM®, and the recombinant human vimentin and monoclonal anti-human VWF-A2 domain (anti-A2) antibody were purchased from R&D SYSTEMS®. The LPS (0111:B4) and antihistidine-horseradish peroxidase (HRP) conjugate antibody were obtained from SIGMA-ALDRICH®. The recombinant A1 domain protein was produced as described previously.[1,2]

Imaging the fibrin-clot structure: To obtain blood informed consent was provided according to the recommendations of the Declaration of Helsinki. Approval was attained from the BAYLOR COLLEGE OF MEDICINE® institutional review board (IRB) for these studies. The effect of the A2 protein on fibrin-clot structure was evaluated using platelet poor plasma (PPP) collected from human subjects and septic pediatrics patients under an IRB approved protocol. Three-dimensional reconstructions of the fibrin-clot structure were obtained by supplementing the plasma with 2% (w/w) of human fibrinogen conjugated to fluorescent antibodies in the 647 spectral range (e.g., ALEXA FLUOR® 647; THERMO SCIENTIFIC™) and initiating clot formation with the addition of 1 U thrombin (EMD MILLIPORE™) in the presence of 2.4 mM calcium. In studies with endotoxemic murine plasma, the A2 protein was injected intraperitoneally (IP) in vivo. Murine platelet-poor plasma was supplemented with 4% (WT/WT) human fibrinogen conjugated to fluorescent antibodies in the 647 spectral range (e.g., ALEXA FLUOR® 647) and clot formation initiated with 4 U of thrombin. In both instances, the plasma was transferred to a 35-mm glass-bottom dish (MATTEK™) and incubated at 37° C. for 2 hours to allow clot formation, which was then imaged by laser scanning confocal microscopy. In some experiments, the A2 protein was fluorescently labeled through conjugation of the protein to fluorescent antibodies in the 488 spectral range (e.g., ALEXA FLUOR® 488; THERMO SCIENTIFIC™). In these studies, the proteins were added and mixed with the whole blood before initiation of clot formation with the addition of thrombin. The whole blood was transferred to a 35-mm glass-bottom dish (MATTEK™) and incubated at 37° C. for 2 hours to allow the clot to form. The whole blood was first fixed overnight and cleared using the c-clot protocol as previously described,[10] before being imaged by laser scanning confocal microscopy.

Fibrinolysis Assays: Fibrinolysis was evaluated by turbidity. In short, the WT A2 protein or the A2 mutant (4.0 μM) were incubated with 1 mg/mL of human fibrinogen, and plasminogen (SIGMA-ALDRICH®) in the presence of 150 ng/mL of tissue plasminogen activator (tPA) (CATHFLO® ACTIVASE®) and 0.1 U of human thrombin. The progression of fibrin-clot formation and fibrinolysis was evaluated by tracking turbidity using a spectrophotometer set to A 405 nm.

Fibrin Polymerization Assays: Fibrin formation was evaluated by turbidity assay using healthy human plasma or endotoxemic plasma as described.[2] The progression of fibrin clot formation was evaluated by tracking turbidity using a spectrophotometer set to $\lambda$ 405 nm. Fibrinolysis was performed by mixing human healthy plasma with the A2 protein (2.0 or 4.0 μM) or saline in the presence of 150 ng/mL of tissue plasminogen activator (CATHFLO® ACTIVASE®) and 0.1 U of human thrombin. The progression of fibrin clot formation and fibrinolysis was evaluated by tracking turbidity using a spectrophotometer set to $\lambda$ 405 nm.

Rotational Thromboelastometry (e.g., ROTEM®) was used to determine the maximum lysis (ML) percentage whole blood in the presence of the A2 protein. Citrated blood was collected from 2 healthy donors and EXTEM (testing extrinsic hemostasis via tissue factor) was performed in the presence of the A2 protein (4 μM) or TBST vehicle, and 350 ng/mL of tPA.

Antibodies and Reagents: Human fibrinogen was obtained from CALBIOCHEM®, while the recombinant human vimentin and monoclonal anti-human VWF-A2 domain (anti-A2) antibody were purchased from R&D SYSTEMS®. The LPS (0111:B4), and anti-histidine-horseradish peroxidase conjugate antibody were obtained from SIGMA-ALDRICH®. Both recombinant A1 and A2 domain proteins were produced as described previously[1,2]. Purified recombinant proteins (WT A2 and A2 (E1567A) mutant) were confirmed and validated as described 3. Structural integrity of the purified proteins was assessed by using the monoclonal anti-A2 antibody and circular dichroism (CD) thermal unfolding as described[4].

Binding Assays: The binding of WT A2 and A2 E1567A mutant to fibrin, vimentin, and A1 domain protein were performed using enzyme-linked immunosorbent assay (ELISA) as was previously described[2,5,6]. To convert fibrinogen to fibrin, 0.1 U/ml of Thrombin (SIGMA-ALDRICH®) was incubated in wells coated with fibrinogen (5.0 μg/ml) for 45 min at 37° C. Following incubation and washing, increasing concentrations of the A2 variants were added onto the wells. The bound proteins were detected using monoclonal anti-histidine-horseradish peroxidase (HRP) conjugate. Anti-A2 antibody was used to detect A2 variants bound to either vimentin or A1 domain protein followed by a secondary HRP conjugate antibody.

SPOT synthesis of the A2 peptide sequence: SPOT synthesis was employed to identify key residues within A2 protein that are important for fibrin binding[7]. While the entire A2 sequence was evaluated, overlapping peptide sequences of 18 residues in length were synthesized on cellulose membranes by automated SPOT synthesis using a peptide synthesizer (e.g., MultiPep RS, Intavis, Bergisch Gladback, Germany) as described elsewhere[8]. Following synthesis, the membranes were soaked for 10 min in methanol, followed by two, 10 min washes in phosphate buffer saline (PBS, pH—7.4) before incubation in blocking buffer overnight at 4° C. with gentle rocking. The following day, the membrane was washed three times for 10 min each with PBS, 0.05% polysorbate 20 (e.g., TWEEN®) 20 (PBS-T), 1% bovine serum albumin (BSA). Fibrin (SIGMA-AL-DRICH®) was biotinylated and dialyzed against PBS. The biotinylated fibrin was diluted to a concentration of 75 µg/ml in PBS-T, 1% BSA and incubated with the membrane for 2 hours with gentle shaking at room temperature. Following the incubation, the membrane was washed three times with PBS-T, 1% BSA, 10 min each and incubated with avidin-HRP diluted in PBS-T, 1% BSA for 1 hour at room temperature with gentle shaking. The membrane was washed three time with PBS-T, 1% BSA and developed with a chemiluminescent substrate (e.g., SUPERSIGNAL® West Pico; THERMO SCIENTIFIC™) for 1 min and then exposed to autoradiography film. The key residues were identified as described[9], and the three-dimensional structure representation created using UCSF Chimera software.

Imaging the fibrin-clot structure: Clots were formed in the presence and absence of the A2 protein and then mixed with the human plasma prior to the addition of thrombin. With respect to the septic porcine plasma, the A2 protein was infused directly into the animal's circulation in vivo. The pig plasma was supplemented with 4% (w/w) human fibrinogen conjugated to fluorescent antibodies in the 647 spectral range (e.g., ALEXA FLUOR® 647) and clot formation initiated with 4 U thrombin. In both instances, the plasma was transferred to a 35 mm glass bottom dish (MATTEK™) and incubated at 37° C. to allow the clot to form prior to being imaged by laser scanning confocal microscopy (LSCM).

The effect of the A2 protein on fibrin-clot structure was evaluated using whole blood collected from healthy human subjects. Three-dimensional reconstructions of the fibrin-clot structure were obtained by supplementing the whole blood with 1% (w/w) of human fibrinogen conjugated to fluorescent antibodies in the 647 spectral range (e.g., ALEXA FLUOR® 647) and initiating clot formation with the addition of 1 U thrombin in the presence of 2.4 mM calcium. In some experiments, the A2 protein was fluorescently labeled through conjugation of the protein to fluorescent antibodies in the 488 spectral range (e.g., ALEXA FLUOR® 488; THERMO SCIENTIFIC™). In these instances, the protein was added and mixed with the whole blood prior to initiation of clot formation with the addition of thrombin. The whole blood was transferred to a 35 mm glass bottom dish (MATTEK™) and incubated at 37° C. for two hours to allow the clot to form. The whole blood was first fixed overnight and cleared using the c-clot protocol as previously described 10, prior to being imaged by LSCM.

Western blot: The formation of fibrin degradation products were examined via Western blot using samples from tPA-lysed in-vitro generated clots (see Fibrinolysis Assays above). The resulting lysed clot sample was run on an SDS-PAGE gel and transferred to a PVDF membrane. The presence of high molecular weight FDPs, including D fragment, were determined by probing the PVDF membrane with a mouse monoclonal primary antibody (Santa Cruz), followed by a goat anti-mouse antibody conjugated to horse radish peroxide which was exposed to an enhanced chemiluminescence substrate (THERMO FISHER®).

Flow Assays: The Bioflux perfusion system (Fluxion Biosciences) was utilized to examine the influence of the A2 protein on platelet adhesion to collagen. Plates were coated with purified human collagen type III at a concentration of 50 µg/mL[5]. Whole blood collected from two healthy donors was supplemented with 8% (w/w) of human fibrinogen conjugated to fluorescent antibodies in the 647 spectral range (e.g., ALEXA FLUOR® 647) and treated with either vehicle control or the WT A2 protein at a concentration of 4 µM. The blood was perfused at 60 dyn/cm² for 10 mins and the platelet/fibrin deposition tracked as previously described[11]. In other experiments, dishes were coated with collagen Type III and perfused with whole blood from healthy donors containing vehicle control buffer or WT A2 protein (4 µM). Perfusion assays were carried out as was described elsewhere[5]. Platelets were observed with phase contrast objectives, recorded by video-microscopy, and analyzed by using the MacBiophotonics ImageJ program.

Intravital microscopy: Preparation of the cremaster muscle of male C57Bl/6J mice (n=16), photoactivation to induce thrombosis and analyses were performed as described by the inventors' group[12,13]. Briefly, after equilibration, fluorescein isothiocyanate-dextran (150 kD; 10 mL/kg of a 5% solution) was injected via the venous catheter and allowed to circulate for ~10 minutes. Thereafter, venular diameter was measured (ImageJ 1.6; National Institutes of Health public domain software) as well as mean blood cell velocity (Vdoppler, using an optical Doppler velocimeter; Cardiovascular Research Institute, Texas A&M University). Venular wall shear rate (γ) was calculated as 8 (Vdoppler/1.34)/diameter. After those measurements, light/dye-induced injury was begun by exposing ~100 µm of vessel length to epiillumination, with a 175-W xenon lamp (Λ LS; SUTTER®, Novato, CA) and a fluorescein filter cube (HQ-FITC; CHROMA®, Bellows Falls, VT). Excitation light was monitored daily (IL 1700 Radiometer, SED-033 Detector; International Light, Peabody, MA) and maintained at 0.6 W/cm². Epiillumination was applied continuously, and the following times were recorded: time of onset of platelet aggregates and time of flow cessation, for at least 60 seconds. Five minutes before thrombus induction, animals received a single IV bolus of the A2 protein at a dosage of 4 mg/kg (n=8). Control animals received equivalent volumes of physiological saline (n=8).

LPS-induced DIC murine model and histology: Briefly,[2] mice (C57BL/6, 10-12 weeks old) were injected intraperitoneally (i.p.) with LPS (30 mg/kg). The WT A2 (n=10) or A2 E1567A (n=12) mutant or saline (n=6) was injected i.p. at a concentration of (4 mg/kg) 1.5 hour after the LPS injection. Saline was used as positive control. Mice that do not receive either injections were used as negative controls. At 24 hours after LPS injection, kidneys were harvested from mice. These organs were processed using the services of the Comparative Pathology Laboratory of BAYLOR COLLEGE OF MEDICINE®. Microvascular fibrin-rich thrombi in paraffin embedded kidney tissues were studied by immunostaining using the polyclonal fibrinogen antibody (DAKO®, Carpinteria CA). Histology images were analyzed using Olympus FV3000 Microscope.

Pig Anesthesia and Surgery: All animal procedures were carried out following the protocols approved by the Institutional Animal Care and Use Committee of BAYLOR COLLEGE OF MEDICINE®. Five-week old domestic pigs (male and female divided equally in each experimental group) were inoculated intravenously via an internal jugular vein with MRSA. In other experiments sham pigs underwent all procedures and blood draws minus MRSA inoculation. Four days prior to MRSA inoculation, all pigs underwent general anesthesia to have a telemetry device cannulated in the right femoral artery, a central venous line cannulated in the right internal jugular vein, and an arterial catheter cannulated in the right carotid artery (catheter inner diameter=1 mm, and outer diameter=1.7 mm). A surgical implantable PHYSIOTEL™ Digital Blood Pressure and Biopotential Telemetry Device made by DATA SCIENCES INTERNATIONAL™, Minnesota, USA was used. For anesthesia during the procedure, the pigs were induced and maintained with 1-2% isoflurane by face mask. Buprenorphine subcutaneously was used for acute pain. Vital signs were monitored including respiration rate, heart rate, oxygen saturation and temperature throughout the procedure. After the surgery, the pigs were observed for 4 days to obtain baseline temperature, heart rate, and blood pressure from the telemetry device.

MRSA: A MRSA strain was used (USA300-HOU-MR-TCH 1516) that was isolated from a previously critically ill septic patient at TEXAS CHILDREN'S HOSPITAL® (TCH) in Houston[14]. The pigs were inoculated with USA300-HOU-MR-TCH 1516 intravenously via an internal jugular central venous catheter over 5 minutes with a dose of $1 \times 10^9$ colony forming units (CFU)/kg of body weight at a concentration of $1 \times 10^9$ CFU/ml. The Pig-ICU was staffed 24/7 with either an intensivist, veterinarian, or research scientist.

Neurologic and Respiratory Scores: A published porcine neurologic examination score[15] was modified and a respiratory examination score was added. The pigs were examined and the neurologic and respiratory scores were recorded before MRSA inoculation and every 6 hours after MRSA inoculation.

Fluids Resuscitation for Septic Shock and Other Clinical Managements: Pigs were resuscitated with normal saline boluses (10 mL/kg) when heart rate was >50% or mean arterial blood pressure was <30% from established individual baseline. Intravenous acetaminophen at a dose of 15 mg/kg was given as needed every 6 hours when the pigs' temperature was >41° Celsius) for more than 1 hour. Maintenance intravenous fluid composed of 5% dextrose in normal saline was given when the pigs were no longer willing eat independently. Blood sugar (DATA SCIENCES INTERNATIONAL™) and arterial blood gas (ABG) (VETSCAN I-STAT® 1, California, USA) were measured with scheduled blood draws or when dictated by clinical signs and symptoms.

Euthanasia and Immunohistochemistry: Criteria for early euthanasia were severe acute respiratory distress, unresponsiveness to stimuli, and refractory to fluid resuscitation. The pigs were euthanized 70 h after MRSA administration by injecting a commercial mixture of phenytoin and pentobarbital (Beuthanasia D, MERCK®). Subsequently, brain, heart, lung, kidney and liver tissues were harvested for analysis. Tissues were fixed in either 10% or 20% neutral buffered formalin prior to processing, paraffin embedding.

Tissue sections were sectioned into 5 μm followed by hematoxylin and eosin (H&E) staining to evaluate tissues for microthrombi and organ injuries. Tissue slides were independently reviewed by a staff pathologist and a research scientist.

Histological Organ Injury Scores: Two independently blinded investigators, a pathologist and a research scientist, qualitatively assess the severity of micro-thrombi, micro-hemorrhages, and lymphocyte foci from H&E stained slides. The qualitative scores were recorded as 0 for normal up to 3 or 4 for the worst pathology.

Pigs treated with A2 protein: Pigs were prepared as described above. The MRSA-septic pigs were treated with the A2 protein 12 or 24 h after the MRSA inoculation using three different doses (1.0, 2.0, and 1.75 mg/kg) or with saline. The protein or saline was administered (i.v. catheter) with a syringe pump at an infusion rate of 10.0 mL/h for 6 h. A subset of pigs received a second dose of A2 protein (1.75 mg/kg) or saline 48 h after MRSA inoculation. All the pigs received the same care as described above and were euthanized at 70 h.

Statistics: Prism by GraphPad Prism 8 Software, California, USA and SIGMAPLOT® by SYSTAT® Software Inc., California, USA were used to perform statistical analyses including 2-Factor Repeated Measures Analysis of Variance (2F-RM-ANOVA), non-linear fit regression and t-test. $P < 0.05$ was considered statistically significant.

REFERENCES FOR THE EXAMPLES OF MATERIALS AND METHODS IMMEDIATELY ABOVE

1. Auton M, Sow K E, Smith S M, Sedlak E, Vijayan K V, Cruz M A. Destabilization of the A1 domain in von Willebrand factor dissociates the A1A2A3 tri-domain and provokes spontaneous binding to glycoprotein Ibalpha and platelet activation under shear stress. J Biol Chem. 2010; 285(30):22831-22839.
2. Nguyen T C, Gushiken F, Correa J I, et al. A recombinant fragment of von Willebrand factor reduces fibrin-rich microthrombi formation in mice with endotoxemia. Thromb Res. 2015; 135(5):1025-1030.
3. Cruz M A, Whitelock J, Dong J F. Evaluation of ADAMTS-13 activity in plasma using recombinant von Willebrand Factor A2 domain polypeptide as substrate. Thromb Haemost. 2003; 90(6):1204-1209.
4. Auton M, Cruz M A, Moake J. Conformational stability and domain unfolding of the Von Willebrand factor A domains. J Mol Biol. 2007; 366(3):986-1000.
5. Da Q, Behymer M, Correa J I, Vijayan K V, Cruz M A. Platelet adhesion involves a novel interaction between vimentin and von Willebrand factor under high shear stress. Blood. 2014; 123(17):2715-2721.
6. Martin C, Morales L D, Cruz M A. Purified A2 domain of von Willebrand factor binds to the active conformation of von Willebrand factor and blocks the interaction with platelet glycoprotein Ibalpha. J Thromb Haemost. 2007; 5(7):1363-1370.
7. Cushman I, Palzkill T, Moore M S. Using peptide arrays to define nuclear carrier binding sites on nucleoporins. Methods. 2006; 39(4):329-341.
8. Frank R. The SPOT-synthesis technique. Synthetic peptide arrays on membrane supports—principles and applications. J Immunol Methods. 2002; 267(1):13-26.
9. Cushman I. Utilizing peptide SPOT arrays to identify protein interactions. Curr Protoc Protein Sci. 2008; Chapter 18:Unit 18.10.

10. Hook P, Brito-Robinson T, Kim O, et al. Whole blood clot optical clearing for nondestructive 3D imaging and quantitative analysis. Biomed Opt Express. 2017; 8(8): 3671-3686.

11. Da Q, Teruya M, Guchhait P, Teruya J, Olson J S, Cruz M A. Free hemoglobin increases von Willebrand factor-mediated platelet adhesion in vitro: implications for circulatory devices. Blood. 2015; 126(20):2338-2341.

12. Patel K N, Soubra S H, Lam F W, Rodriguez M A, Rumbaut R E. Polymicrobial sepsis and endotoxemia promote microvascular thrombosis via distinct mechanisms. J Thromb Haemost. 2010.

13. Rumbaut R E, Bellera R V, Randhawa J K, et al. Endotoxin enhances microvascular thrombosis in mouse cremaster venules via a TLR4-dependent, neutrophil-independent mechanism. Am J Physiol Heart Circ Physiol. 2006; 290(4):H1671-H1679.

14. Highlander S K, Hulten K G, Qin X, et al. Subtle genetic changes enhance virulence of methicillin resistant and sensitive *Staphylococcus aureus*. BMC Microbiol. 2007; 7:99.

15. Rhee P, Talon E, Eifert S, et al. Induced hypothermia during emergency department thoracotomy: an animal model. J Trauma. 2000; 48(3):439-447; discussion 447-450.

Example 3

Figure 1A:
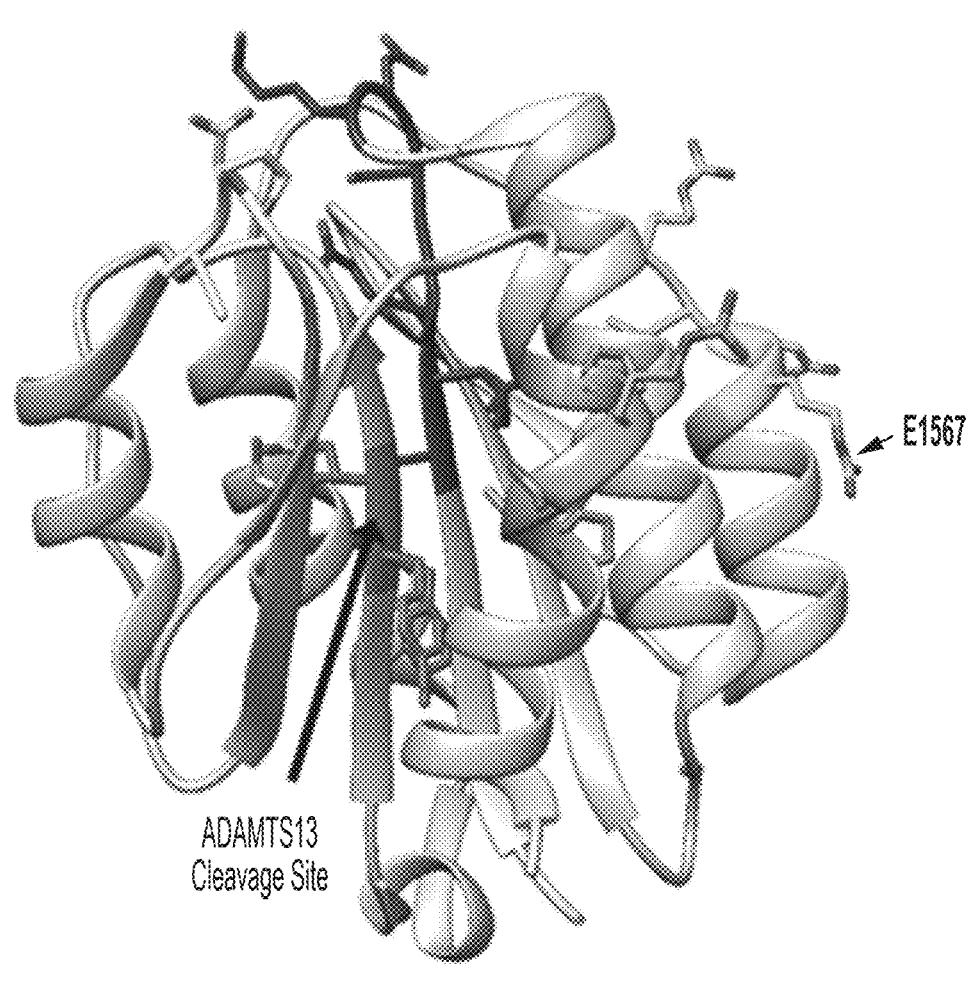
FIGS. 1A-1F. Characterization of the A2 protein-fibrin interaction.
Figure 1B:
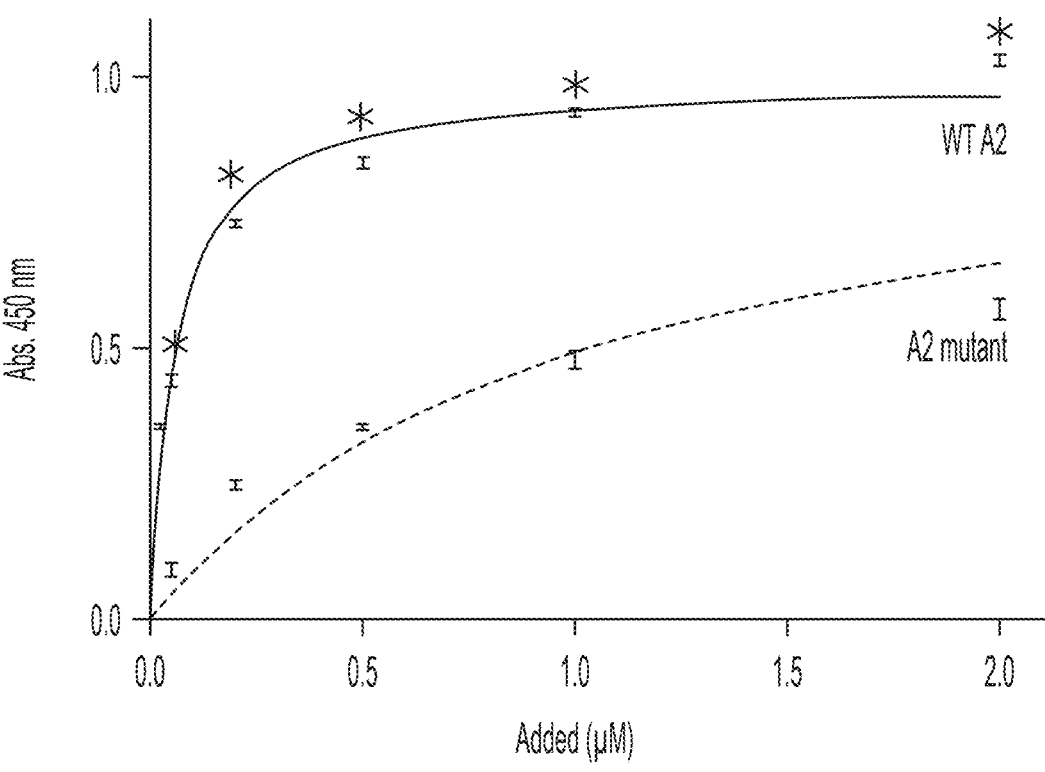
Figure 1C:
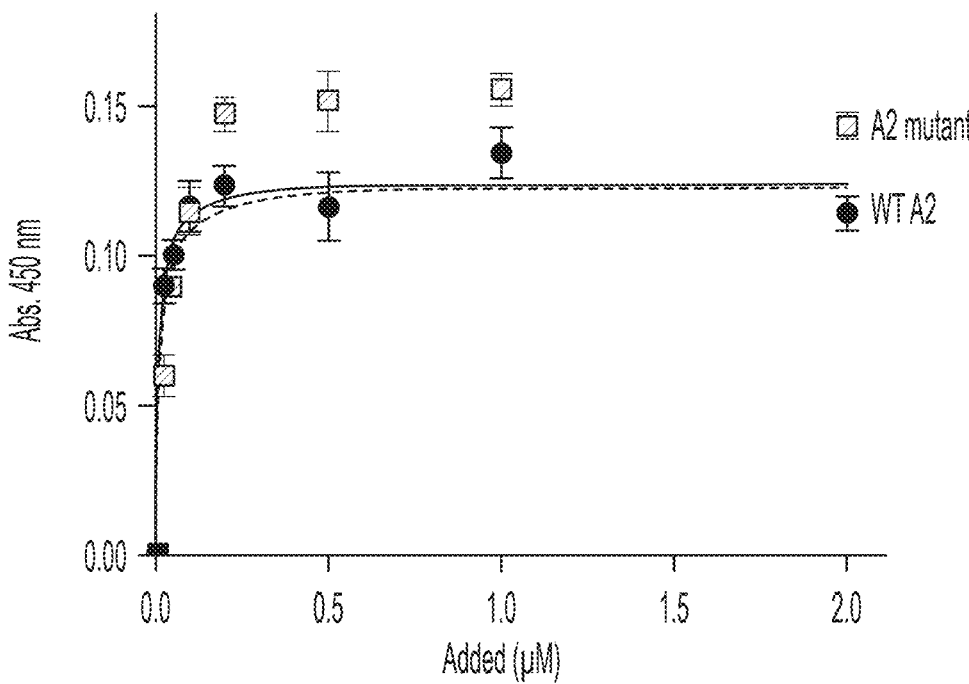
Figure 1D:
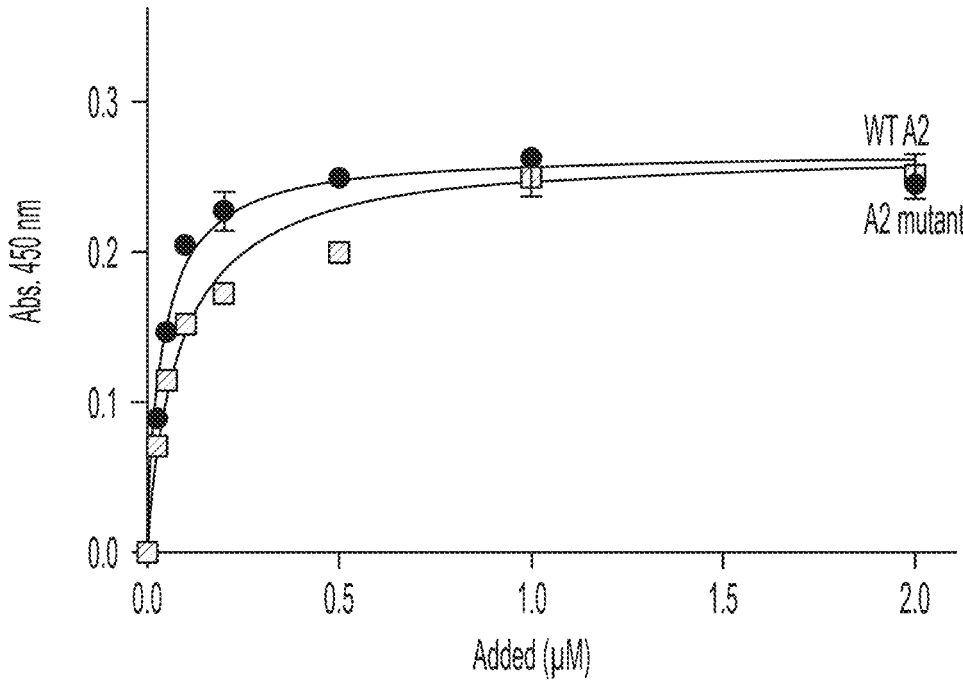
Figure 1E:
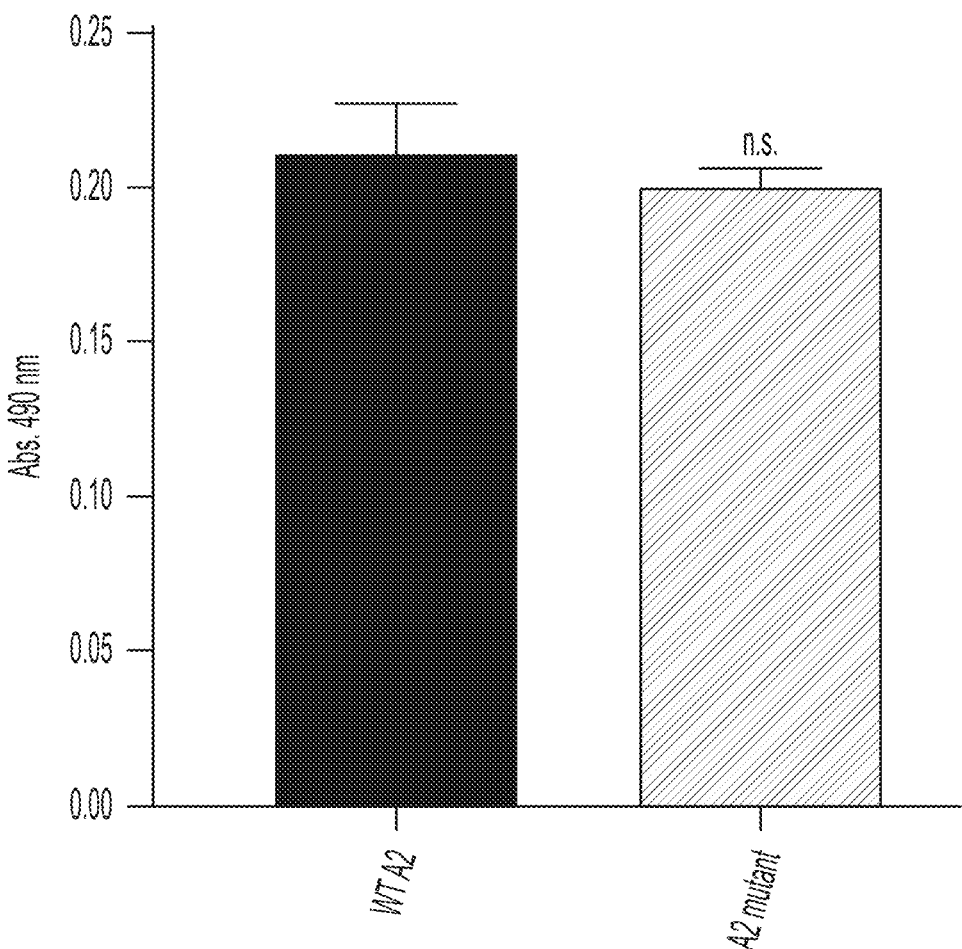
Figure 1F:
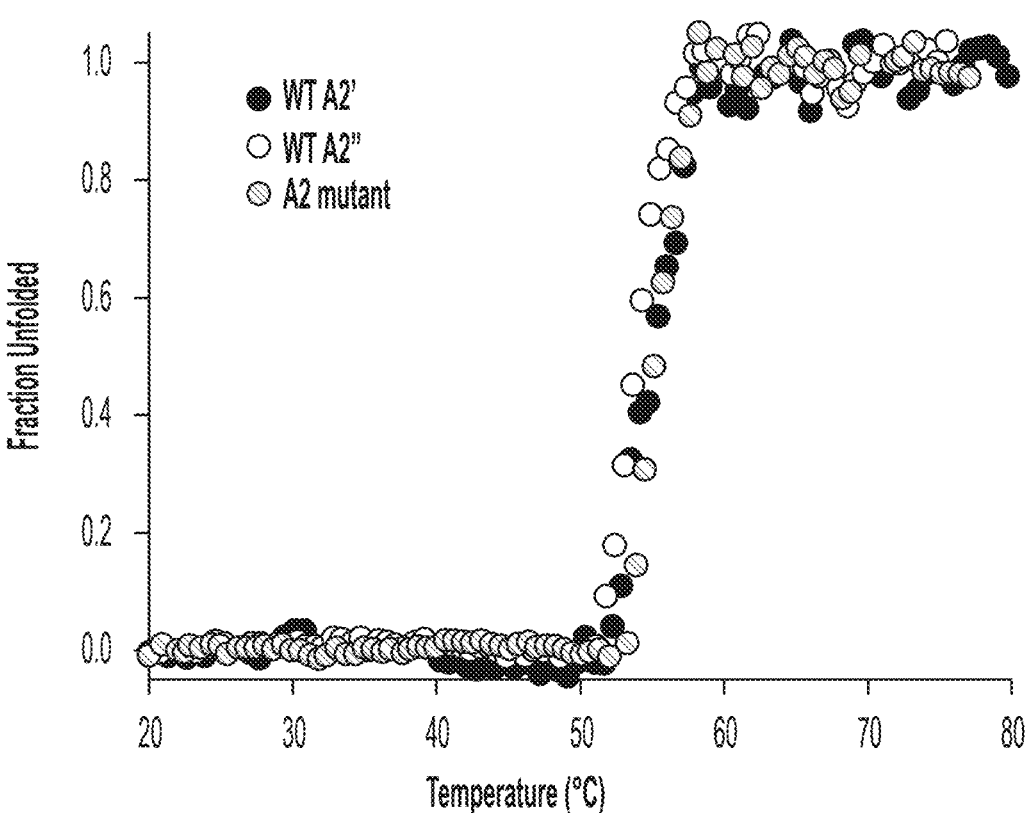
Figure 8:
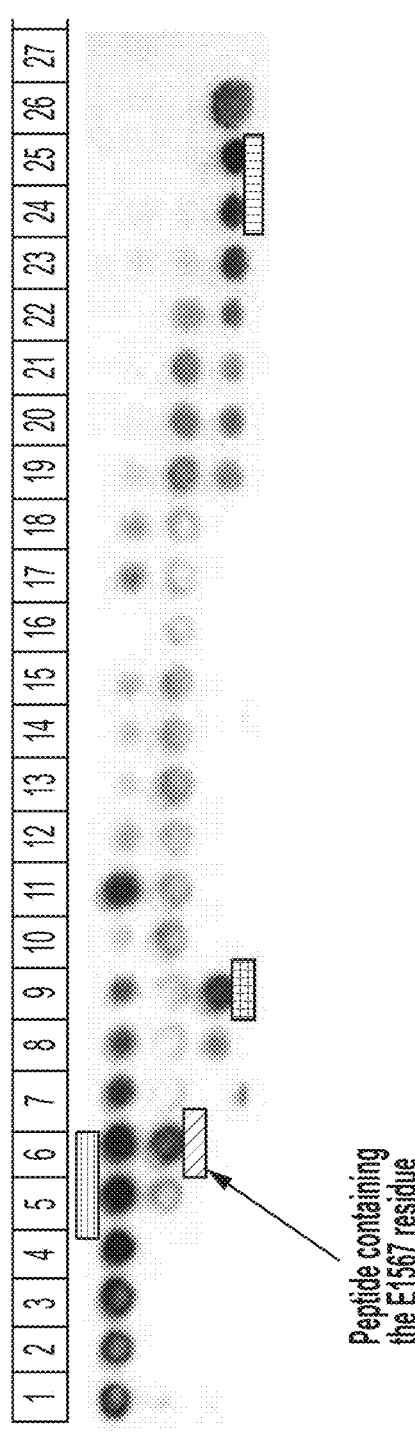
FIG. 8. Interaction of fibrin with the A2 protein using peptide spot array. The biotinylated fibrin bound to cellulose-bound peptide array was detected with avidin-HRP. The spots were analyzed using densitometry. The high intensity spots are marked with textured bars representing putative binding sites for fibrin.
Figure 9:
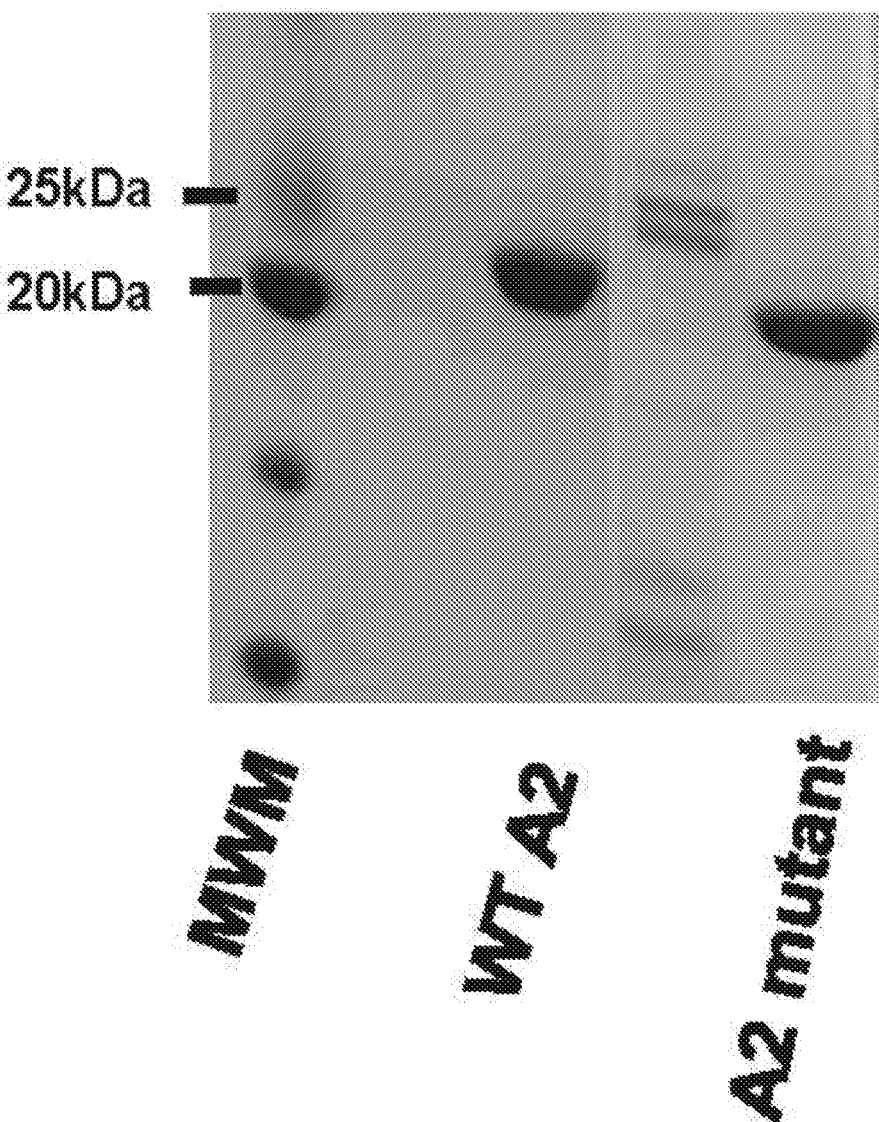
FIG. 9. Coomasie Blue stained SDS-PAGE showing the purified WT A2 protein and A2 (E1567A) mutant under reduced conditions.

Targeting Fibrin Attenuates Microvascular Thrombosis and Organ Injuries in Multiple Models of Systemic Inflammation The A2 Protein Exerts its Beneficial Effect Via Binding to Fibrin Since the A2 protein impacts fibrin formation[13], it was contemplated that A2 mutants with defective binding activity for only fibrin but not for other A2 ligands can help dissect the mechanism by which the A2 protein attenuates microvascular thrombosis in vivo. The crystal structure of the A2 domain was used as a guide in the selection of solvent exposed amino acid residues (usually contribute to the interaction with proteins) to introduce point mutations. In parallel, the peptide SPOT array technique[14] was used to identify the putative contact site for fibrin within the A2 domain structure. To this end, 18 meric overlapping peptides derived from the amino acid sequence of the A2 domain (G1481-R1668) were directly synthesized on a cellulose membrane and probed for binding to fibrin (FIG. 8). After analyzing the intensity of the binding spots, the resultant residues were mapped onto the crystal structure of the A2 domain[15]. The regions α2-helix and α6-helix most likely form the putative contact site(s) for fibrin, although the β1-strand could contribute if the A2 protein is unfolded prior to the binding to fibrin (FIG. 1A). Among the A2 mutants constructed, the purified A2 (E1567A) mutant (FIG. 9) exhibited a much lower binding affinity for fibrin than that of the WT A2 protein (half maximal binding constant of $1.03\pm0.079$ μM vs. $0.06\pm0.004$ M, respectively, FIG. 1B). Note that the peptide sequence containing the amino acid residue E1567 on the cellulose membrane was readily detected by fibrin (FIG. 1 and FIG. 8). Importantly, the A2 mutant bound to both recombinant A1 domain of VWF (FIG. 1C) and vimentin (FIG. 1D) comparably to that of the WT A2 protein. The E1567A mutation did not alter the overall structure of the A2 domain as demonstrated by studies employing monoclonal antibody (FIG. 1E) and circular dichroism (CD) thermal unfolding (FIG. 1F). Thus, the E1567A mutation specifically impaired the interaction of the A2 protein with fibrin without altering the binding affinity for both the A1 domain of VWF and vimentin.

Figure 2A:
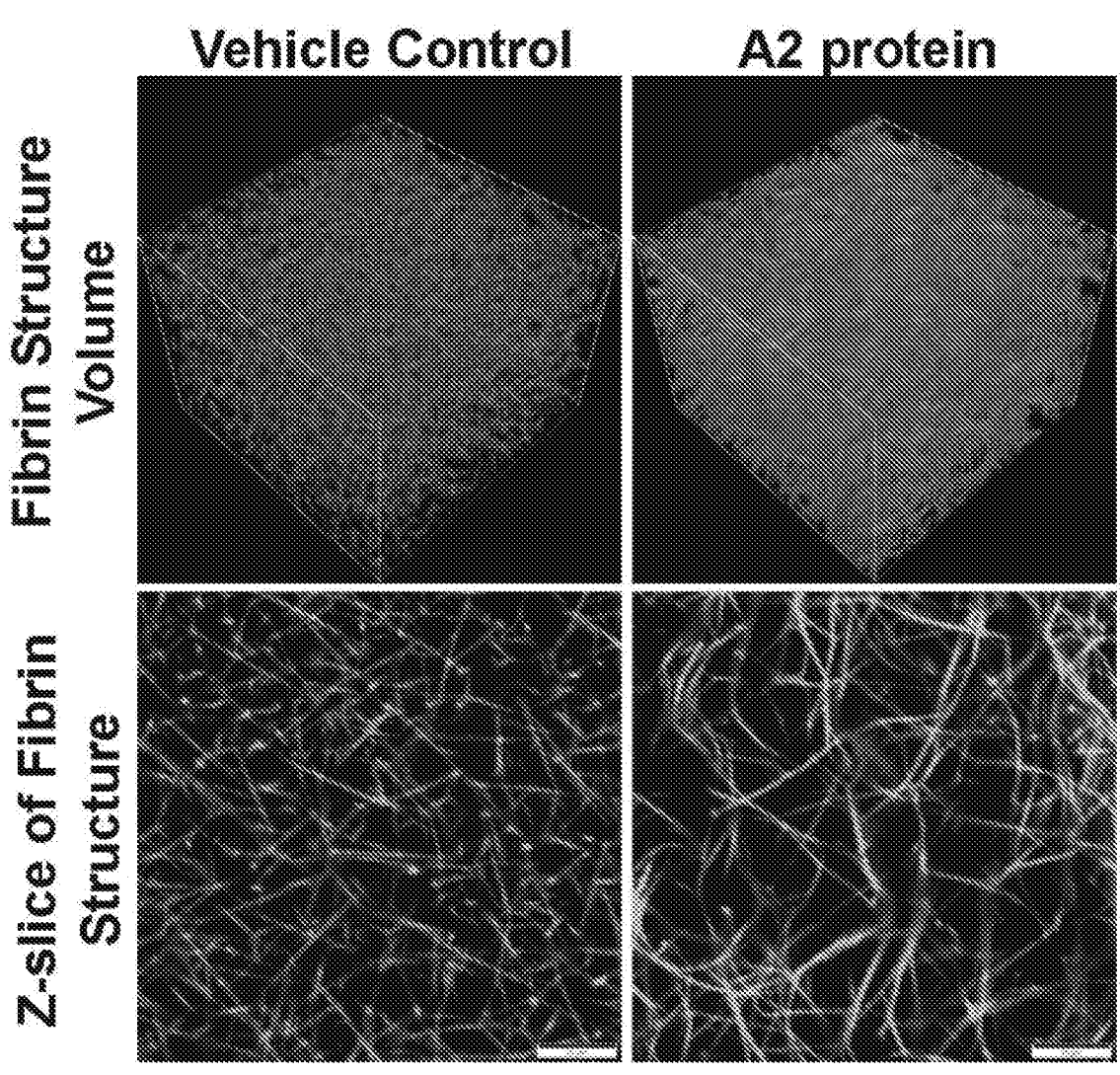
Figure 2B:
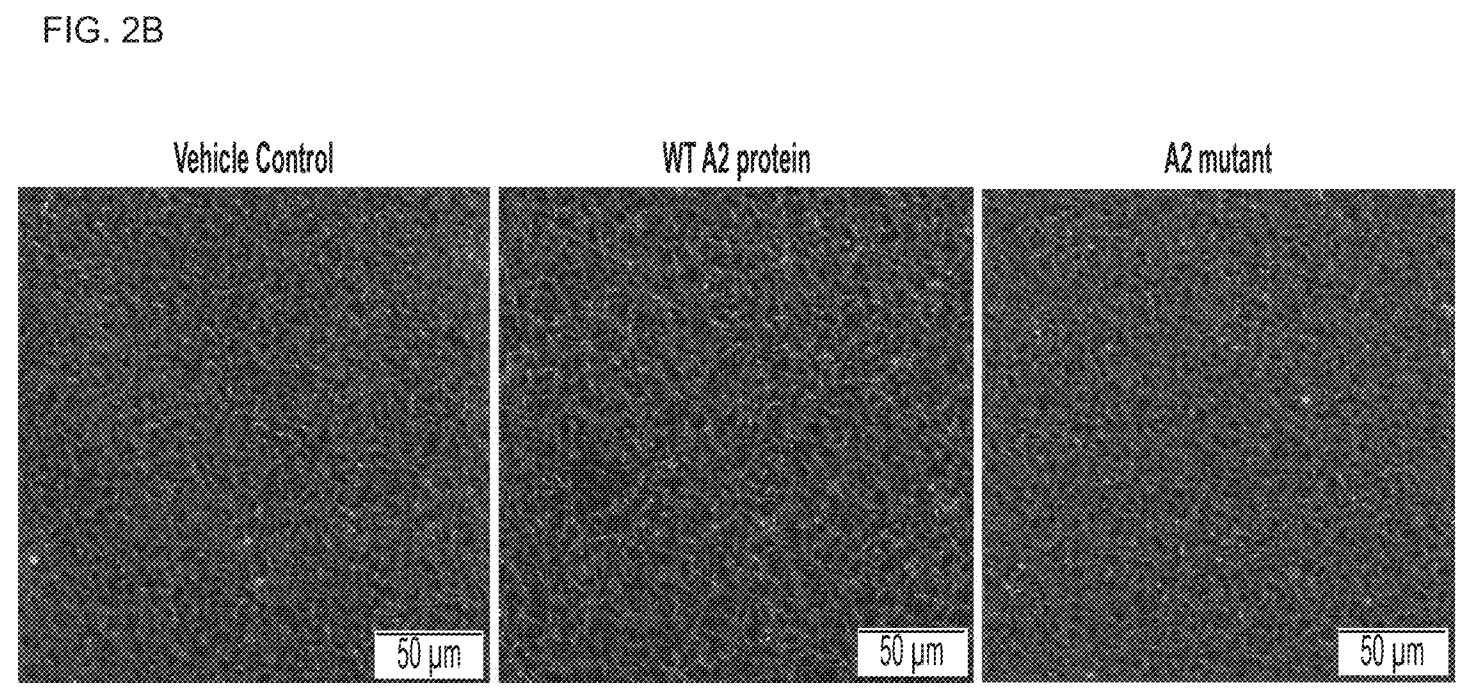
Figure 2C:
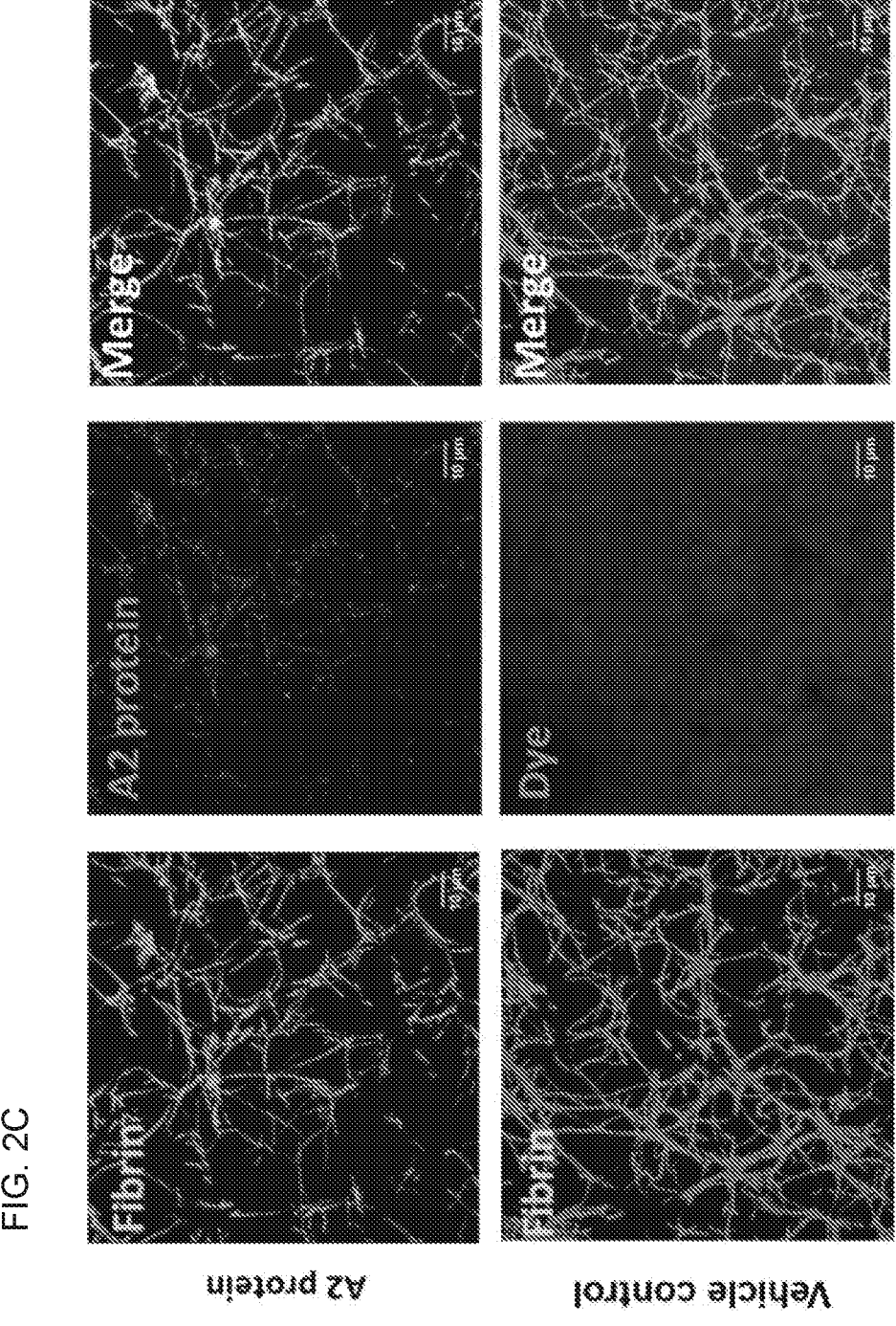
Figure 2D:
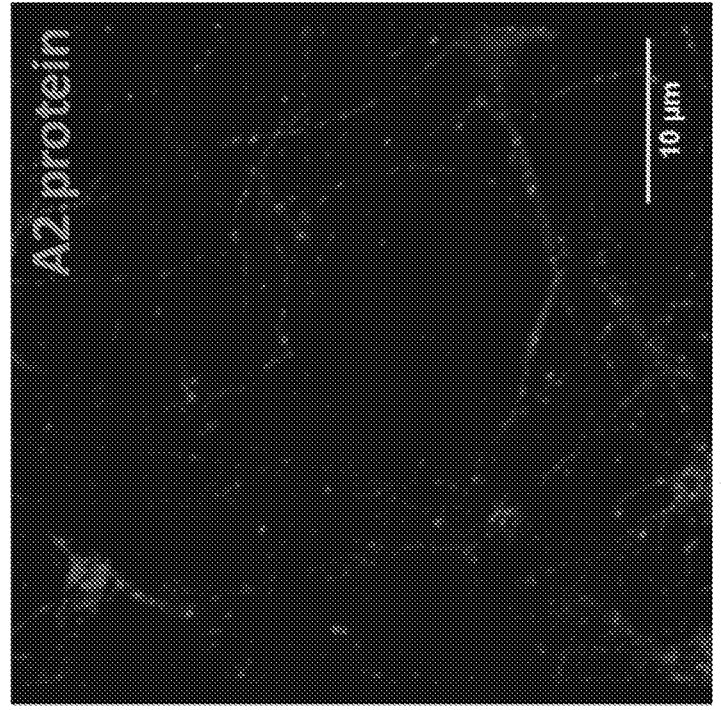
Figure 2D:
Figure 10A:
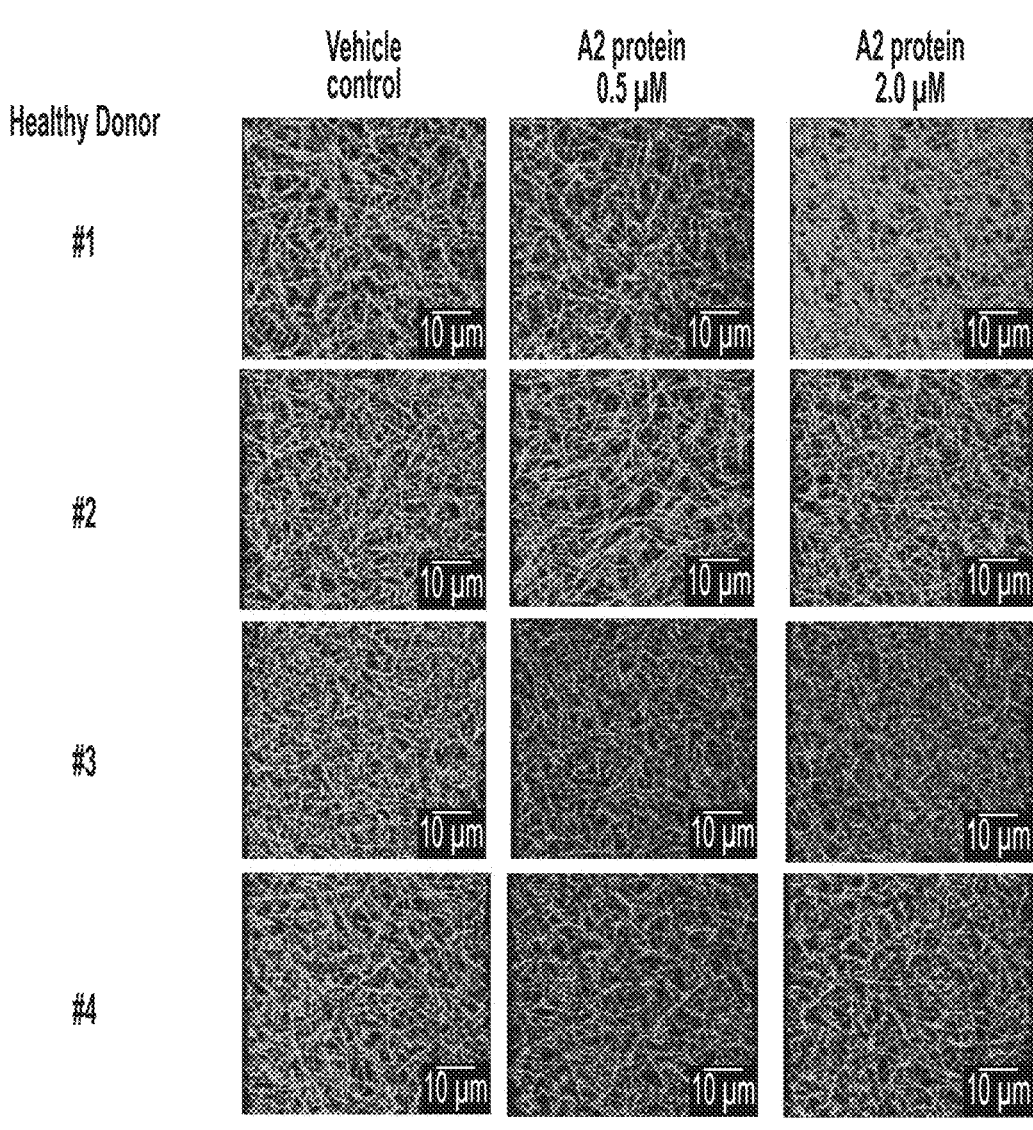
FIGS. 10A-10B.
Figure 10B:
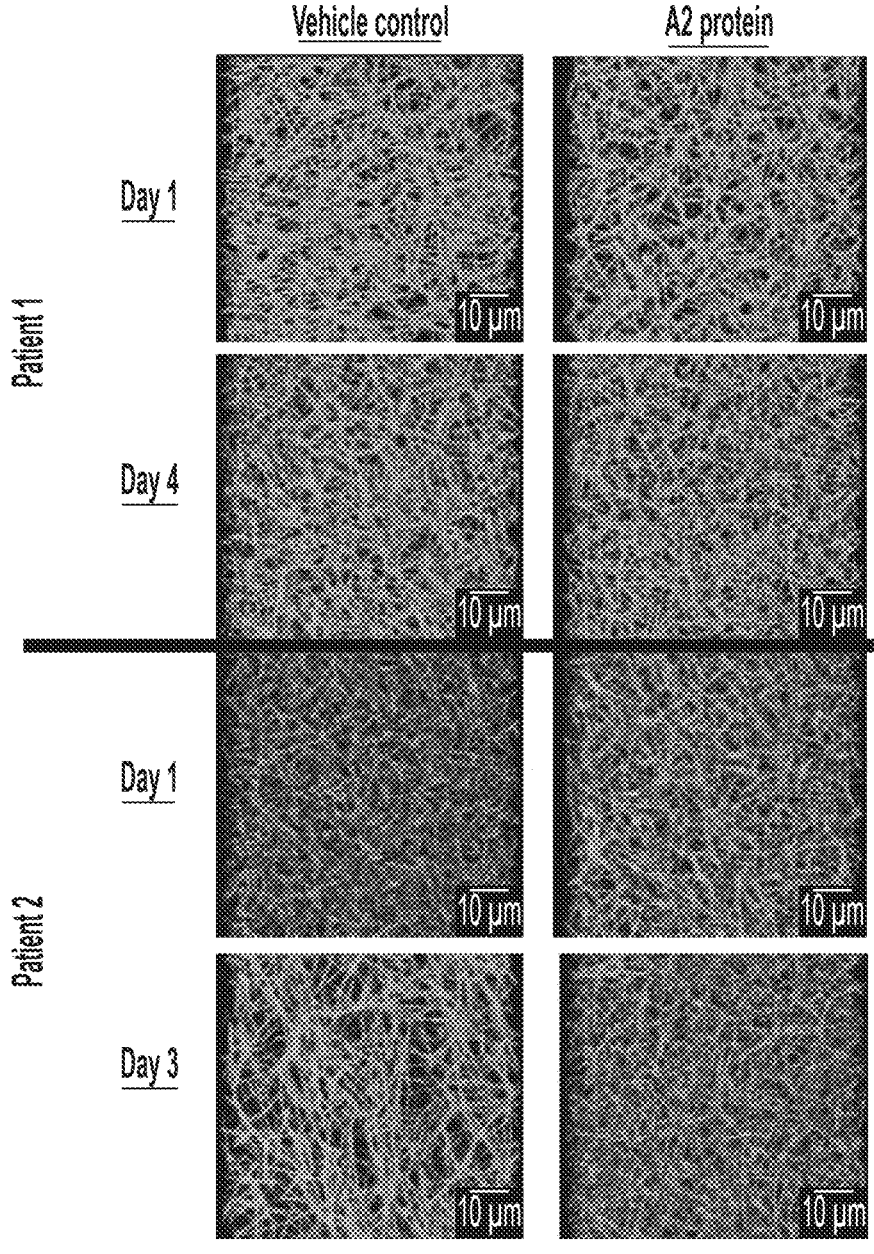

Next, the effect was examined of the A2 protein on polymerized fibrin structure using confocal microscopy. FIG. 2A shows representative images of fibrin structure formed in plasma from healthy human donors. Note the considerable variation of the fibrin network structure with A2 protein (right column) compared to that incubated with vehicle control (left column). Moreover, FIG. 2A shows that the three-dimensional reconstruction of fibrin formed in the presence of the A2 protein (top right panel) demonstrated fluorescence intensity higher than that of vehicle control (top left panel), giving the impression to be denser than the control clot. Z-stack representative images show that the A2 protein apparently provoked the formation of larger pores in the resultant formed clot (lower right panel) in comparison to vehicle control (lower left panel). Additional experiments were performed using plasma from healthy human donors and differences in the resultant fibrin clot structures were evident, however, the effect of the A2 protein was distinguishable (FIG. 10A). Similar approach was utilized to assess the effect of the A2 mutant (E1567A) on fibrin structure. FIG. 9B shows that the effect of the A2 protein on fibrin clot structure (middle panel) was validated employing the A2 mutant, which failed to modify the fibrin structure (right panel, FIG. 2B). It is known that fibrin formation in plasma or in the absence of blood cells differs from that formed in whole blood[16,17]. FIG. 2C shows images of fibrin-clot structures, generated using healthy human whole blood in the presence of the WT A2 protein. In comparison to whole blood mixed with vehicle control and dye only, it was evident that the A2 protein provoked the formation of larger pores (top left panel) and specifically localizes with the fibrin network (top middle panel) and did not interact with other blood cells (top right panel). Additionally, confocal microscopy images of a higher magnification demonstrated the incorporation of the A2 protein directly into the fibrin clot network (right panel, FIG. 2D). The capacity of the A2 protein in affecting the fibrin structure in pathological conditions was interrogated. Because the A2 protein effectively reduced fibrin-rich microthrombi in a mouse model for endotoxemia-induced DIC, the inventors tested the A2 protein using plasma from septic human patients. Notably, the A2 protein was also effective in altering the fibrin clot structure in septic plasma as shown in FIG. 103B. Although the clot structure for each patient is not the same at different days in intensive care unit (ICU), however, the A2 protein provoked a change in the resultant clot structure. These observations clearly suggest that the A2 protein can modify the clot network in plasma from healthy subjects as well as septic patients. The differences observed within the healthy and the septic patients may be attributed to the content of other plasma proteins that participate in fibrin polymerization or fibrinogen[18,19], although the level of fibrinogen had minor effects on fibrin structure in vitro 20.

Figure 3A:
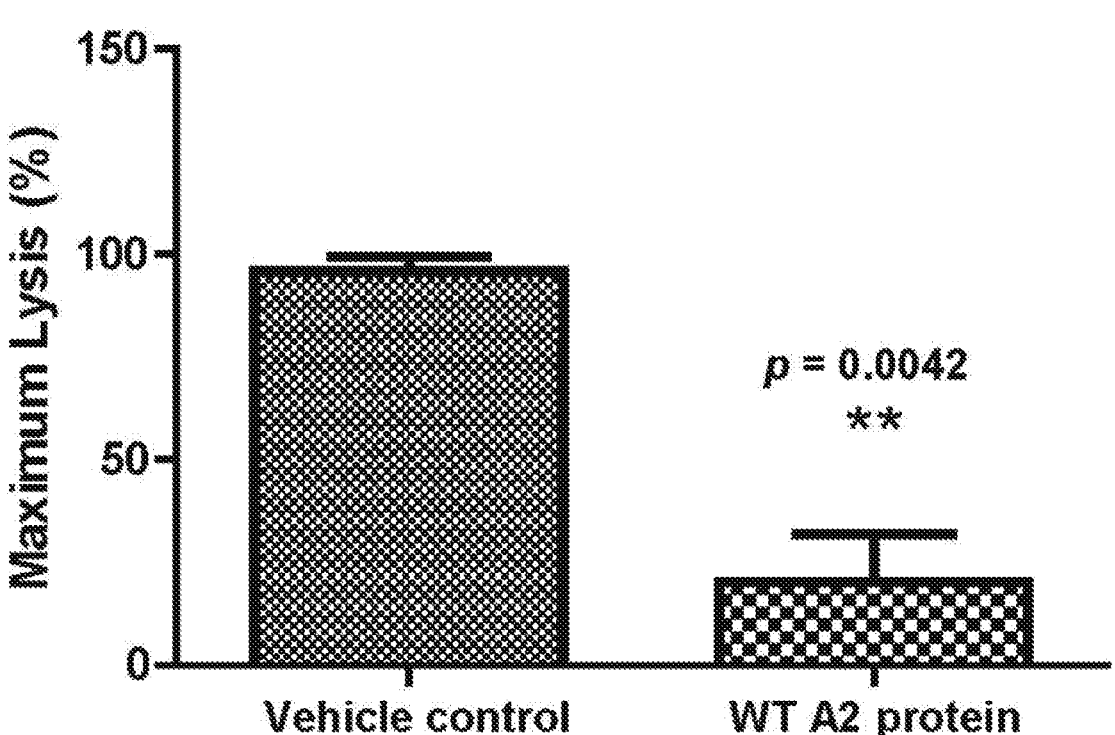
FIGS. 3A-3F The A2 protein affected fibrinolysis in vitro.
Figure 3B:
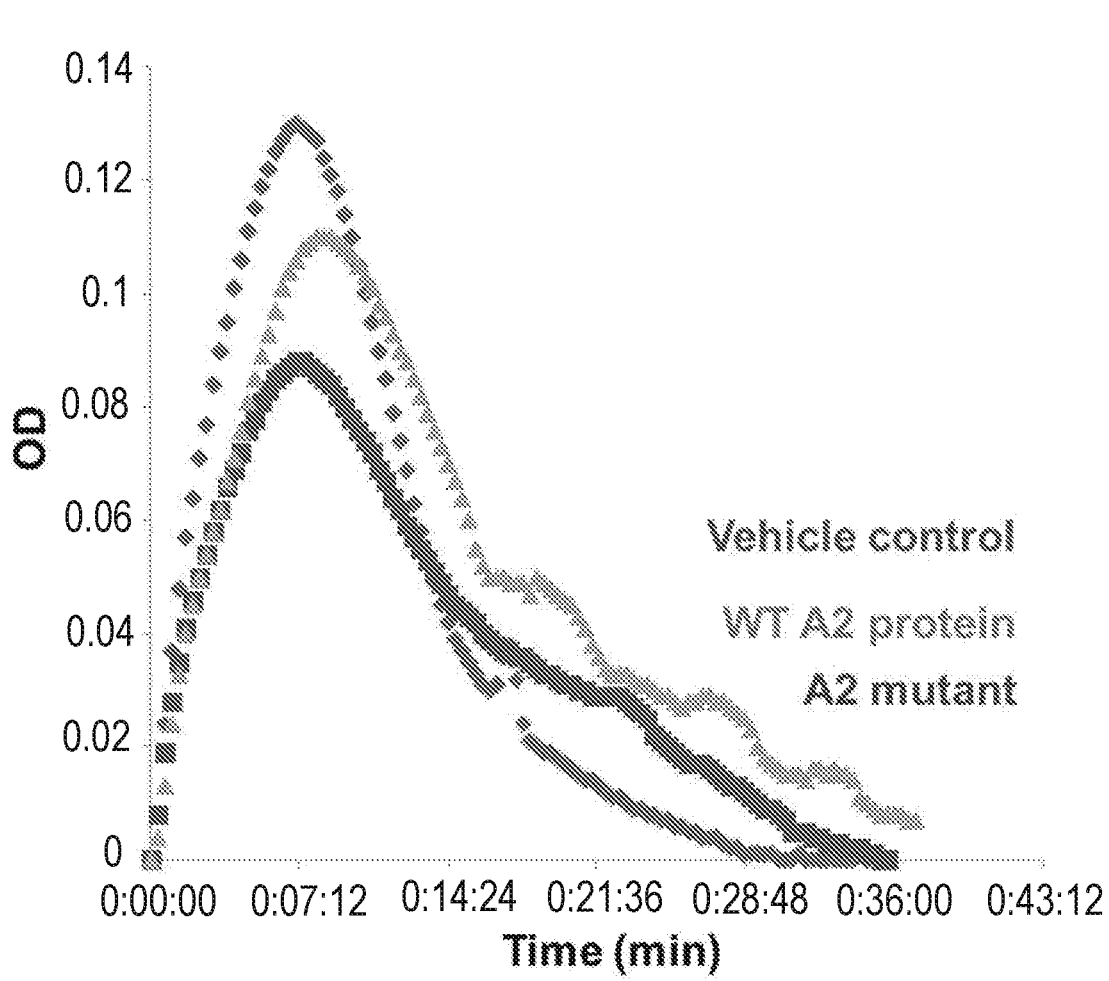
Figure 3C:
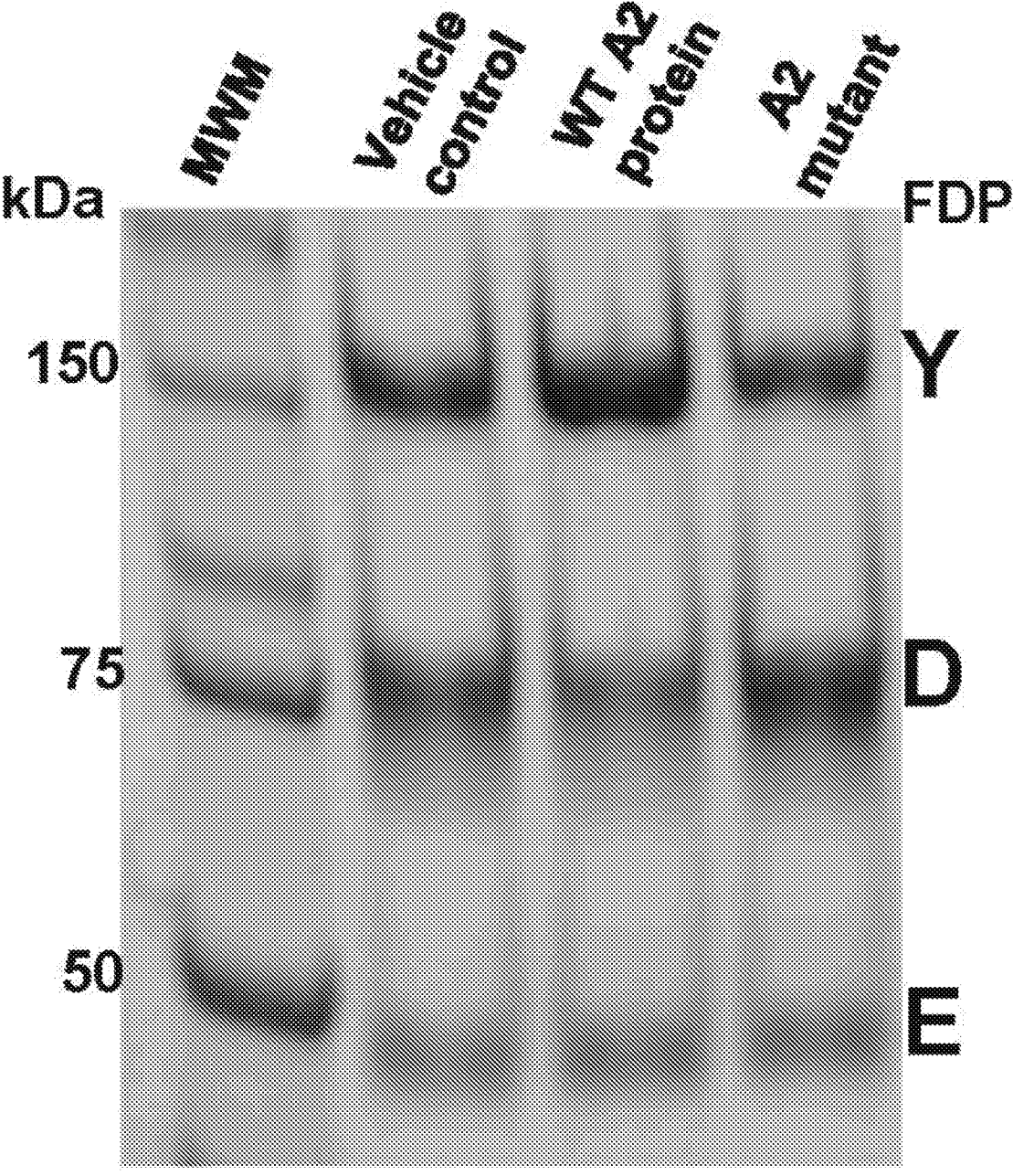
Figure 3D:
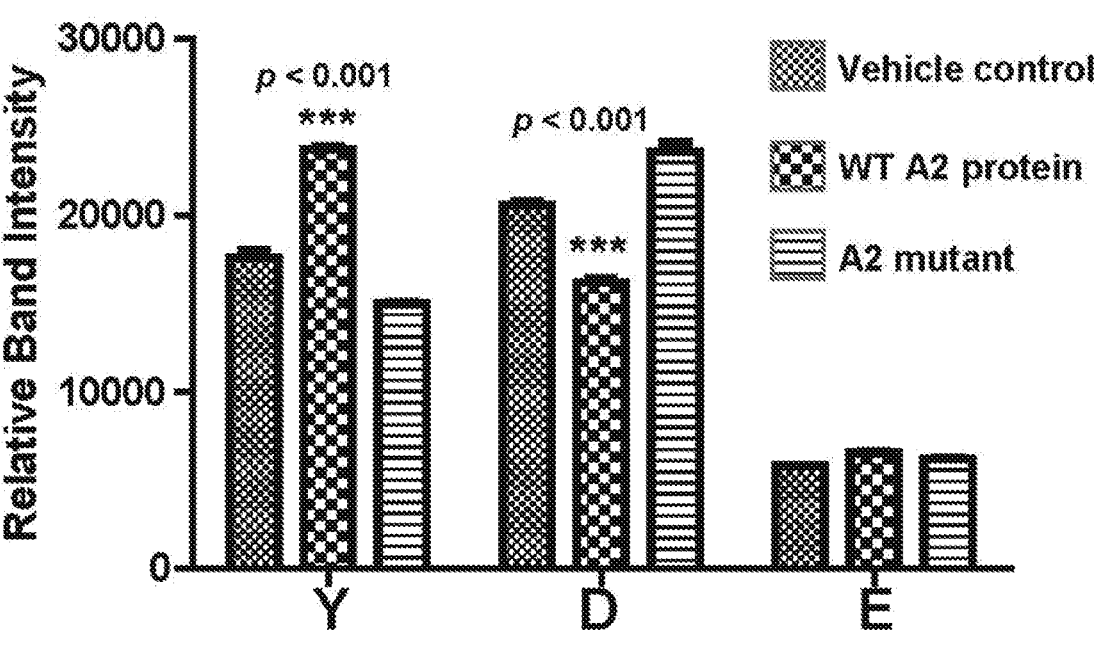
Figure 3E:
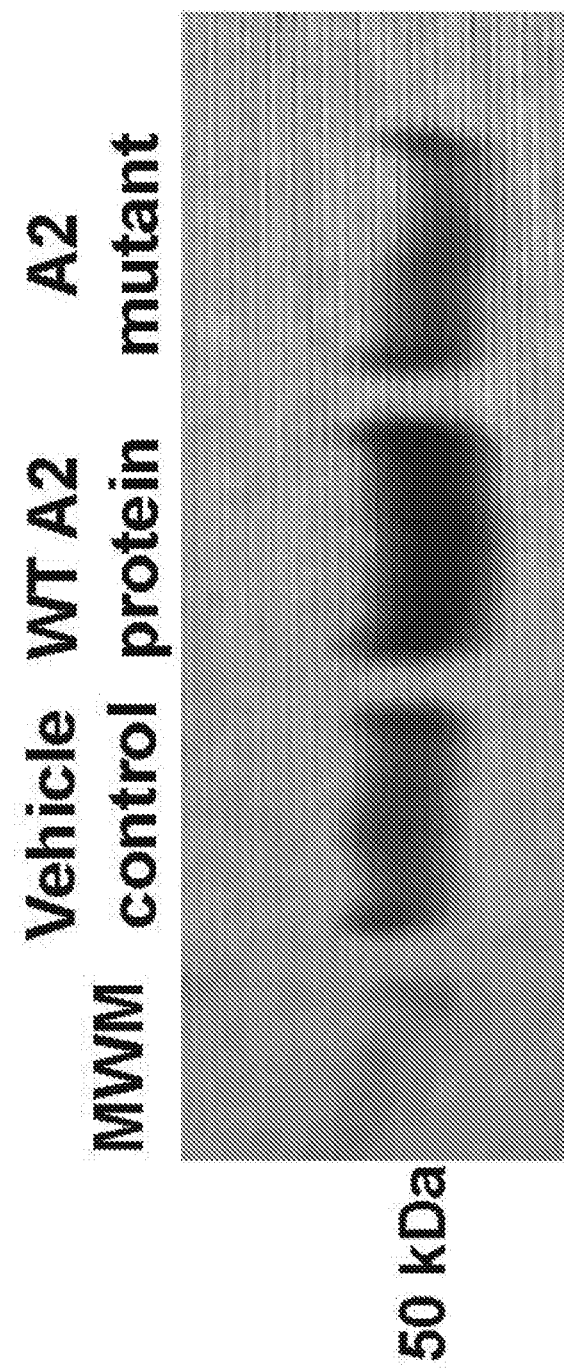
Figure 3F:
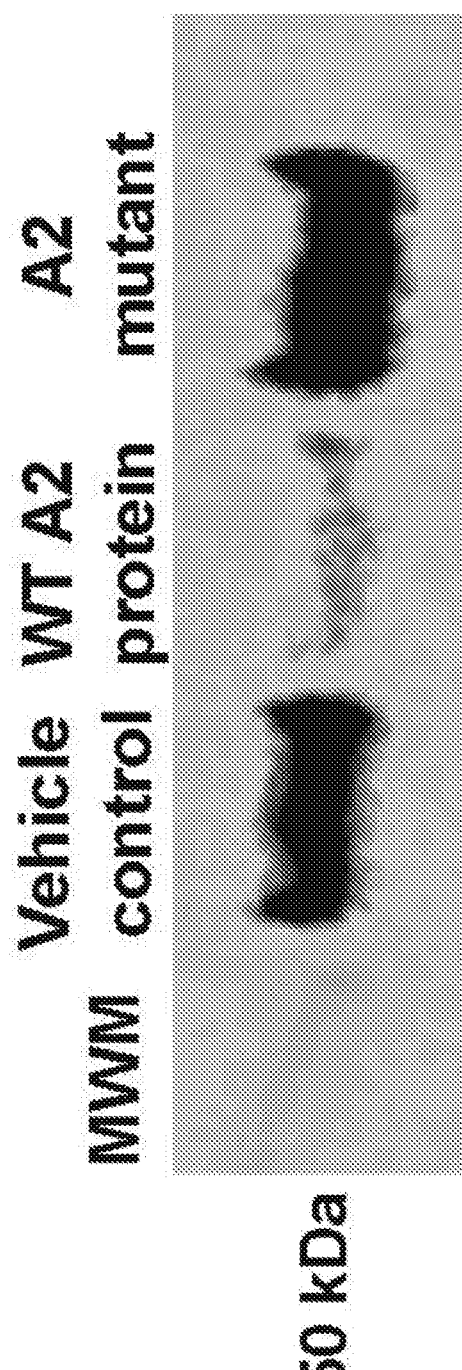
Figure 11:
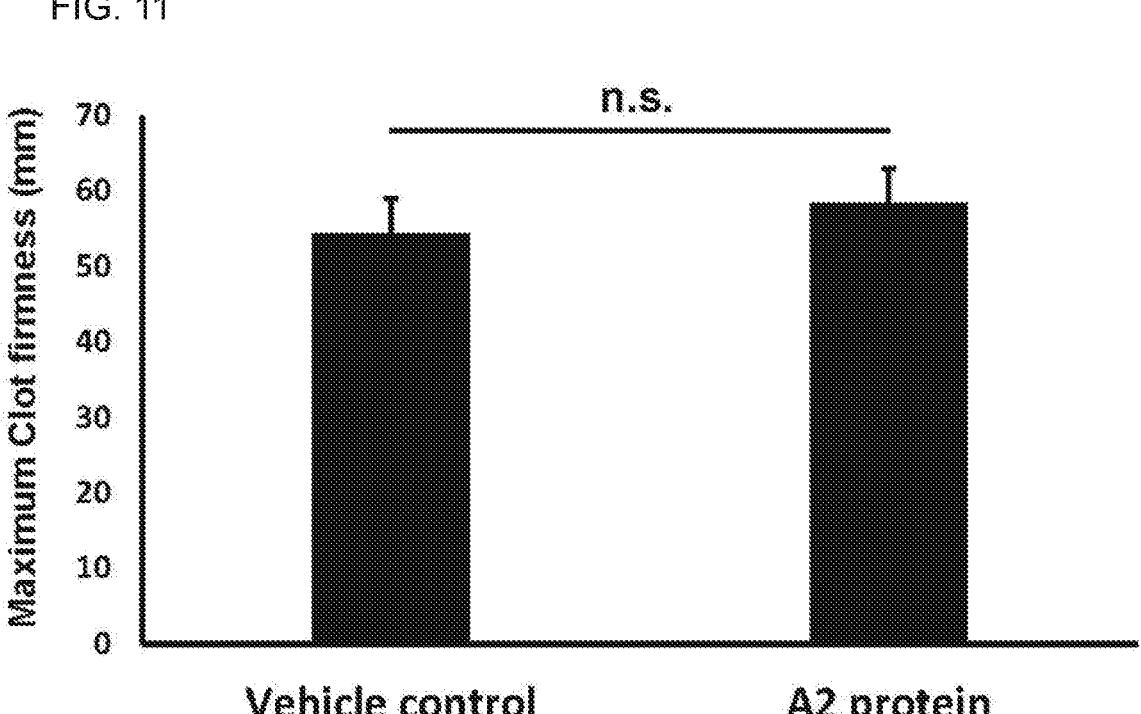
FIG. 11. Maximum Clot firmness (MCF) provides information regarding the quality/stabilization of the clot. Describes the quality of the clot before clot degradation occurs via fibrinolysis. In this experiment the addition of the WT A2 protein did not affect MCF compared to the vehicle control condition.
Figure 12:
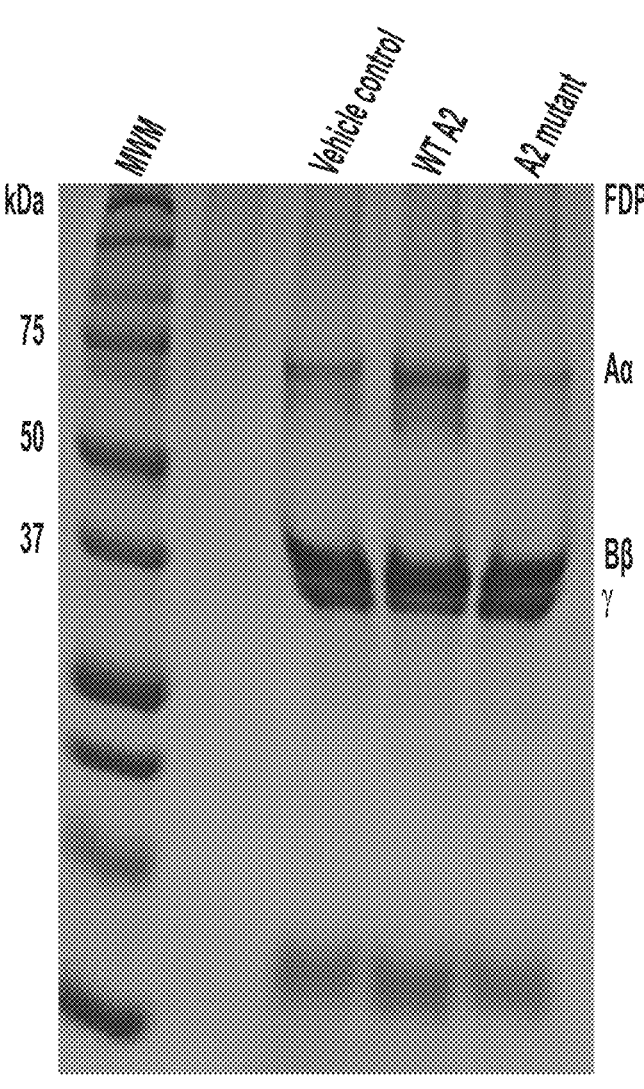
FIG. 12. Coomasie Blue stained SDS-PAGE showing the intermediate FDPs under reduced conditions. Note that as in FIG. 3C, the addition of WT A2 protein provoked an increase in the band intensity for the fragment Aα. It is also notable a reduce band intensity for the γ fragment.

The fibrin network is linked to its susceptibility to be cleaved by plasmin. The effect was examined of the fibrin-bound A2 protein on fibrinolysis using rotational thromboelastometry (e.g., ROTEM®) in whole blood from healthy donors. Rotational thromboelastometry (e.g., ROTEM®) is a clinically used tool to assess a patient's overall hemostatic state in a variety of situations (reviewed in[21]). As shown in FIG. 3A, addition of the A2 protein significantly decreased maximal lysis in tissue plasminogen activator (t-PA) treated blood but did not affect maximum clot firmness (FIG. 11). On the other hand, and as expected[13], the A2 protein decreased the rate of fibrin polymerization (time peak shifts to right) as compared to mixtures containing vehicle control or the A2 mutant (FIG. 3B). Moreover, in sharp contrast to vehicle control and A2 mutant, the second half of the curve of the clot lysis for the A2 protein clearly shows an intermittent lysis process, leading to a prolonged time to full lysis (FIG. 3B). The purified fibrinogen system was also used to investigate whether the fibrin-bound A2 protein affects the formation of fibrin degradation products (FDPs) by plasmin. The fibrin-olysis assays were conducted in the presence of either the vehicle control, the A2 protein or the A2 mutant. Samples from each digestion mixture were collected at the end of the experiment and subjected to SDS-PAGE analysis under non-reduced conditions. In comparison to the vehicle control or A2 mutant conditions, the Coomasie Blue stained gel evidently depicted that the A2 protein caused a significant increase in the band intensity corresponding to the interme-diate FDP fragment Y (MW~150 kDa), which comprises polypeptides of D domain connected to E domain of fibrino-gen[22] (FIGS. 3C and 3D). On the other hand, the band intensity for fragment D (MW~85 kDa)[22] was significantly diminished by the A2 protein. No changes in band intensity was observed for fragment E (MW~60 kDa)[22]. The increase on fragment Y was further validated using Western blot and a polyclonal anti-human fibrinogen antibody (FIG. 3E). In contrast, the opposite was noted when the same band was probed with a monoclonal antibody against high molecular weight FDPs and D-dimer of human derived fibrin (FIG. 3F). These interesting observations imply that the A2 protein modified the molecular structure of fibrin, preventing the interaction of the monoclonal antibody to fragment Y derived from fibrin-bound A2 protein. Additionally, analysis of the FDPs derived of the mixture containing the A2 protein under reduced conditions also demonstrated a significant increment for the intensity of the band corresponding to Aα fragment of fibrinogen[22] (FIG. 12). Together, these obser-vations indicate that in vitro, the A2 protein influences the rate of fibrin polymerization, modifies fibrin clot structure and alters the formation of FDPs by plasmin.

Figure 4A:
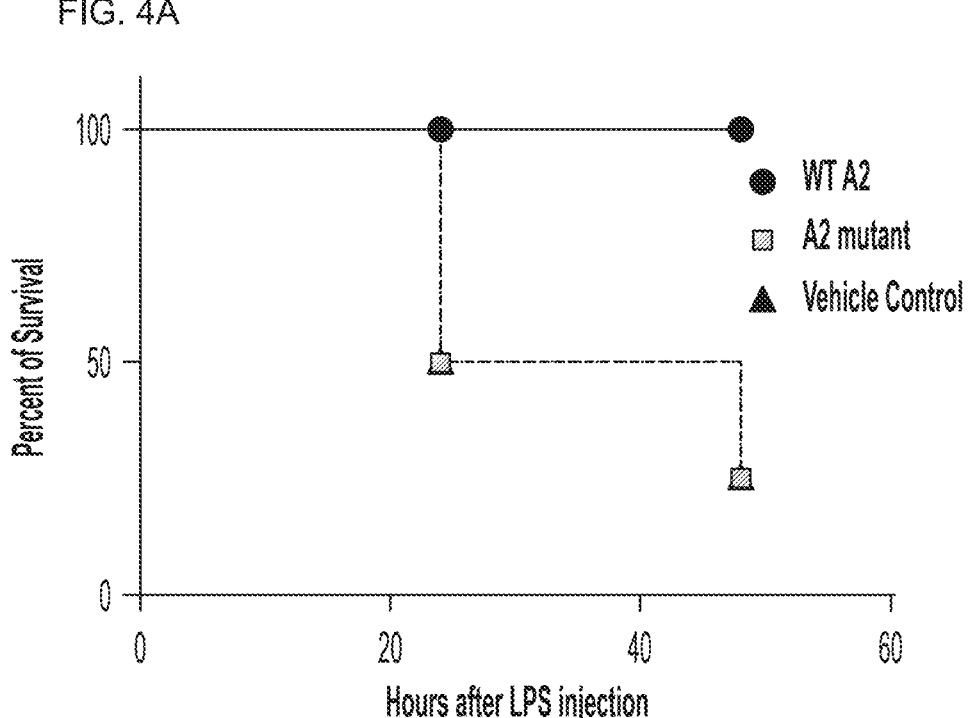
Figure 4B:
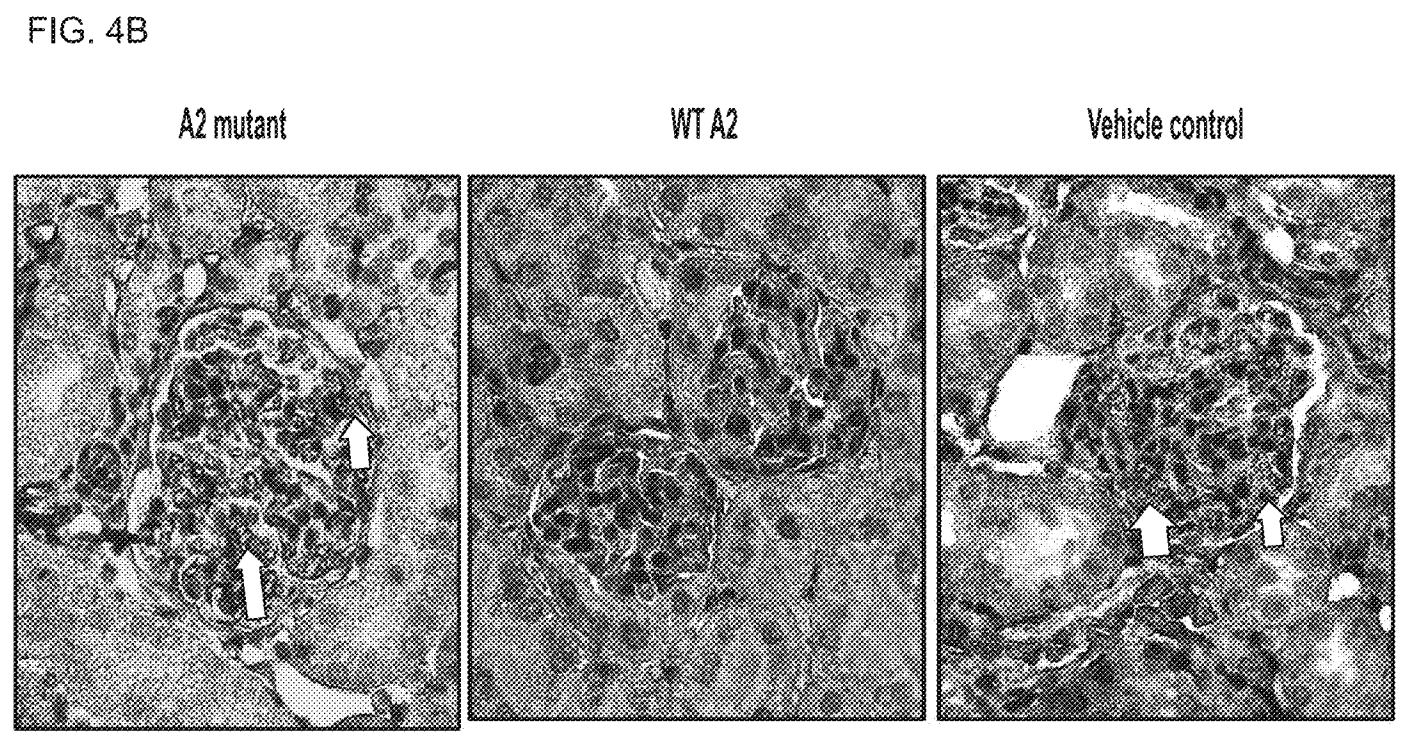
Figure 4C:
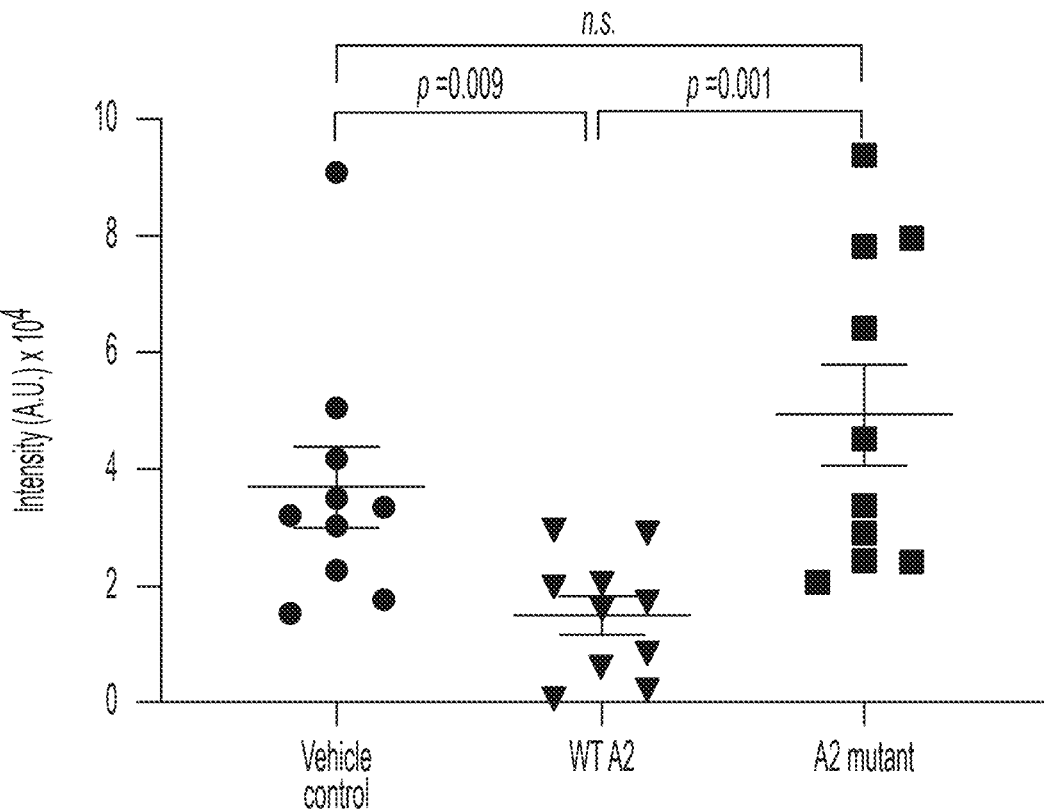
Figure 4D:
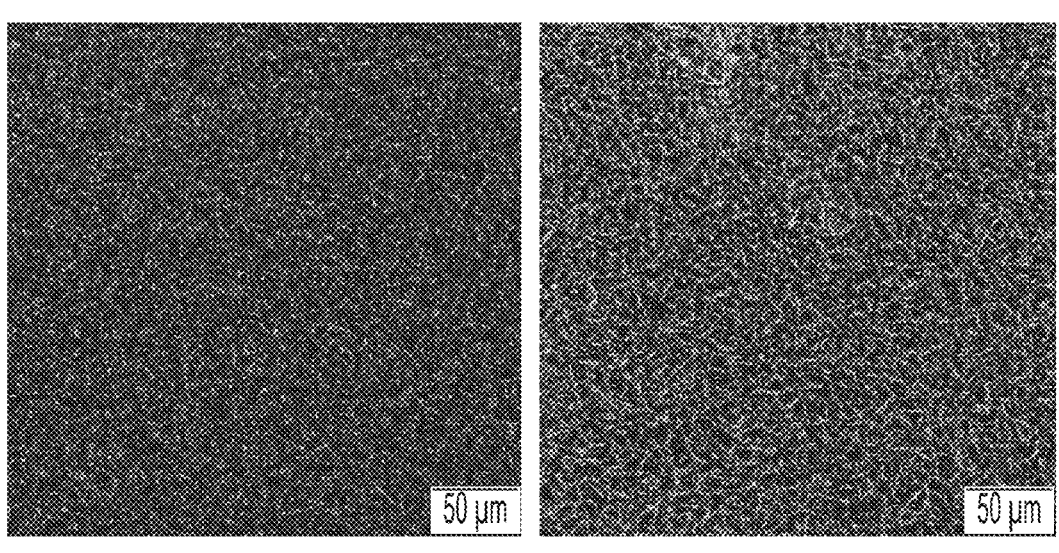
Figure 13:
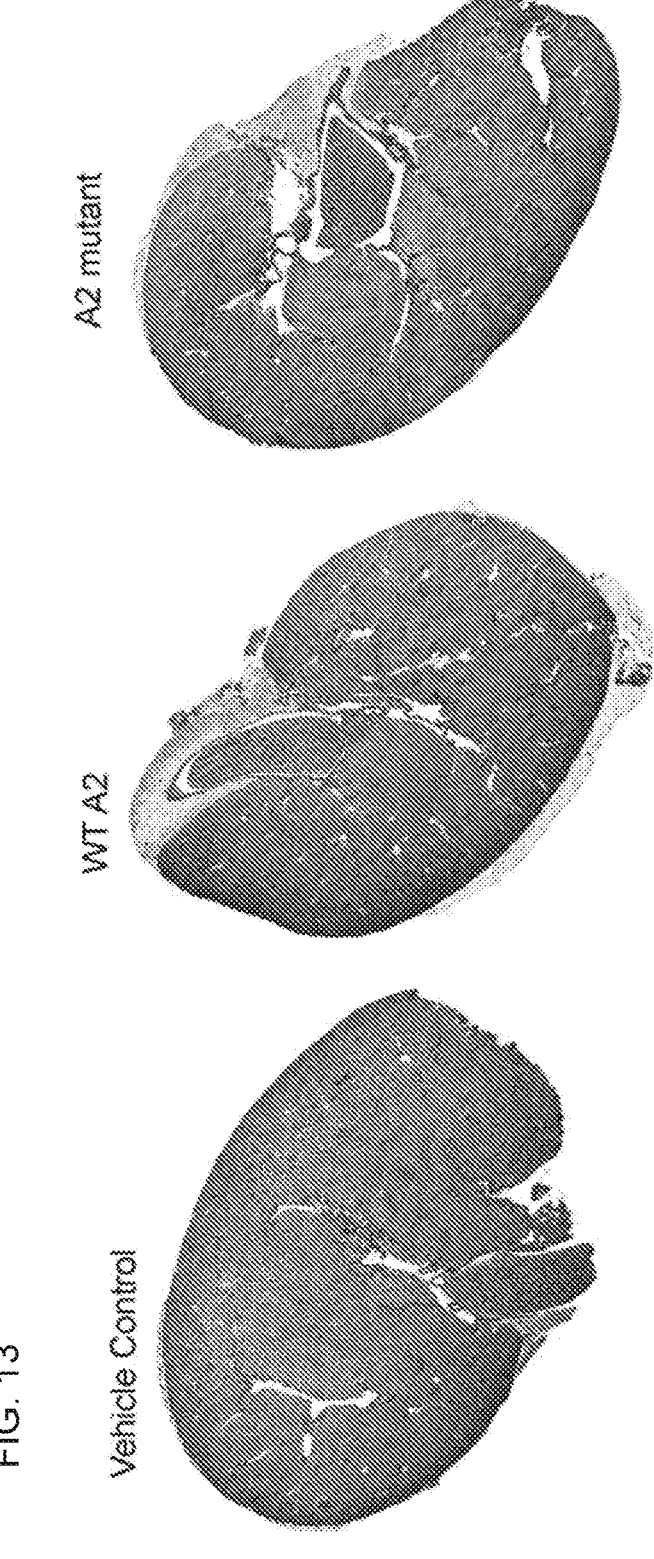
FIG. 13. Kidneys were harvested at 24 hours after the administration of LPS to mice and stained for fibrin. Dark staining depicts the fibrin deposition. In comparison to mice treated with the WT A2 protein, an increase fibrin deposition was notable for mice that received saline or the A2 mutant.

It was considered that the A2 mutant does not preserve the beneficial effect of the WT A2 protein in the inventors' endotoxemic mouse model. As previously described[13], LPS-challenged mice were treated with either the A2 mutant or the WT A2 protein (4 mg/kg) 1.5 h following the LPS insult. FIG. 4A shows that survival of LPS-challenged mice did not improve with A2 mutant compared to saline treated controls. Importantly, FIG. 13 shows representative kidney from A2 mutant-treated mice displaying a significant increase in widespread intravascular fibrin-rich microthrombi as com-pared to that of mice treated with the WT A2 protein. Particularly, the WT A2 protein was more effective in diminishing fibrin deposition in glomeruli than the A2 mutant as shown in FIGS. 4B and 4C. The fibrin clot structure in plasma of endotoxemic mice treated with saline or A2 protein was examined. By using plasma obtained at 24 h after LPS injection, the fibrin clot structure observed in plasma from a sick mouse that received the A2 protein was different (larger pores) from that of non-A2 protein LPS-challenged mouse (FIG. 4C). It should be noted that the modification on the fibrin clot structure was a consequence of having the A2 protein in the circulation of the sick animal. These results suggest that the beneficial effect of the A2 protein in the inventors' mouse model for DIC is dependent on its ability to engage fibrin.

Figure 5A:
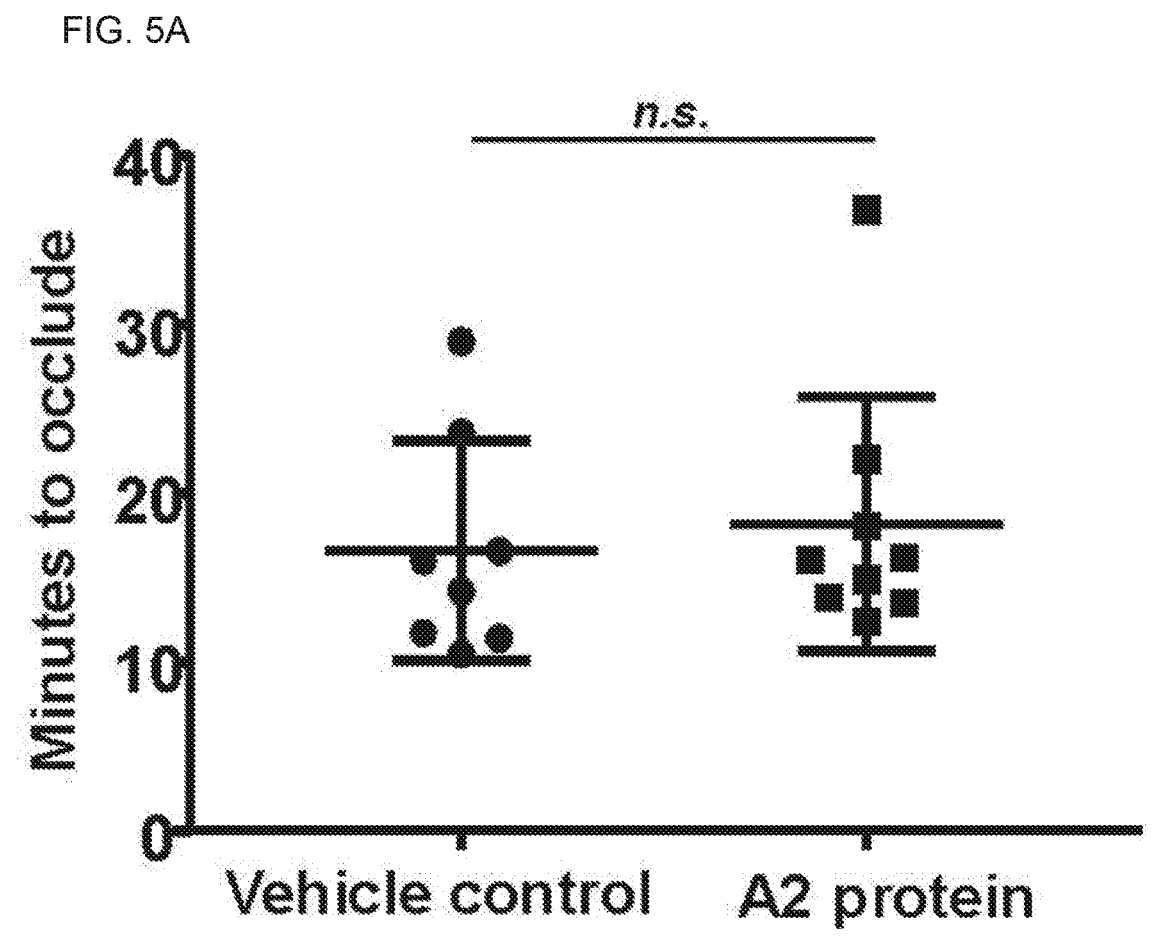
Figure 5B:
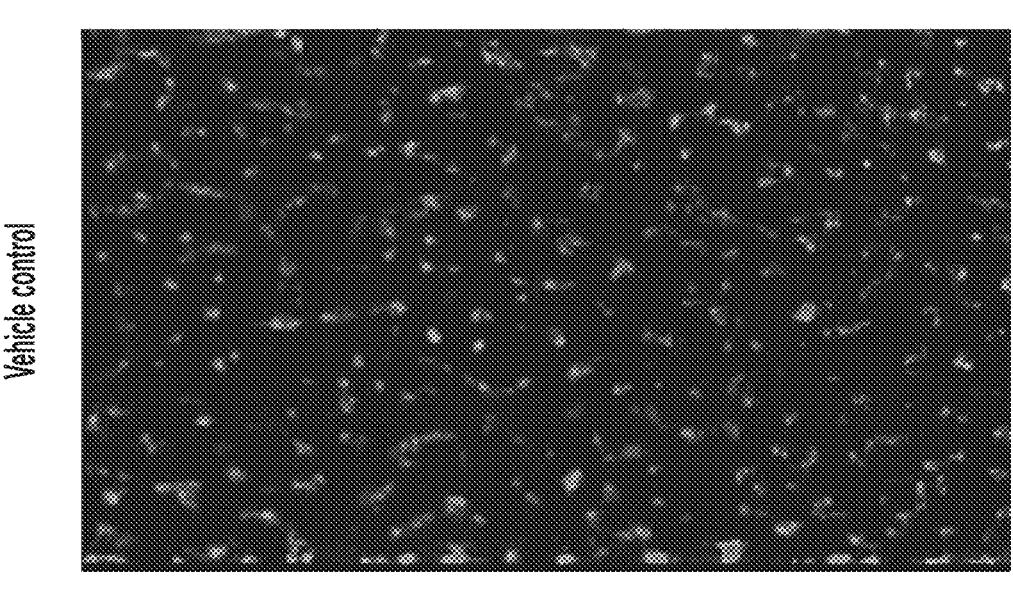
Figure 5B:
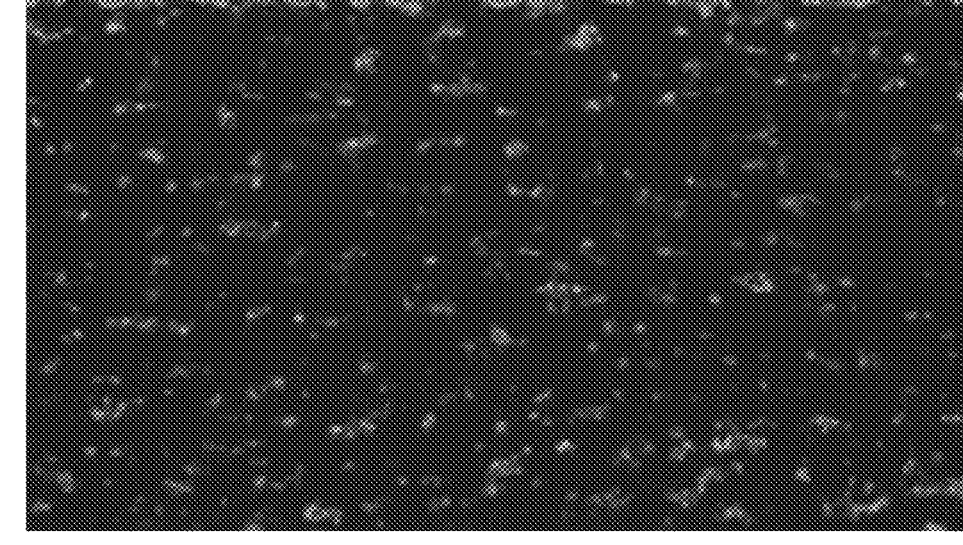
Figure 14:
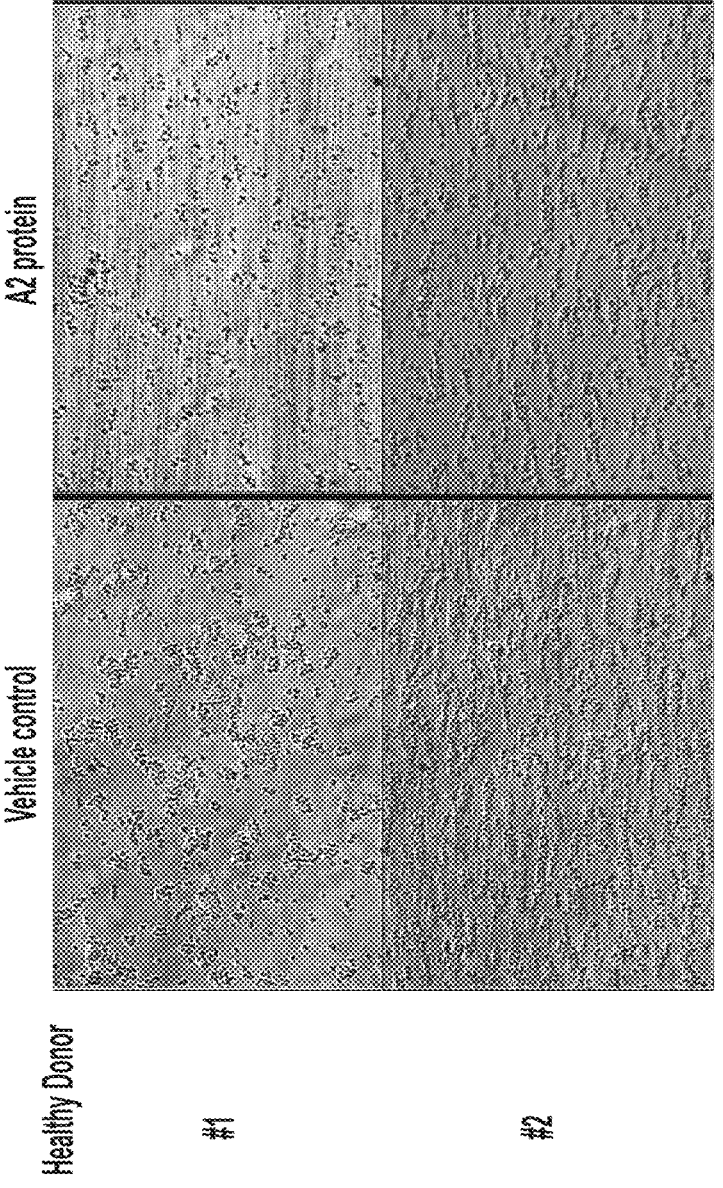
FIG. 14. Effect of WT A2 protein on flow-dependent platelet adhesion to collagen under high shear rates (1,500s−1). Whole blood from healthy human donors containing A2 protein (4.0 μM) or vehicle control was perfused over surfaces coated with human derived collagen Type III. After a 2-min perfusion, the plates were washed with tris buffer saline, TBS, and several frames of attached platelets were recorded. The photomicrographs represent three separated assays. In comparison to 10 min perfusion assays (FIG. 5B), the A2 protein slightly reduce the number of attached platelets after a short 2 min perfusion. Note the differential response of platelets (with vehicle control) derived from different individuals.

The A2 Protein does not Interfere with Primary Hemostasis and Experimental Thrombosis Several clinical trials have been conducted to attenuate morbidity and mortality associated with sepsis-induced DIC without success because the tested antithrombotic drugs can cause severe bleeding side effects[23]. The A2 protein did not affect the tail bleeding time in mice[13] nor caused more micro-hemorrhages in a porcine model of MRSA-induced sepsis (below). Thus, the effect was further examined of the A2 protein in hemostasis by using intravital microscopy in a murine thrombosis model. At the dose tested in a LPS model, the A2 protein did not alter thrombus formation in vivo as compared to animals treated with control vehicle only (FIG. 5A). In parallel, the A2 protein added to whole blood from healthy human donors did not have a profound effect on platelet adhesion and thrombus formation on collagen-coated surfaces at high shear rates in vitro (FIG. 5B and FIG. 14). These results imply that the A2 protein does not impair experimental thrombosis and primary hemostasis. The A2 Protein is Beneficial in Pigs with MRSA Sepsis-Induced DIC.

Figure 6A:
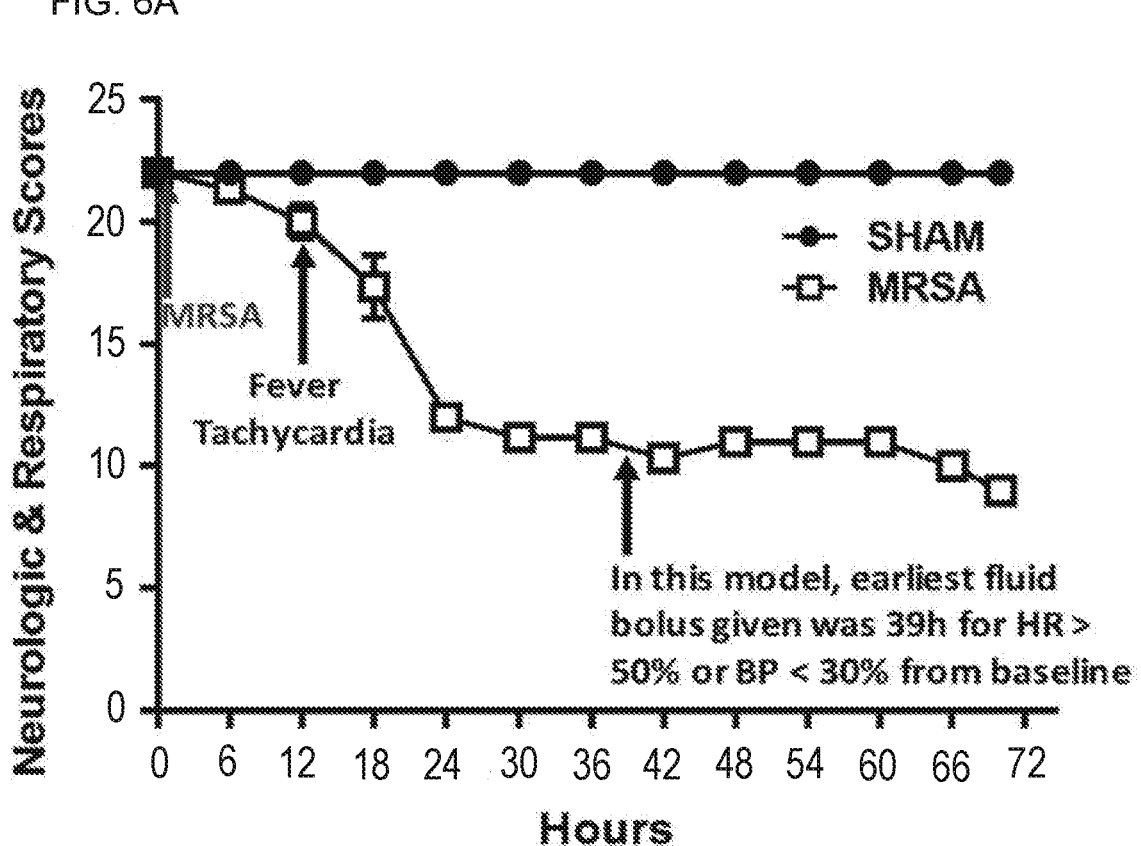
Figure 6B:
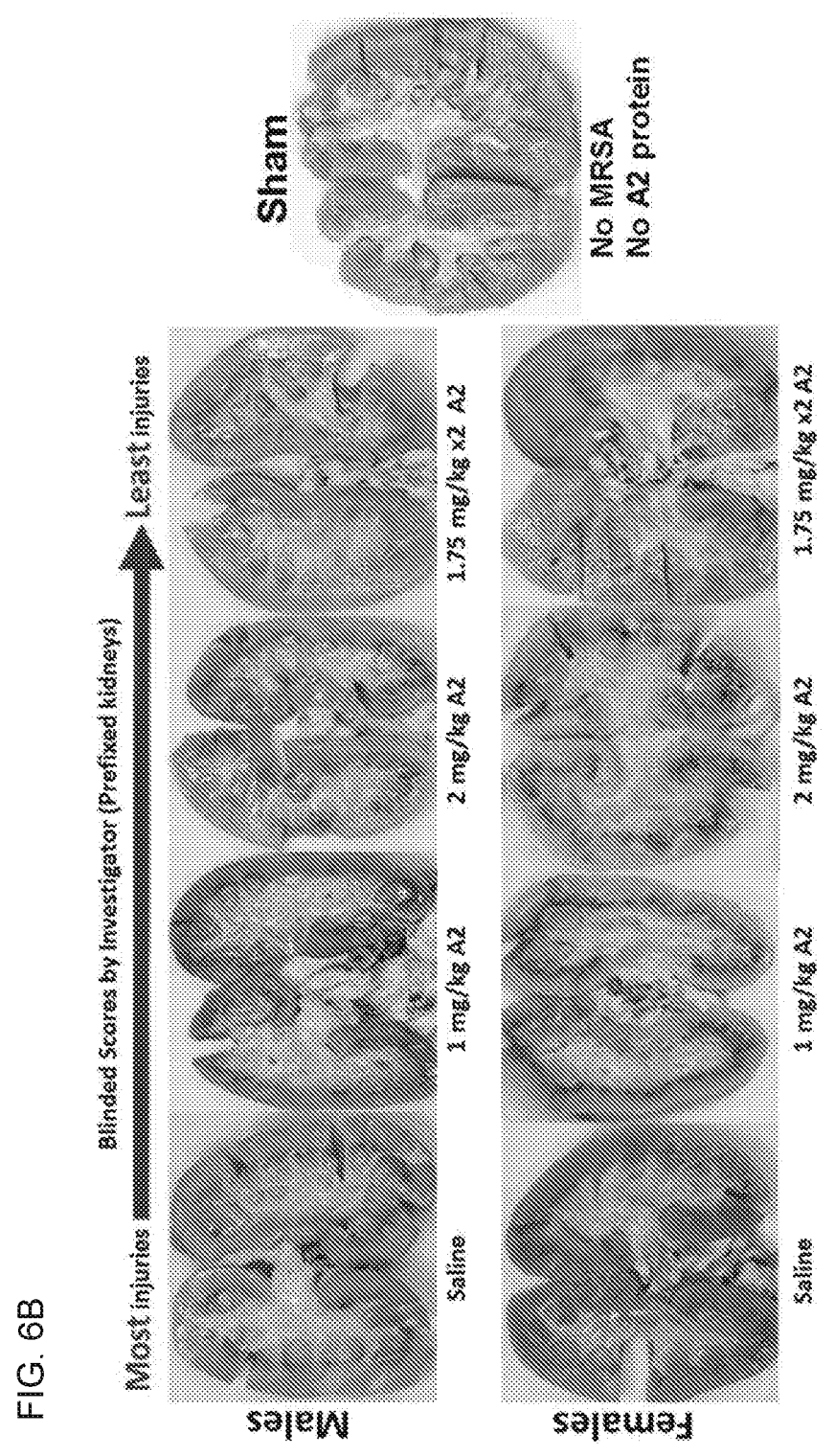
Figure 6C:
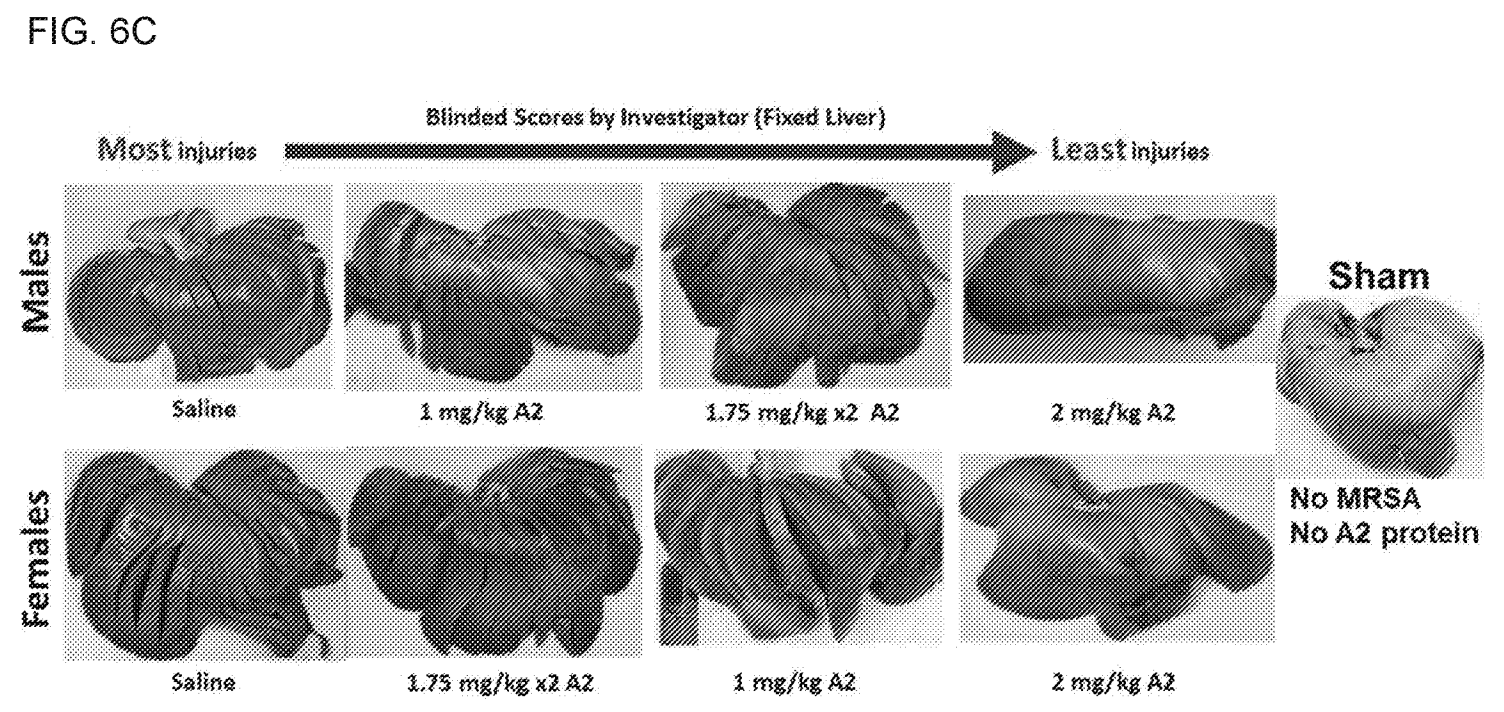

The intriguing outcomes from the murine model for LPS-induced DIC prompted investigation of the effect of A2 protein in a pre-clinical large animal model for sepsis-induced DIC. To test the effect of A2 protein in a modified porcine model[24], the pigs were treated with varying con-centrations of A2 protein (1-3.5 mg/kg) 24 h after MRSA intravenous inoculation or approximately more than 12 h after the pigs presented signs of systemic inflammation including tachycardia and fever (FIG. 6A). Necropsy was performed at 70 h, and gross examination of the tissues clearly demonstrated that the A2 protein decreased kidney—(FIG. 6B) and liver injuries (FIG. 6C) in a dose dependent manner. Further microscopic analyses were done by two blinded investigators (a pathologist and a research scientist) which showed an overall trend toward less micro-thrombi and lymphocyte foci in the liver and, less micro-hemor-rhages in the kidneys (Table 1).

| Histological Organ Injury Scores (0-3; 0 = Normal: 3 = Worst Pathology) Assessed by Blinded Investigator/Pathologist | | | | | |
|---|---|---|---|---|---|
| A2 | MRSA Sepsis—Porcine Kidneys (n = 2 for each A2 dose) (Average) | | | MRSA Sepsis—Porcine Liver (n = 2 for each A2 dose) (Average) | |
| Dose (mg/kg) | Micro-thrombi | Lymphocyte Foci | Medulla Hemorrhage | Micro-thrombi | Lymphocyte Foci |
| 0 | 1.75 | 2.25 | 1.75 | 2.5 | 2 |
| 1 | 1.75 | 2.25 | 1.75 | 0.75 | 1.5 |
| 2 | 1.5 | 1.75 | 1.75 | 0.5 | 1 |
| 3.5 | 1.5 | 1.25 | 1.25 | 2 | 2 |

Table 1. Histological Organ Injury Scores were assessed by two blinded investigators (a pathologist and a research scientist) for the liver and kidney of MRSA septic pigs (n = 8) treated with increasing dosage (0, 1, 2, and 3.5 mg/kg) of A2 protein. The severity of micro-thrombi, micro-hemorrhages and lymphocyte foci were recorded as 0 for normal and up to 3 for worst pathology.

Similar beneficial effect was also noticed in the lungs (Table 2).

| Histological Lung injury scores (Normal = 0, Worst Pathology = 4), Assessed by A blinded investigator/Pathologist. (n = 2 for each A2 dose, Average) | | |
|---|---|---|
| A2 Dose (mg/kg) | Micro-Thrombi | Hemorrhage |
| 0 | 2 | 4 |
| 1 | 0.5 | 2.5 |
| 2 | 1 | 1.5 |
| 3.5 | 0.5 | 1 |

Table 2. Histological Organ Injury Scores were assessed by two blinded investigators (a pathologist and a research scientist) for the lung of MRSA septic pigs (n = 8) treated with increasing dosage (0, 1, 2, and 3.5 mg/kg) of A2 protein. The severity of micro-thrombi, and micro-hemorrhages were recorded as 0 for normal and up to 4 for worst pathology.

Figure 6D:
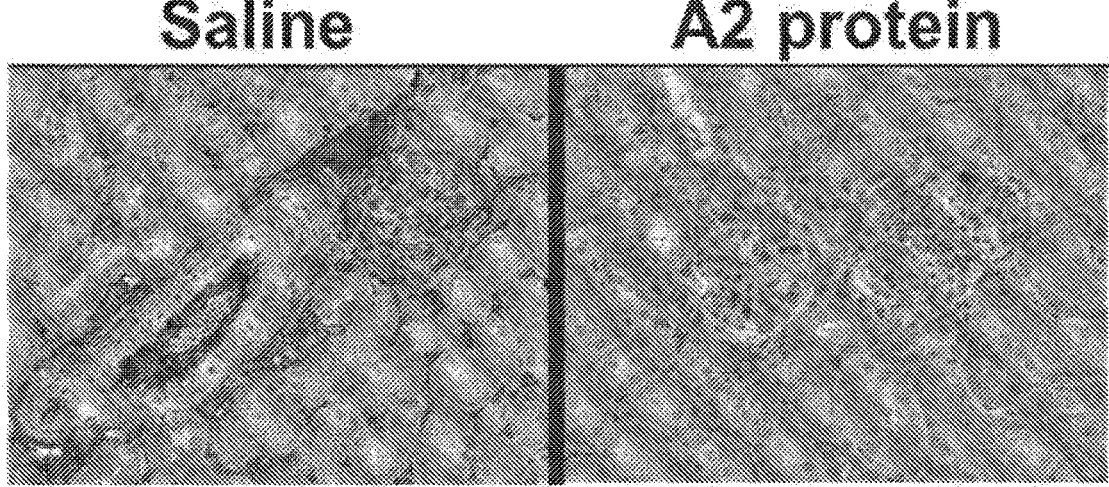
Figure 6E:
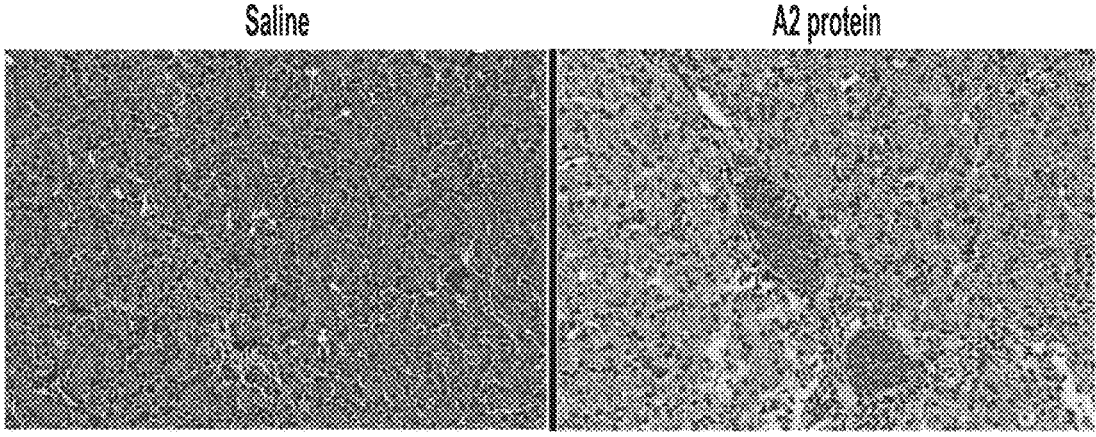

Moreover, the A2 protein was effective in diminishing both fibrin deposition in kidney and micro-hemorrhages in liver from septic pigs as seen in FIG. 6D and FIG. 6E, respectively.

Figure 7A:
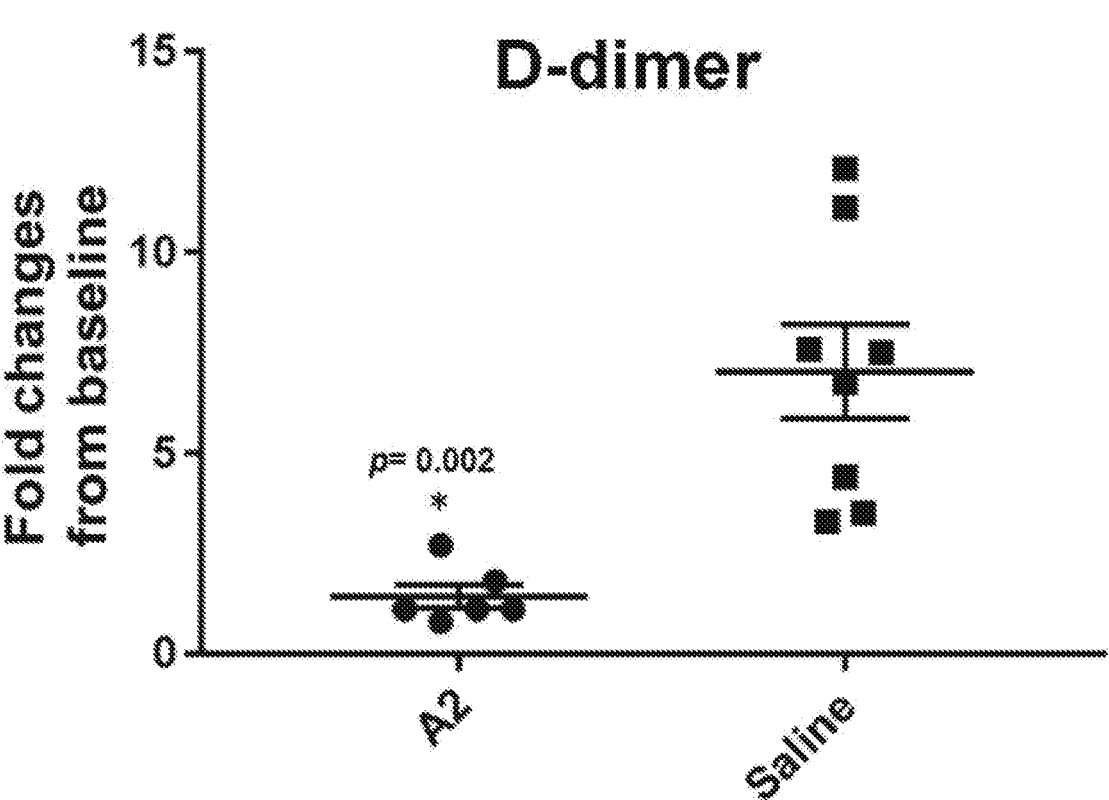
FIGS. 7A-7B. The A2 protein reduced D-dimer levels and affected fibrin clot in septic pigs.

Elevated levels of the FDP D-dimer indicate active fibrin polymerization and fibrinolytic processes and some studies have reported that high expression of D-dimer levels are associated with worse prognosis in sepsis[25,26]. FIG. 7A shows that plasma D-dimer level in A2-treated septic pigs was <1.5-fold baseline value while saline-treated sick pigs had ~7.3 fold increase from baseline value. This is a relevant outcome because human and non-human primate sepsis studies have shown a decrease in D-dimer levels when DIC was attenuated[27,28].

Figure 7B:
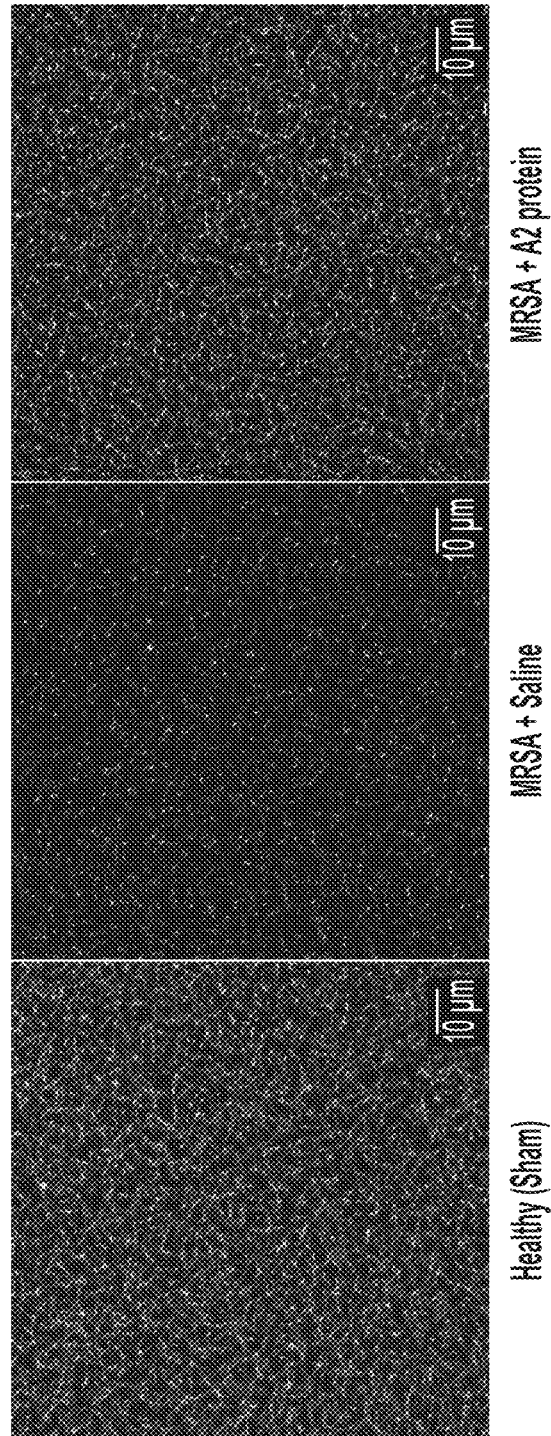

The fibrin clot structure in plasma of septic pigs was analyzed. By using plasma obtained at 60 h after MRSA infusion, the fibrin clot structure observed in plasma from the pig that received the A2 protein 24 h after MRSA inoculation had a fluorescence intensity higher than that of non-treated septic pig but comparable to sham pig (FIG. 7B). As described for LPS-treated mice (above), the variation on the fibrin clot was a consequence of infusing the A2 protein in the sick animal. Altogether, these outcomes provide compelling evidence that the A2 protein is beneficial in diminishing fibrin-rich microthrombi, micro-hemorrhages, organ injuries and D-dimer level in a large animal model of MRSA sepsis-induced DIC.

Significance of Certain Embodiments

This disclosure provides the first evidence of a recombinant A2 domain of VWF, the A2 protein, capable of affecting the fibrin clot structure and its degradation by plasmin. The use of the A2 (E1567A) mutant, which selectively lessened the binding of the A2 protein to fibrin but retained WT-binding activity for both A1 domain and vimentin, allowed dissection of the mode of action by which the A2 protein functions in vivo. The failure of the mutant to reduce microthrombi formation and improve survival of mice treated with LPS strongly indicate that the A2 protein works through an interaction with fibrin. The A2 protein does not act as an anticoagulant, but rather it directly incorporates into the formed fibrin network and, unlike the A2 mutant, influenced the resultant fibrin clot structure in plasma from different healthy human donors in a dose dependent manner. Moreover, this disclosure provides evidence that the fibrin clot structure formed in plasma derived from septic pigs and endotoxemic mice intervened with the A2 protein was different from that of the corresponding sick animals without the A2 treatment. Of note, it has been described that in sepsis and endotoxemia the fibrin clot stability is altered[17,29,30]. The fragile clots are more susceptible for fibrinolysis, which may lead to bleeding, while firm clots are more resistant, which may lead to thrombosis[29]. Moreover, changes in the architecture of the fibrin clot are associated with a high risk for thrombosis in certain diseases[8,10,11,31-33], and enhancing the fibrinolytic process has been proposed as a treatment to reduce that risk in some of these diseases[9,33].

The fibrin-bound A2 protein impacted fibrinolysis. In vitro, the clot lysis time was delayed in the presence of the A2 protein; an observation that sharply contrast to the outcomes seen in the in vivo experiments. That is, microvascular thrombosis as well as widespread fibrin deposition in different organs were markedly reduced in the A2-treated (LPS or MRSA) sick animals, suggesting that the fibrin-incorporated recombinant A2 protein ensures a normal physiologic fibrinolysis process in vivo. Additionally, high levels of D-dimer are representative of the active process of clotting and fibrinolysis, however, the septic pigs treated with the A2 protein had low levels of D-dimer as compared to the septic pigs without the A2 treatment at 70 h. This is important because it was comparable to clinical and experimental studies in which reduced D-dimer levels correlated with mitigation of DIC[25-27]. Differential fibrin clot structures have been described under static and flow conditions[34,35]. Then, one embodiment includes the influence of blood flow in the formation and degradation of fibrin in the presence of the A2 protein in vivo. In specific embodiments, one can consider that a consequence of the incorporation of the A2 protein onto the resultant fibrin structure is a change on the mechanical properties of fibrin in response to hydrodynamic forces. Another embodiment encompasses that the A2 protein contains a cleavage site for plasmin[36] and therefore, the fibrin-bound A2 protein exposes new and additional cleavage sites for plasmin in the fibrin fibers. This embodiment is supported by the striking finding that the A2 protein modified the formation of FDP by plasmin.

This disclosure is also the first one to describe the same beneficial effect of the A2 protein employing two different animal species and models for DIC (LPS/mice and MRSA/pigs). Importantly, the A2 protein was effective in diminishing fibrin deposition, fibrin-rich microthrombi formation, micro-hemorrhages, and organ injuries in a pre-clinical porcine model that appears to mimic the progression of the disease observed in humans. In fact, the widespread fibrin deposition and fibrin-rich microthrombi (hallmarks for DIC) were markedly increased in the septic animals without A2 protein treatment as compared to non-septic or sham animals, indicating that the inventors' pig model for MRSA-induced sepsis recapitulates DIC symptoms[37]. To date, DIC is sometimes managed with anticoagulants and the use of these therapies increases the risk of bleeding. Therefore, the ideal treatment for DIC should aim at reducing both the severity of bleeding and/or thrombosis without affecting hemostasis. The A2 protein did not alter tail bleeding time in mice[13] nor provoke excessive bleeding in endotoxemic mice or septic pigs, and did not affect the occlusion time in a mouse model of thrombosis. Moreover, using healthy human whole blood, the A2 protein did not significantly affect platelet deposition on a collagen surface at high shear stress. These data provide evidence that the A2 protein attenuates organ injuries due to DIC associated with systemic inflammation, sepsis, or other conditions without causing increasing bleeding or impairing primary hemostasis.

Another fascinating result obtained from this disclosure is the protective effect conferred by the A2 protein administered to the pigs 24 hours after the MRSA (intravenous) inoculation and approximately 12 hours after the infected animals presented signs of systemic inflammation, including fever and tachycardia. This efficacy was previously demonstrated using an LPS-induced DIC murine model, in which the A2 protein was given 1.5 hours after the endotoxin insult[13]. The intervention time used for the A2 protein in both murine and porcine models mostly contrast from many studies that administrated their testing therapeutic compounds before, concurrently or just after challenging the animals with endotoxin or bacteria[27,38-41]. Thus, the A2 protein demonstrated its pharmacological efficacy when the animals were already sick, which models the typical presentation of septic patients who seek medical attention after the development of symptoms. Moreover, the A2 protein was also capable in modifying the fibrin clot structure in plasma from septic patients, indicating its potential usefulness in treating patients manifesting sepsis-induced DIC.

In summary, the A2 protein binds and alters the physical structure of the resultant polymerized fibrin clot, modulating fibrinolysis. Moreover, it diminished microvascular thrombosis, organ injuries, and D-dimer level in a porcine MRSA sepsis-induced DIC model. Lastly, the A2 protein had no effect on in vivo thrombosis in a mouse model for thrombosis nor caused excessive bleeding in the septic A2-treated pigs. Therefore, the A2 protein is a novel therapeutic approach in patients with uninhibited activated coagulation and disseminated fibrin deposition, such as in DIC.

REFERENCES FOR EXAMPLE 3 IMMEDIATELY ABOVE

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

1. Gando S, Levi M, Toh C H. Disseminated intravascular coagulation. *Nat Rev Dis Primers*. 2016; 2:16037.
2. Khemani R G, Bart R D, Alonzo T A, Hatzakis G, Hallam D, Newth C J. Disseminated intravascular coagulation score is associated with mortality for children with shock. *Intensive Care Med*. 2009; 35(2):327-333.
3. Dhainaut J F, Yan S B, Joyce D E, et al. Treatment effects of drotrecogin alfa (activated) in patients with severe sepsis with or without overt disseminated intravascular coagulation. *J Thromb Haemost*. 2004; 2(11):1924-1933.
4. Zeerleder S, Hack C E, Wuillemin W A. Disseminated intravascular coagulation in sepsis. *Chest*. 2005; 128(4): 2864-2875.
5. Levi M, van der Poll T. Coagulation and sepsis. *Thromb Res*. 2017; 149:38-44.
6. Kattula S, Byrnes J R, Wolberg A S. Fibrinogen and Fibrin in Hemostasis and Thrombosis. *Arterioscler Thromb Vasc Biol*. 2017; 37(3):e13-e21.
7. Chandrashekar A, Singh G, Jonah G, Sikalas N, Labropoulos N. Mechanical and Biochemical Role of Fibrin Within a Venous Thrombus. *Eur J Vasc Endovasc Surg*. 2018; 55(3):417-424.
8. Jozwik-Plebanek K, Prejbisz A, Wypasek E, et al. Altered plasma fibrin clot properties in hypertensive patients with obstructive sleep apnoea are improved by continuous positive airway pressure treatment. *J Hypertens*. 2017; 35(5):1035-1043.
9. Kearney K, Tomlinson D, Smith K, Ajjan R. Hypofibrinolysis in diabetes: a therapeutic target for the reduction of cardiovascular risk. *Cardiovasc Diabetol*. 2017; 16(1):34.
10. Lisman T, Ariens R A. Alterations in Fibrin Structure in Patients with Liver Diseases. *Semin Thromb Hemost*. 2016; 42(4):389-396.
11. Cilia La Corte A L, Philippou H, Ariens R A. Role of fibrin structure in thrombosis and vascular disease. *Adv Protein Chem Struct Biol*. 2011; 83:75-127.
12. Abu-Fanne R, Stepanova V, Litvinov R I, et al. Neutrophil alpha-defensins promote thrombosis in vivo by altering fibrin formation, structure, and stability. *Blood*. 2019; 133(5):481-493.
13. Nguyen T C, Gushiken F, Correa J I, et al. A recombinant fragment of von Willebrand factor reduces fibrin-rich microthrombi formation in mice with endotoxemia. *Thromb Res*. 2015; 135(5):1025-1030.
14. Cushman I, Palzkill T, Moore M S. Using peptide arrays to define nuclear carrier binding sites on nucleoporins. *Methods*. 2006; 39(4):329-341.
15. Zhang Q, Zhou Y F, Zhang C Z, Zhang X, Lu C, Springer T A. Structural specializations of A2, a force-sensing domain in the ultralarge vascular protein von Willebrand factor. *Proc Natl Acad Sci USA*. 2009; 106(23):9226-9231.
16. Gersh K C, Nagaswami C, Weisel J W. Fibrin network structure and clot mechanical properties are altered by incorporation of erythrocytes. *Thromb Haemost*. 2009; 102(6):1169-1175.
17. Ostrowski S R, Berg R M G, Windelov N A, et al. Discrepant Fibrinolytic Response in Plasma and Whole Blood during Experimental Endotoxemia in Healthy Volunteers. *PLOS ONE*. 2013; 8(3):e59368.
18. Wu Y P, Bloemendal H J, Voest E E, et al. Fibrin-incorporated vitronectin is involved in platelet adhesion and thrombus formation through homotypic interactions with platelet-associated vitronectin. *Blood*. 2004; 104(4): 1034-1041.
19. Miszta A, Pelkmans L, Lindhout T, et al. Thrombin-dependent Incorporation of von Willebrand Factor into a Fibrin Network. *The Journal of Biological Chemistry*. 2014; 289(52):35979-35986.
20. Ryan E A, Mockros L F, Weisel J W, Lorand L. Structural origins of fibrin clot rheology. *Biophys J*. 1999; 77(5): 2813-2826.
21. Whiting D, DiNardo J A. TEG and ROTEM: technology and clinical applications. *Am J Hematol*. 2014; 89(2):228-232.
22. Walker J B, Nesheim M E. The molecular weights, mass distribution, chain composition, and structure of soluble fibrin degradation products released from a fibrin clot perfused with plasmin. *J Biol Chem*. 1999; 274(8):5201-5212.
23. Thachil J, Toh C H, Levi M, Watson H G. The withdrawal of Activated Protein C from the use in patients with severe sepsis and DIC [Amendment to the BCSH guideline on disseminated intravascular coagulation]. *Br J Haematol*. 2012; 157(4):493-494.
24. Soerensen K E, Olsen H G, Skovgaard K, et al. Disseminated intravascular coagulation in a novel porcine model of severe *Staphylococcus aureus* sepsis fulfills human clinical criterial. *J Comp Pathol*. 2013; 149(4): 463-474.
25. Schwameis M, Steiner M M, Schoergenhofer C, et al. D-dimer and histamine in early stage bacteremia: A prospective controlled cohort study. *Eur J Intern Med*. 2015; 26(10):782-786.
26. Toh J M, Ken-Dror G, Downey C, Abrams S T. The clinical utility of fibrin-related biomarkers in sepsis. *Blood Coagul Fibrinolysis*. 2013; 24(8):839-843.
27. Schochl H, van Griensven M, Heitmeier S, et al. Dual inhibition of thrombin and activated factor X attenuates disseminated intravascular coagulation and protects organ function in a baboon model of severe Gram-negative sepsis. *Crit Care*. 2017; 21(1):51.
28. Kountchev J, Bijuklic K, Bellmann R, Wiedermann C J, Joannidis M. Reduction of D-dimer levels after therapeutic administration of antithrombin in acquired antithrombin deficiency of severe sepsis. *Crit Care*. 2005; 9(6): R596-600.
29. Chapin J C, Hajjar K A. Fibrinolysis and the control of blood coagulation. *Blood Rev*. 2015; 29(1):17-24.

30. Gould T J, Vu T T, Stafford A R, et al. Cell-Free DNA Modulates Clot Structure and Impairs Fibrinolysis in Sepsis. *Arterioscler Thromb Vasc Biol.* 2015; 35(12): 2544-2553.

31. Wang X, Friis T E, Masci P P, Crawford R W, Liao W, Xiao Y. Alteration of blood clot structures by interleukin-1 beta in association with bone defects healing. *Sci Rep.* 2016; 6:35645.

32. Neergaard-Petersen S, Hvas A M, Kristensen S D, et al. The influence of type 2 diabetes on fibrin clot properties in patients with coronary artery disease. *Thromb Haemost.* 2014; 112(6):1142-1150.

33. Lord S T. Molecular mechanisms affecting fibrin structure and stability. *Arterioscler Thromb Vasc Biol.* 2011; 31(3):494-499.

34. Campbell R A, Aleman M, Gray L D, Falvo M R, Wolberg A S. Flow profoundly influences fibrin network structure: implications for fibrin formation and clot stability in haemostasis. *Thromb Haemost.* 2010; 104(6): 1281-1284.

35. Gersh K C, Edmondson K E, Weisel J W. Flow rate and fibrin fiber alignment. *J Thromb Haemost.* 2010; 8(12): 2826-2828.

36. Brophy T M, Ward S E, McGimsey T R, et al. Plasmin Cleaves Von Willebrand Factor at K1491-R1492 in the A1-A2 Linker Region in a Shear- and Glycan-Dependent Manner In Vitro. *Arterioscler Thromb Vasc Biol.* 2017; 37(5):845-855.

37. Levi M, Schultz M, Van Der Poll T. Sepsis and Thrombosis. *Semin Thromb Hemost.* 2013.

38. Slofstra S H, van t, V, Buurman W A, Reitsma P H, ten C H, Spek C A. Low molecular weight heparin attenuates multiple organ failure in a murine model of disseminated intravascular coagulation. *Crit Care Med.* 2005; 33(6): 1365-1370.

39. Carraway M S, Welty-Wolf K E, Kantrow S P, et al. Antibody to E- and L-selectin does not prevent lung injury or mortality in septic baboons. *Am J Respir Crit Care Med.* 1998; 157(3 Pt 1):938-949.

40. Welty-Wolf K E, Carraway M S, Ghio A, Kantrow S P, Huang Y C, Piantadosi C A. Proinflammatory cytokines increase in sepsis after anti-adhesion molecule therapy. *Shock.* 2000; 13(5):404-409.

41. Keshari R S, Silasi R, Popescu N I, et al. Inhibition of complement C5 protects against organ failure and reduces mortality in a baboon model of *Escherichia coli* sepsis. *Proc Natl Acad Sci USA.* 2017.

42. Fu X, Chen J, Gallagher R, Zheng Y, Chung D W, Lopez J A. Shear stress-induced unfolding of VWF accelerates oxidation of key methionine residues in the A1A2A3 region. *Blood.* 2011; 118(19):5283-5291.

43. Dong J F, Moake J L, Nolasco L, et al. ADAMTS-13 rapidly cleaves newly secreted ultralarge von Willebrand factor multimers on the endothelial surface under flowing conditions. *Blood.* 2002; 100(12):4033-4039.

44. McKinnon T A, Chion A C, Millington A J, Lane D A, Laffan M A. N-linked glycosylation of VWF modulates its interaction with ADAMTS13. *Blood.* 2008; 111(6): 3042-3049.

Example 4

Figure 15:
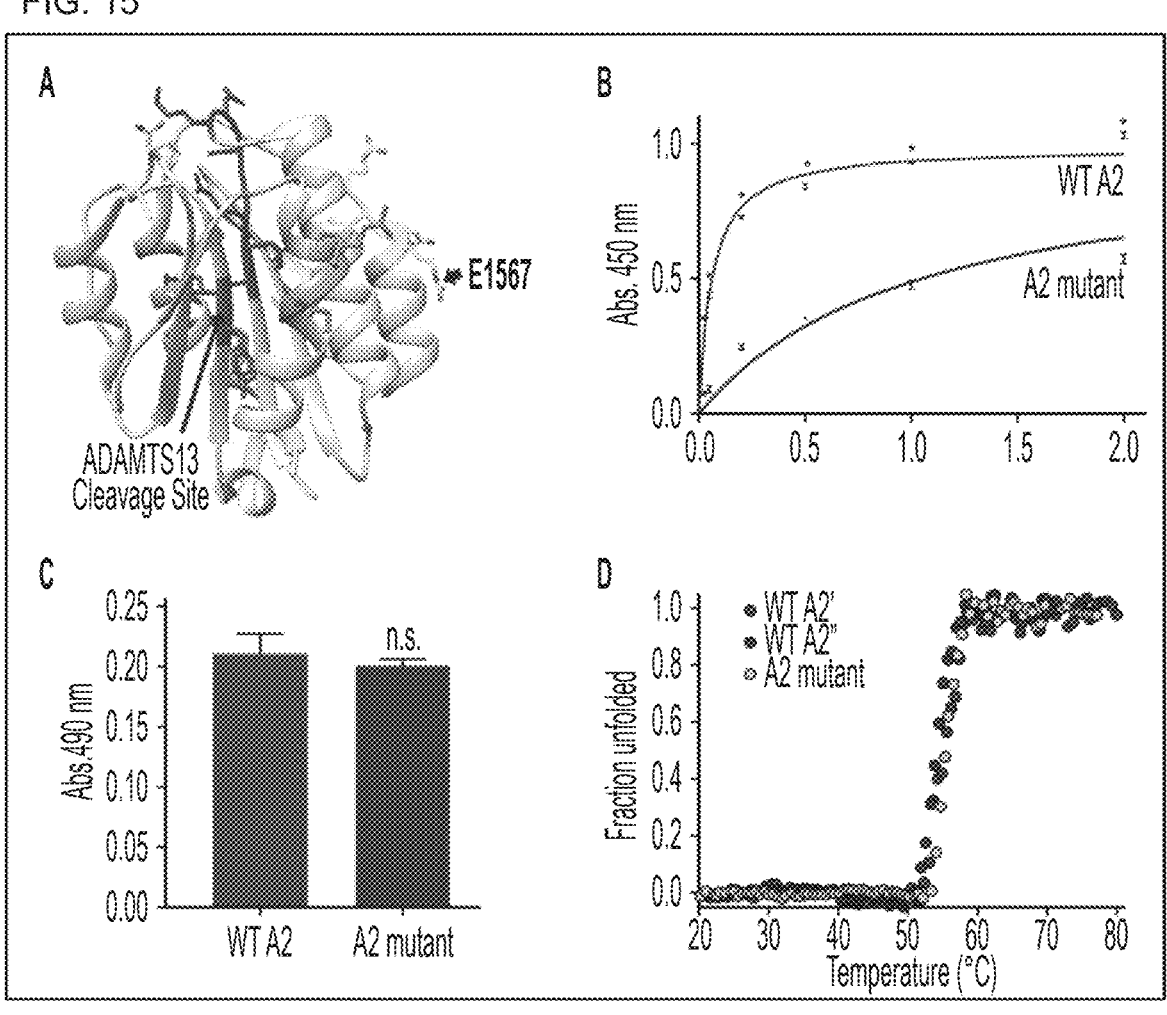
FIGS. 15A-15D. Identification of fibrin contact regions in the A2 domain of VWF.

Modulating the Rate of Fibrin Formation and Clot Structure Attenuates Microvascular Thrombosis in Systemic Inflammation Identification of a Putative Binding Site for Fibrin in the A2 Domain of VWF The inventors used the peptide SPOT array technique[20] to identify the putative contact sites for fibrin within the A2 domain structure. To this end, 18 meric overlapping peptides derived from the amino acid sequence of the A2 domain (G1481-R1668) were directly synthesized on a cellulose membrane and probed for binding to fibrin (FIG. 22). After analyzing the intensity of the binding spots, the resultant residues were mapped onto the crystal structure of the A2 domain (FIG. 15A).[25] The regions α2-helix and α6-helix most likely form the putative contact sites for fibrin, although the β1-strand could contribute if the A2 protein is unfolded before the binding to fibrin. Among the A2 mutants constructed (not shown), the purified A2 (E1567A) mutant (FIG. 23A) exhibited a much lower binding affinity for fibrin than that of the WT A2 protein (half maximal binding constant, $1.03\pm0.079$ μM vs $0.06\pm0.004$ μM, respectively; FIG. 15B). Note that the peptide sequence containing the amino acid residue E1567 on the cellulose membrane was readily detected by fibrin (FIG. 15; FIG. 22). Another feature of this A2 mutant is that in comparison with the WT A2 protein, the E1567A mutation did not alter the overall structure of the recombinant A2 protein, as demonstrated by studies using a monoclonal antibody (FIG. 15C) and circular dichroism thermal unfolding (FIG. 15D). Furthermore, the A2 mutant bound to both the recombinant A1 domain of VWF and vimentin (FIG. 23b-23c, respectively), comparably to the WT A2 protein. Thus, the E1567A mutation did not alter the overall A2 protein structure and specifically impaired the interaction with fibrin without affecting the binding affinity of either the A1 domain of VWF or vimentin. The residue E1567 apparently forms part of the contact region for fibrin in the A2 protein.

A2 Protein Influences the Initial Change of the Fibrin Formation Rate in Human Plasma Next, the inventors employed turbidity assays to examine the hypothesis that the A2 protein influences the kinetics of fibrin polymerization in plasma from healthy human donors. The assays were conducted using plasma containing increasing concentrations of the A2 protein. FIG. 16A-16B shows that the A2 protein significantly reduced the time (ie, increased the rate) to reach the maximum (optical density absorbance) turbidity in a dose-dependent manner. Similarly, the initial rate of change increased as the A2 concentrations increased (Table 3).

| A2 [μM] | Slope × $10^{-5}$ |
|---------|-------------------|
| 0 | 5.3 |
| 0.05 | 6.7 |
| 0.1 | 12.7 |
| 0.25 | 13.6 |
| 0.5 | 15.7 |

Table 3. The initial rate of change (slope) at different concentrations of A2 protein as described in FIG. 16.

The initial rate of change was determined from the slope of the line at the midpoint between initial baseline and maximum absorbance as described.[26] In contrast, the A2 (E1567A) mutant did not affect the rate of fibrin polymerization (FIG. 24A-24B), suggesting that the A2 protein influences the rate of fibrin formation.

A2 Protein Alters and Intercalates into the Fibrin Clot Structure

Because the A2 protein accelerates the fibrin formation in plasma, the inventors next examined the effect of the A2 protein on the polymerized fibrin structure using confocal microscopy. FIG. 17A shows representative images of the fibrin structure formed in plasma from healthy human donors. Note that the 3-dimensional reconstruction of fibrin formed in the presence of the A2 protein (top right) gives the impression of greater density than the control clot (top left). Z-stack representative images show that the A2 protein apparently induced the formation of larger pores in the resultant dense-appearing clot (bottom right) in comparison with vehicle control (bottom left). In fact, as shown in FIG. 17B, considerable variation in the network structure with the WT A2 protein (middle) was observed in comparison with plasma incubated with either vehicle control (left) or A2 mutant (right). Intrinsic differences in the resultant fibrin clot structure among donors were evident when the inventors performed additional experiments using plasma from multiple healthy human donors. However, A2 protein-induced alteration in the fibrin structure was clearly distinguishable for each donor studied, and it significantly increased the porosity of the fibrin network (FIG. 25A-25B). The inventors next evaluated the clot porosity by measuring flow-through.[27] The graph in FIG. 25C gives the impression that the A2 protein apparently increased the porosity of the resultant clot (slightly higher flowthrough); however, the changes were not significant. The differences observed within the healthy donors and between the assays may be attributed to the content of other plasma proteins that participate in fibrin polymerization or fibrinogen,[28,29] although the level of fibrinogen had minor effects on fibrin structure in vitro.[30]

Figure 18:
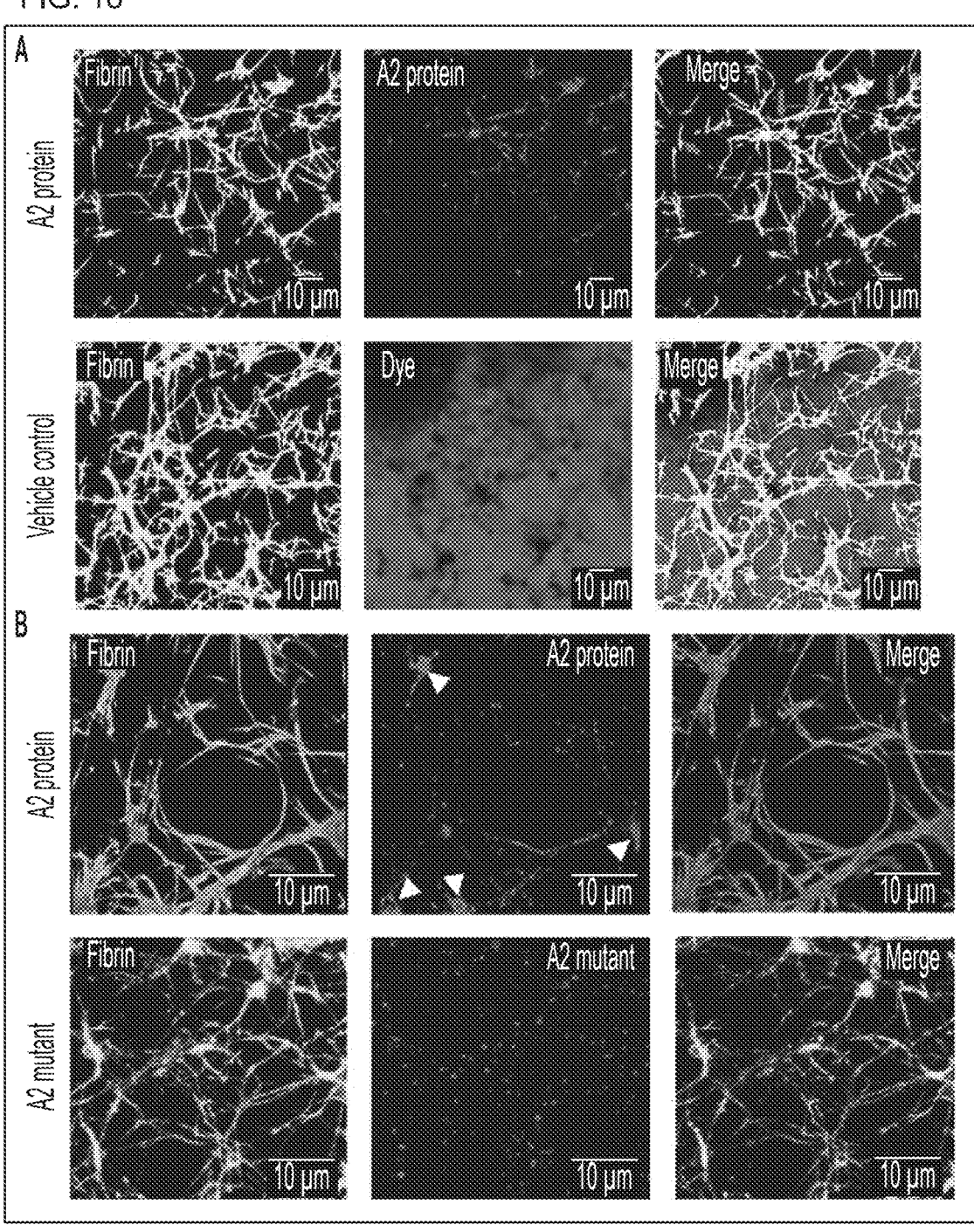
FIGS. 18A-18B. The A2 protein alters and is incorporated into the fibrin clot structure.

Fibrin formation in plasma or in the absence of blood cells differs from that in whole blood[31,32] FIG. 18A shows images of fibrin clot structures, generated using healthy human whole blood in the presence of the A2 protein (0.5 μM). In comparison with whole blood mixed with vehicle control and dye only, it was evident that the A2 protein caused the formation of larger pores (top left) and specifically localized and overlapped with the fibrin network (top middle) and did not interact with other blood cells (top right vs bottom right, dye only). Additionally, confocal microscopy images of a higher magnification demonstrated the incorporation of the fluorescently labeled A2 protein directly into the fibrin clot network or fibrils (FIG. 18B top middle), particularly at the location of fibrin branchings (white arrowheads). In contrast, the size of the pores formed in the presence of the A2 mutant (0.5 μM; FIG. 18B bottom left) was smaller than that of those caused by the WT A2 protein (FIG. 18B top left). In addition, the incorporation of the A2 mutant into the clot structure (FIG. 18B bottom middle) was significantly lower (FIG. 26) and did not form clusters in locations of fibrin branching as compared with the WT A2 protein (FIG. 18B top middle). These outcomes indicate that the A2 protein is incorporated into the fibrin networks, and this interaction results in structural changes in the fibrin clot, causing larger pores.

Because the fibrin network is susceptible to cleavage by plasmin, the inventors examined the hypothesis that the A2 protein binding to the fibrin network structure influences fibrin degradation by plasmin. The fibrin polymerization and fibrinolysis assays were conducted in healthy human plasma mixed with tissue plasminogen activator in the presence of either vehicle control or the A2 protein. Although the A2 protein reduced the time to reach maximum absorbance, it did not have a marked effect on fibrin degradation, as compared with plasma incubated with vehicle control (FIG. 27). These outcomes indicate that the A2 protein specifically influences the rate of fibrin polymerization and its resultant clot structure without altering fibrin degradation by plasmin in healthy plasma in vitro.

A2 Protein-Fibrin Interaction Attenuates Microvascular Thrombosis In Vivo

Figure 19:
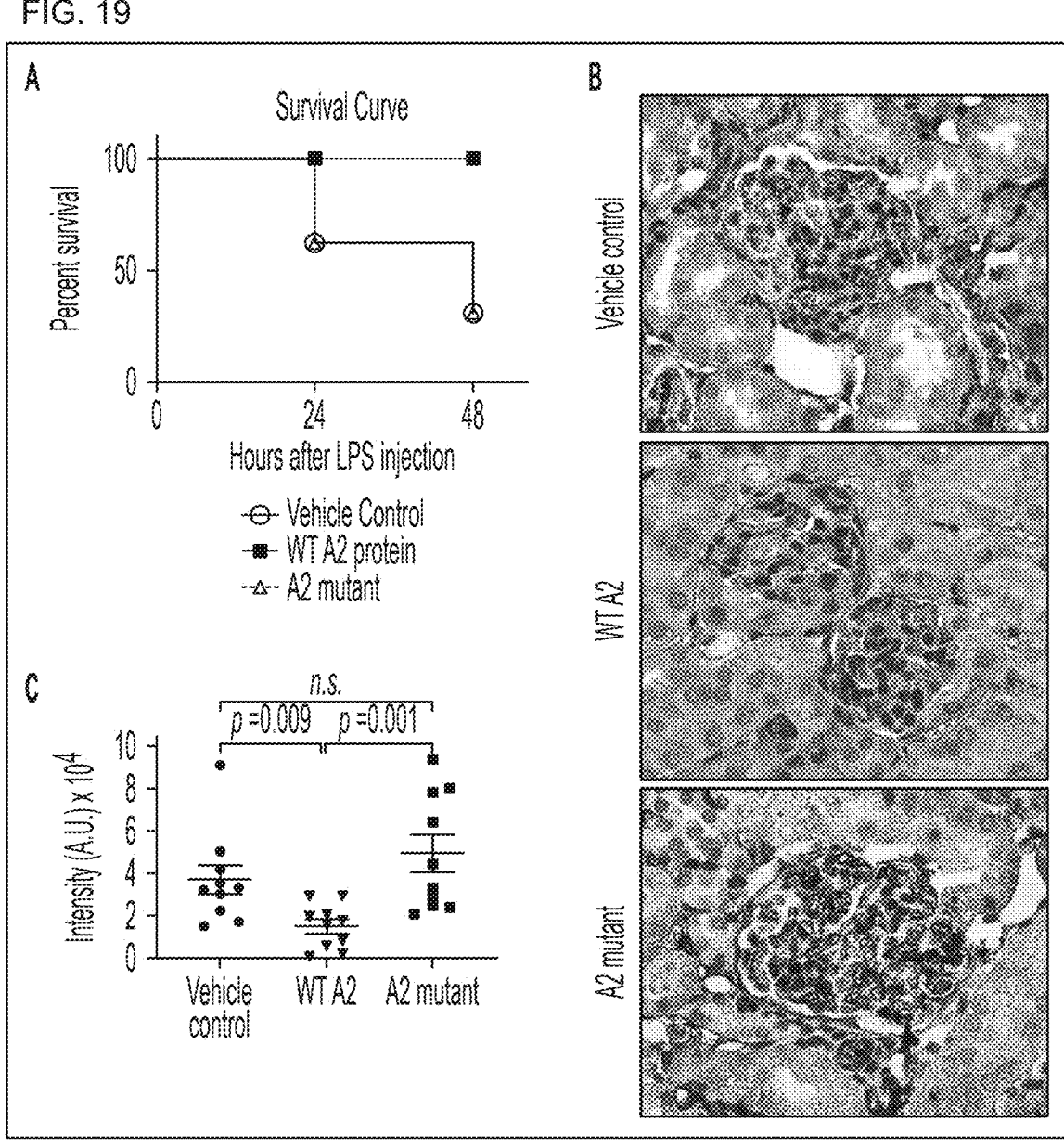
FIGS. 19A-19C. The A2 protein exerts its beneficial effect via fibrin in vivo.

The inventors next investigated whether the ability of the A2 protein to engage fibrin and induce structural changes in vitro translates to attenuation of microvascular thrombosis in an endotoxemic in vivo mouse model. As previously described,[13] the inventors treated the LPS-challenged mice with either saline, the WT A2 protein, or the A2 mutant (4.0 mg/kg), with diminished fibrin binding activity as negative control, 1.5 hours after the LPS insult. FIG. 19A shows that survival of LPS-challenged mice did improve with the WT A2 protein as compared with saline- or A2 mutant-treated mice. Moreover, in comparison with sick animals treated with saline or A2 mutant, the WT A2 protein was more effective in diminishing fibrin deposition in glomeruli, as shown in FIG. 19B-19C.

Figure 20:
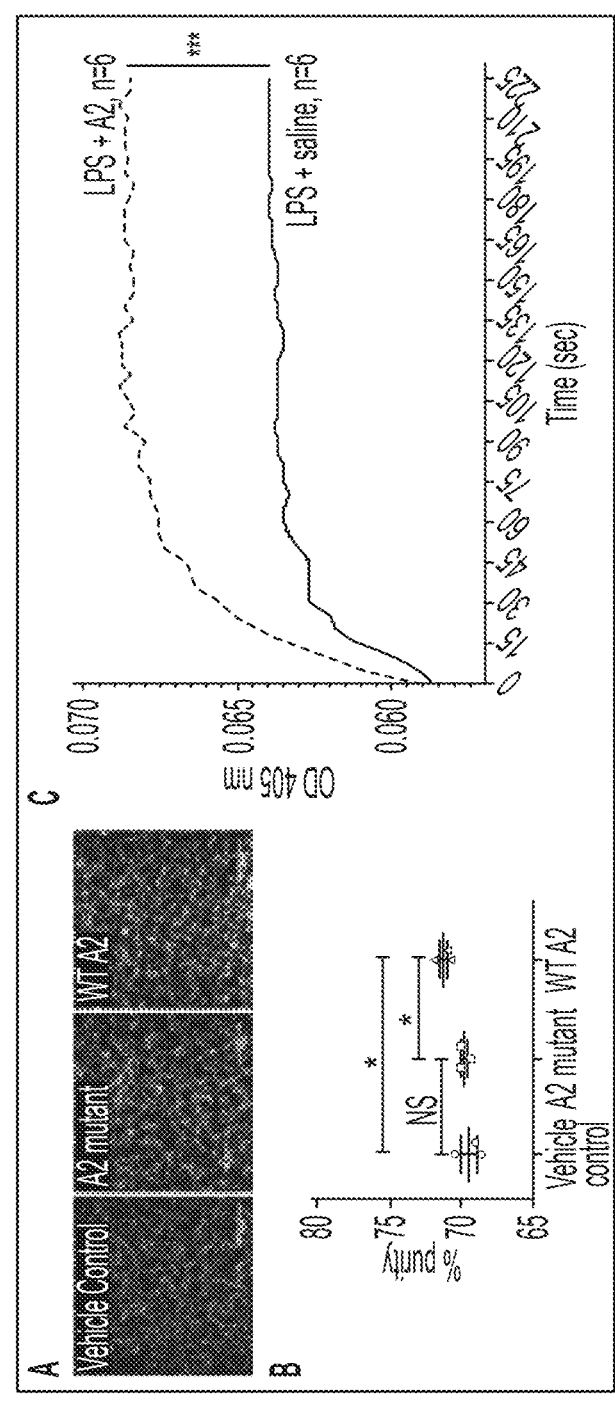
FIGS. 20A-20C. The A2 protein in endotoxemic mice modulated fibrin formation ex vivo.

Ex Vivo Assays Demonstrated an Increased Rate of Fibrin Formation in Plasma from Endotoxemic Mice Treated with the A2 Protein The inventors next analyzed the fibrin clot structure in plasma of endotoxemic mice. Because the A2 protein is found in circulation 2 hours after its injection in mice,[13] the inventors obtained plasma from LPS-treated mice 2 hours after treatment with saline (control) or A2 variants. The fibrin clot structure observed in plasma from a sick mouse that received the WT A2 protein was significantly different (larger pores) than that of saline or A2 mutant LPS-challenged mice (FIG. 20A-20B). These outcomes indicate that the engagement of the A2 protein with fibrin seems to be an important mechanism to attenuate microvascular thrombosis in the inventors' LPS-induced DIC murine model.

Next, the inventors examined if the A2 protein influences fibrin polymerization ex vivo using plasma from mice with (LPS) endotoxemia. Blood was drawn from the LPS-challenged mice 2 hours after the IP injection of either saline or the A2 protein (4.0 mg/kg). Plasma was obtained, and as described earlier, the inventors used the turbidity assay to assess fibrin polymerization. In comparison with mice with LPS and saline, fibrin formation was significantly potentiated in plasma from sick mice injected with the A2 protein, as shown in FIG. 20C. Moreover, the presence of the A2 protein markedly enhanced the rate of change (determined as above) in comparison with animals that received saline (slope, 29.7×10-5 vs 16.6×10-5, respectively). However, the time to reach maximum turbidity was similar in both groups (~95 seconds). Thus, the A2 protein increased the rate of fibrin polymerization in human blood in vitro (FIG. 16) and in endotoxemic murine blood ex vivo. These results suggest that the beneficial effect of the A2 protein in the inventors' mouse model for DIC is dependent on its ability to engage fibrin.

A2 Protein does not Interfere with Experimental Thrombosis

Several clinical trials have been conducted to attenuate the morbidity and mortality associated with sepsis-associated DIC without success, because the tested antithrombotic drugs can cause severe bleeding adverse effects.[33] Because the A2 protein did not affect the tail bleeding time in mice,[13] the inventors further examined the effect of the A2 protein in a murine thrombosis model by using intravital microscopy. At the dose tested in the inventors' LPS model, the A2 protein did not alter thrombus formation in vivo as compared with animals treated with control vehicle only (FIG. 28A). In parallel, the A2 protein added to whole blood from healthy human donors did not have a profound effect on platelet adhesion or thrombus formation on collagen-coated surfaces at high shear rates in vitro (FIG. 28B). These results imply that the A2 protein does not impair experimental thrombosis.

Significance of Certain Embodiments

Previously, the inventors reported the effectiveness of the recombinant A2 domain of VWF, the A2 protein, in attenuating microvascular thrombosis and improving survival in a murine model for LPS-induced DIC.[13] Although the inventors described the binding of the A2 protein to fibrin, the precise mechanism by which the A2 protein exerted its beneficial effect in vivo remained elusive. This is because besides fibrin, the A2 protein can bind to both the A1 domain of VWF and vimentin, 2 additional ligands that are involved in platelet adhesion and thrombus formation.[18,19,34] In this study, the inventors have examined the hypothesis that fibrin is the target for the A2 protein during systemic inflammation. Comparative analyses between the WT A2 protein and A2 (E1567A) mutant, which selectively inhibited the binding to fibrin but retained WT-binding activity for both the A1 domain and vimentin, validated that the A2 protein functions through the interaction with fibrin in vivo.

The A2 protein does not act as an anticoagulant, but rather, it directly increases the rate of fibrin polymerization and is incorporated into the formed fibrin network, causing larger pores in the fibrin network formed in plasma from different healthy human donors. Consistent with studies in healthy human plasma, the fibrin clot structure formed ex vivo in plasma derived from endotoxemic mice treated with the A2 protein also demonstrated increased porosity, compared with corresponding sick animals with mutant A2. It has been reported that changes in the architecture of the fibrin clot are associated with a high risk for thrombosis in certain diseases,[7,9,10,35-37] and several studies have indicated that an increase in fibrin network porosity facilitates fibrinolysis.[38-40] Such a potential mechanistic effect of the A2 protein is consistent with the observation that microvascular thrombosis as well as widespread fibrin deposition in kidneys was markedly reduced in the A2-treated endotoxemic sick mice. These outcomes and the increase in porosity within the fibrin network suggest that the A2 protein could also influence fibrinolysis. However, the absence of a significant effect of the A2 protein on fibrinolysis in the in vitro assays using healthy human plasma (FIG. 26) and the inconsistent results in the fibrinolysis assays using plasma from endotoxemic mice (not shown) preclude us from suggesting that the A2 protein may modulate fibrinolysis. Therefore, more studies are necessary to elucidate why the A2 protein effectively reduced fibrin deposition in an in vivo murine model for LPS-induced DIC, while altering fibrin polymerization but apparently not the fibrinolysis in ex vivo studies.

It has been published that fibrin thickness is dependent on a variety of parameters, including the rates of fibrinopeptide A cleavage, protofibril formation, and fiber initiation.[41] On the basis of the profiles in FIG. 16A, it can be argued that the action of the A2 protein occurs during the first step in fibrin formation, possibly altering the rate of fibrinopeptide A removal or lag phase, which was affected by the A2 protein at 2 different concentrations. Additionally, the effects of the A2 protein on the observed turbidity profiles and initial rates of change (slope) are consistent with A2 altering the rate of fiber growth as previously defined.[11] Thus, because the A2 protein preferably binds to fibrin monomer,[13] it is possible that the bound A2 protein increments the interactions between fibrin monomers that lead to the formation of protofibrils, thereby affecting the thickness and architecture of the resultant fibrin clot structure.[42] Note that the effect described in this study for the A2 protein using human plasma distinctly contrasts the inventors' previous report, in which the A2 protein delayed fibrin polymerization in a system containing only purified fibrinogen.[13] Future studies will be needed to address the underpinning mechanisms by which the A2 protein directly affects the structural features of the resultant fibrin network structure, particularly under systemic inflammation. Nevertheless, the inventors' studies in human and mice plasma provide evidence that the A2 protein accelerates fibrin polymerization and engages and interacts with the fibrin network to augment its porosity. Importantly, these structural changes in the fibrin network correlate with attenuated microvascular thrombosis in vivo.

The A2 protein was effective in diminishing fibrin deposition and fibrin-rich microthrombi formation (hallmarks of DIC) in the kidneys of mice with endotoxemia. To date, acute DIC is frequently managed with anticoagulants, but the use of these therapies increases the risk of bleeding; therefore, the ideal treatment for DIC should aim at reducing both the severity of bleeding and/or thrombosis without affecting hemostasis. As the inventors described, the A2 protein did not alter tail bleeding time in mice[13] or provoke excessive bleeding in endotoxemic mice, and it did not affect the occlusion time in a mouse model of thrombosis. These data provide evidence that the A2 protein could attenuate DIC associated with systemic inflammation, sepsis, or other conditions without causing increasing bleeding.

Another fascinating and clinically relevant result obtained from this study is the protective effect conferred by the A2 protein in attenuating both microvascular thrombosis and fibrin deposition. The inventors demonstrated the efficacy of the A2 protein but not the mutant A2 protein, when administrated 1.5 hours after the endotoxin insult in the inventors' LPS-induced DIC murine model.[13] Thus, the A2 protein demonstrated its pharmacological efficacy when the animals were already sick, modeling the typical presentation of systemic inflammation in patients who seek medical attention after the development of symptoms.

Normally, the A2 domain is buried within the globular morphology of the plasma VWF. However, this A2 domain can be found exposed when plasma VWF is unfolded by the influence of high hydrodynamic forces[43] and in newly released VWF molecules from the stimulated endothelium.[44] Previously, the inventors reported the effectiveness of the A2 protein in blocking the interaction of full-length VWF with fibrin.[13] However, the effects of the purified recombinant A2 protein in fibrin formation reported in this study do not necessarily reveal novel biological roles for the A2 domain in the context of intact full-length VWF. In addition, the A2 protein does not contain the posttranslational modifications of the native A2 domain in VWF.[45] Nevertheless, those novel concepts/mechanisms are also being investigated.

In summary, the A2 protein binds to fibrin and accelerates fibrin polymerization, altering the physical structure of the resultant polymerized fibrin clot. The A2 protein diminished fibrin deposition and microvascular thrombosis in kidneys in an animal model for systemic inflammation by targeting fibrin. Therefore, the A2 protein is a novel therapeutic approach in patients with uninhibited activated coagulation and disseminated fibrin deposition, as in DIC. Additional large animal and human studies are warranted to confirm the inventors' findings and further develop the A2 protein as a therapeutic agent.

REFERENCES FOR EXAMPLE 4
IMMEDIATELY ABOVE

1. Gando S, Levi M, Toh C H. Disseminated intravascular coagulation. Nat Rev Dis Primers. 2016; 2:16037.
2. Khemani R G, Bart R D, Alonzo T A, Hatzakis G, Hallam D, Newth C J. Disseminated intravascular coagulation score is associated with mortality for children with shock. Intensive Care Med. 2009; 35(2):327-333.
3. Dhainaut J F, Yan S B, Joyce D E, et al. Treatment effects of drotrecogin alfa (activated) in patients with severe sepsis with or without overt disseminated intravascular coagulation. J Thromb Haemost. 2004; 2(11):1924-1933.
4. Zeerleder S, Hack C E, Wuillemin W A. Disseminated intravascular coagulation in sepsis. Chest. 2005; 128(4): 2864-2875.
5. Kattula S, Byrnes J R, Wolberg A S. Fibrinogen and fibrin in hemostasis and thrombosis. Arterioscler Thromb Vasc Biol. 2017; 37(3):e13-e21.
6. Chandrashekar A, Singh G, Jonah G, Sikalas N, Labropoulos N. Mechanical and biochemical role of fibrin within a venous thrombus. Eur J Vasc Endovasc Surg. 2018; 55(3):417-424.
7. Jóźwik-Plebanek K, Prejbisz A, Wypasek E, et al. Altered plasma fibrin clot properties in hypertensive patients with obstructive sleep apnoea are improved by continuous positive airway pressure treatment. J Hypertens. 2017; 35(5):1035-1043.
8. Kearney K, Tomlinson D, Smith K, Ajjan R. Hypofibrinolysis in diabetes: a therapeutic target for the reduction of cardiovascular risk. Cardiovasc Diabetol. 2017; 16(1):34.
9. Lisman T, Ariens R A. Alterations in fibrin structure in patients with liver diseases. Semin Thromb Hemost. 2016; 42(4):389-396.
10. Cilia La Corte A L, Philippou H, Ariens R A. Role of fibrin structure in thrombosis and vascular disease. Adv Protein Chem Struct Biol. 2011; 83:75-127.
11. Abu-Fanne R, Stepanova V, Litvinov R I, et al. Neutrophil α-defensins promote thrombosis in vivo by altering fibrin formation, structure, and stability. Blood. 2019; 133(5):481-493.
12. Gabriel D A, Muga K, Boothroyd E M. The effect of fibrin structure on fibrinolysis. J Biol Chem. 1992; 267 (34):24259-24263.
13. Nguyen T C, Gushiken F, Correa J I, et al. A recombinant fragment of von Willebrand factor reduces fibrin-rich microthrombi formation in mice with endotoxemia. Thromb Res. 2015; 135(5):1025-1030.
14. Cruz M A, Whitelock J, Dong J F. Evaluation of ADAMTS-13 activity in plasma using recombinant von Willebrand Factor A2 domain polypeptide as substrate. Thromb Haemost. 2003; 90(6):1204-1209.
15. Auton M, Cruz M A, Moake J. Conformational stability and domain unfolding of the Von Willebrand factor A domains. J Mol Biol. 2007; 366(3):986-1000.
16. Auton M, Sowa K E, Smith S M, Sedlik E, Vijayan K V, Cruz M A. Destabilization of the A1 domain in von Willebrand factor dissociates the A1A2A3 tri-domain and provokes spontaneous binding to glycoprotein Ibalpha and platelet activation under shear stress. J Biol Chem. 2010; 285(30):22831-22839.
17. Hook P, Brito-Robinson T, Kim O, et al. Whole blood clot optical clearing for nondestructive 3D imaging and quantitative analysis. Biomed Opt Express. 2017; 8(8): 3671-3686.
18. Da Q, Behymer M, Correa J I, Vijayan K V, Cruz M A. Platelet adhesion involves a novel interaction between vimentin and von Willebrand factor under high shear stress. Blood. 2014; 123(17):2715-2721.
19. Martin C, Morales L D, Cruz M A. Purified A2 domain of von Willebrand factor binds to the active conformation of von Willebrand factor and blocks the interaction with platelet glycoprotein Ibalpha. J Thromb Haemost. 2007; 5(7):1363-1370.
20. Cushman I, Palzkill T, Moore M S. Using peptide arrays to define nuclear carrier binding sites on nucleoporins. Methods. 2006; 39(4):329-341.
21. Frank R. The SPOT-synthesis technique. Synthetic peptide arrays on membrane supports—principles and applications. J Immunol Methods. 2002; 267(1):13-26.
22. Cushman I. Utilizing peptide SPOT arrays to identify protein interactions. Curr Protoc Protein Sci. 2008; Chapter 18:Unit 18.10.
23. Patel K N, Soubra S H, Lam F W, Rodriguez M A, Rumbaut R E. Polymicrobial sepsis and endotoxemia promote microvascular thrombosis via distinct mechanisms. J Thromb Haemost. 2010; 8(6):1403-1409.
24. Rumbaut R E, Bellera R V, Randhawa J K, et al. Endotoxin enhances microvascular thrombosis in mouse cremaster venules via a TLR4-dependent, neutrophil-independent mechanism. Am J Physiol Heart Circ Physiol. 2006; 290(4):H1671-H1679.
25. Zhang Q, Zhou Y F, Zhang C Z, Zhang X, Lu C, Springer T A. Structural specializations of A2, a force-sensing domain in the ultralarge vascular protein von Willebrand factor. Proc Natl Acad Sci USA. 2009; 106(23):9226-9231.
26. Pieters M, Philippou H, Undas A, de Lange Z, Rijken D C, Mutch N J; Subcommittee on Factor XIII and Fibrinogen, and the Subcommittee on Fibrinolysis. An international study on the feasibility of a standardized combined plasma clot turbidity and lysis assay: communication from the SSC of the ISTH. J Thromb Haemost. 2018; 16(5):1007-1012.
27. Amelot A A, Tagzirt M, Ducouret G, Kuen R L, Le Bonniec B F. Platelet factor 4 (CXCL4) seals blood clots by altering the structure of fibrin. J Biol Chem. 2007; 282(1):710-720.
28. Wu Y P, Bloemendal H J, Voest E E, et al. Fibrin-incorporated vitronectin is involved in platelet adhesion and thrombus formation through homotypic interactions with platelet-associated vitronectin. Blood. 2004; 104(4): 1034-1041.
29. Miszta A, Pelkmans L, Lindhout T, et al. Thrombin-dependent Incorporation of von Willebrand Factor into a Fibrin Network. J Biol Chem. 2014; 289(52):35979-35986.
30. Ryan E A, Mockros L F, Weisel J W, Lorand L. Structural origins of fibrin clot rheology. Biophys J. 1999; 77(5): 2813-2826.
31. Gersh K C, Nagaswami C, Weisel J W. Fibrin network structure and clot mechanical properties are altered by incorporation of erythrocytes. Thromb Haemost. 2009; 102(6):1169-1175.
32. Ostrowski S R, Berg R M G, Windelov N A, et al. Discrepant fibrinolytic response in plasma and whole blood during experimental endotoxemia in healthy volunteers. PLoS One. 2013; 8(3):e59368.
33. Thachil J, Toh C H, Levi M, Watson H G. The withdrawal of activated protein C from the use in patients with severe sepsis and DIC [amendment to the BCSH guideline on disseminated intravascular coagulation]. Br J Haematol. 2012; 157(4):493-494.

34. Fasipe T A, Hong S H, Da Q, et al. Extracellular vimentin/VWF (von Willebrand factor) interaction contributes to VWF string formation and stroke pathology. Stroke. 2018; 49(10):2536-2540.

35. Wang X, Friis T E, Masci P P, Crawford R W, Liao W, Xiao Y. Alteration of blood clot structures by interleukin-1 beta in association with bone defects healing. Sci Rep. 2016; 6:35645.

36. Neergaard-Petersen S, Hvas A M, Kristensen S D, et al. The influence of type 2 diabetes on fibrin clot properties in patients with coronary artery disease. Thromb Haemost. 2014; 112(6):1142-1150.

37. Lord S T. Molecular mechanisms affecting fibrin structure and stability. Arterioscler Thromb Vasc Biol. 2011; 31(3):494-499.

38. Marchi R, Rojas H. Effect of von Willebrand factor on clot structure and lysis. Blood Coagul Fibrinolysis. 2015; 26(5):533-536.

39. Colle J P, Mishal Z, Lesty C, et al. Abnormal fibrin clot architecture in nephrotic patients is related to hypofibrinolysis: influence of plasma biochemical modifications: a possible mechanism for the high thrombotic tendency? Thromb Haemost. 1999; 82(5):1482-1489.

40. He S, Blomback M, Bark N, Johnsson H, WallLn N H. The direct thrombin inhibitors (argatroban, bivalirudin and lepirudin) and the indirect Xa-inhibitor (danaparoid) increase fibrin network porosity and thus facilitate fibrinolysis. Thromb Haemost. 2010; 103(5):1076-1084.

41. Weisel J W, Nagaswami C. Computer modeling of fibrin polymerization kinetics correlated with electron microscope and turbidity observations: clot structure and assembly are kinetically controlled. Biophys J. 1992; 63(1):111-128.

42. Wolberg A S, Gabriel D A, Hoffman M. Analyzing fibrin clot structure using a microplate reader. Blood Coagul Fibrinolysis. 2002; 13(6):533-539.

43. Fu X, Chen J, Gallagher R, Zheng Y, Chung D W, López J A. Shear stress-induced unfolding of VWF accelerates oxidation of key methionine residues in the A1A2A3 region. Blood. 2011; 118(19):5283-5291.

44. Dong J F, Moake J L, Nolasco L, et al. ADAMTS-13 rapidly cleaves newly secreted ultralarge von Willebrand factor multimers on the endothelial surface under flowing conditions. Blood. 2002; 100(12):4033-4039.

45. McKinnon T A, Chion A C, Millington A J, Lane D A, Laffan M A. N-linked glycosylation of VWF modulates its interaction with ADAMTS13. Blood. 2008; 111(6): 3042-3049.

Example 5

Biolayer Interferometry (BLI) with Immobilized Sars-CoV-2 S on Ar2G Biosensors

Binding kinetics between immobilized recombinant SARS-CoV-2 spike protein (S) and rhRod was performed using biolayer interferometry (BLI). First, SARS-CoV-2 spike protein was immobilized on amine reactive second generation biosensors. The sensors underwent regeneration (cleaning), and were then used to measure the binding affinity of immobilized S to rhRod and/or the A2 domain. The rhRod was mixed in solution with increasing concentrations (0-2,000 nM) of the A2 domain. Biosensors underwent regeneration between analyses.

Referring to FIG. 29, the top trace corresponding to a solution with no A2 domain and rhRod demonstrates robust binding of the SARS-CoV-2 spike protein in the absence of the A2 domain. The traces corresponding to 125-2000 nM A2 demonstrate that addition of the A2 domain reduces binding of the SARS-CoV-2 spike protein by rhRod, which indicates that the A2 domain is inhibiting the interaction between the SARS-CoV-2 spike protein and rhRod in a dose dependent manner. The bottom traces corresponding to a solution with A2 domain and no rhRod demonstrates that the A2 domain, alone, does not interact with the SARS-CoV-2 spike protein.

REFERENCES FOR DISCLOSURE RELATED
TO CORONAVIRUS, INCLUDING EXAMPLE 5,
IMMEDIATELY ABOVE

1. Wang Q, Zhang Y, Wu L, Niu S, Song C, Zhang Z, Lu G, Qiao C, Hu Y, Yuen K Y, Wang Q, Zhou H, Yan J, Qi J. Structural and Functional Basis of SARS-CoV-2 Entry by Using Human ACE2. Cell. 2020. doi: 10.1016/j.cell.2020.03.045. PubMed PMID: 32275855; PMCID: PMC7144619.

2. Yan R, Zhang Y, Li Y, Xia L, Guo Y, Zhou Q. Structural basis for the recognition of SARS-CoV-2 by fill-length human ACE2. Science. 2020; 367(6485):1444-8. doi: 10.1126/science.abb2762. PubMed PMID: 32132184.

3. Ou X, Liu Y, Lei X, Li P, Mi D, Ren L, Guo L, Guo R, Chen T, Hu J, Xiang Z, Mu Z, Chen X, Chen J, Hu K, Jin Q, Wang J, Qian Z. Characterization of spike glycoprotein of SARS-CoV-2 on virus entry and its immune cross-reactivity with SARS-CoV. Nat Commun. 2020; 11(1): 1620. doi: 10.1038/s41467-020-15562-9. PubMed PMID: 32221306; PMCID: PMC7100515.

4. Yu Y T, Chien S C, Chen I Y, Lai C T, Tsay Y G, Chang S C, Chang M F. Surface vimentin is critical for the cell entry of SARS-CoV. J Biomed Sci. 2016; 23:14. doi: 10.1186/s12929-016-0234-7. PubMed PMID: 26801988; PMCID: PMC4724099.

5. Lam F W, Da Q, Guillory B, Cruz M A. Recombinant Human Vimentin Binds to P-Selectin and Blocks Neutrophil Capture and Rolling on Platelets and Endothelium. J Immunol. 2018; 200(5):1718-26. doi: 10.4049/jimmunol.1700784. PubMed PMID: 29335256; PMCID: PMC5821592.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of reducing the occurrence, alleviating symptoms, and/or lowering rate of disease progression of a coronavirus infection in an individual, comprising the step of delivering to the individual in need thereof a therapeutically effective amount of a composition comprising an A2 domain of von Willebrand factor, wherein the A2 domain of von Willebrand factor comprises the sequence of SEQ ID NO: 1.

2. The method of claim 1, wherein the coronavirus infection comprises severe acute respiratory syndrome-associated coronavirus 2 (SARS-CoV-2) infection.

3. The method of claim 1, wherein the individual has severe acute respiratory syndrome (SARS), coronavirus disease 2019 (COVID-19), or a respiratory infection.

4. The method of claim 1, wherein the individual has a fever, a cough, shortness of breath, difficulty breathing, tiredness, aches, chills, a sore throat, loss of smell, loss of taste, a headache, diarrhea, vomiting, pneumonia, acute respiratory distress syndrome, organ failure, respiratory failure, a heart condition, acute kidney injury, a viral infection, a bacterial infection, or a combination thereof.

5. The method of claim 1, wherein the individual has dysregulated activated coagulation or is at risk for having dysregulated activated coagulation.

6. The method of claim 1, wherein the A2 domain interacts directly with a coronavirus.

7. The method of claim 6, wherein the interaction prevents infiltration of a coronavirus into a cell of the individual.

8. The method of claim 1, wherein the method further comprises administering an effective amount of a second therapy for the coronavirus infection.

9. The method of claim 8, wherein the second therapy comprises an antibiotic, an antiviral, convalescent serum, an immune modulator, an anticoagulant, a fluid, oxygen, a corticosteroid, an antibody, GSnP-6, sialyl Lewis X analog, an anti-proliferative, a calcineurin inhibitor, an anti-signaling compound, or a combination thereof.

10. The method of claim 8, wherein the second therapy comprises an anti-SARS-CoV-2 drug.

11. The method of claim 10, wherein the anti-SARS-CoV-2 drug is selected from the group consisting of azithromycin, AC-55541, apicidin, AZ3451, AZ8838, bafilomycin-A1, CCT 365623, daunorubicin, E-52862, entacapone, GB110, H-89, haloperidol, indomethacin, JQ1, loratadine, merimepodib, metformin, midostaurin, migalastat, mycophenolic-acid, PB28, PD-144418, ponatinib, ribavirin, RS-PPCC, ruxolitinib, RVX-208, S-verapamil, silmitasertib, 4,5,6,7-tetrabromo-2-(dimethylamino)-1H-benzimidazole-1-acetic acid (TMCB), UCPH-101, valproic acid, XL413, ZINC1775962367, ZINC4326719, ZINC4511851, ZINC95559591, 4E2RCat, ABBV-744, camostat, captopril, CB5083, chloramphenicol, chloroquine, hydroxychloroquine, CPI-0610, dabrafenib, DBeQ, dBET6, IHVR-19029, linezolid, lisinopril, minoxidil, ML240, MZ1, nafamostat, pevonedistat, PS3061, rapamycin, sanglifehrin A, sapanisertib, FK-506, ternatin 4, tigecycline, tomivosertib, verdinexor, WDB002, zotatifin, and a combination thereof.

12. The method of claim 1, wherein the method further comprises testing for the coronavirus infection.

13. The method of claim 1, wherein the delivery of the composition is intravenous, intradermal, transdermal, intrathecal, intraarterial, intraperitoneal, intranasal, intravaginal, intrarectal, topical, intramuscular, subcutaneous, mucosal, oral, and/or local.

14. The method of claim 1, wherein the delivery of the composition to the individual occurs multiple times.

15. The method of claim 14, wherein the delivery of the composition to the individual occurs once a day, more than once a day, more than once a week, more than once a month, or more than once a year.

16. The method of claim 1, wherein the delivery is by constant infusion.

17. The method of claim 6, wherein the A2 domain interacts directly with the rod domain of vimentin.

18. The method of claim 1, wherein delivery of the composition is by inhalation, by injection, by infusion, via catheter, via lavage, or a combination thereof.

19. The method of claim 1, further comprising the step of delivering to the individual in need thereof a therapeutically effective amount of a composition comprising one or more polypeptides comprising the sequence selected from the group consisting of SEQ ID NOs: 2-18, and a combination thereof.

\* \* \* \* \*

SEQUENCE LISTING

<160> NUMBER OF SEQ ID NOS: 20

<210> SEQ ID NO 1
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Leu Leu Gly Val Ser Thr Leu Gly Pro Lys Arg Asn Ser Met Val
1               5                   10                  15

Leu Asp Val Ala Phe Val Leu Glu Gly Ser Asp Lys Ile Gly Glu Ala
            20                  25                  30

Asp Phe Asn Arg Ser Lys Glu Phe Met Glu Glu Val Ile Gln Arg Met
        35                  40                  45

Asp Val Gly Gln Asp Ser Ile His Val Thr Val Leu Gln Tyr Ser Tyr
    50                  55                  60

Met Val Thr Val Glu Tyr Pro Phe Ser Glu Ala Gln Ser Lys Gly Asp
65                  70                  75                  80

Ile Leu Gln Arg Val Arg Glu Ile Arg Tyr Gln Gly Gly Asn Arg Thr
                85                  90                  95

Asn Thr Gly Leu Ala Leu Arg Tyr Leu Ser Asp His Ser Phe Leu Val
            100                 105                 110

Ser Gln Gly Asp Arg Glu Gln Ala Pro Asn Leu Val Tyr Met Val Thr
        115                 120                 125

Gly Asn Pro Ala Ser Asp Glu Ile Lys Arg Leu Pro Gly Asp Ile Gln
    130                 135                 140

Val Val Pro Ile Gly Val Gly Pro Asn Ala Asn Val Gln Glu Leu Glu
145                 150                 155                 160

Arg Ile Gly Trp Pro Asn Ala Pro Ile Leu Ile Gln Asp Phe Glu Thr
                165                 170                 175

Leu Pro Arg Glu Ala Pro Asp Leu Val Leu Gln Arg
            180                 185

<210> SEQ ID NO 2
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Leu Leu Gly Val Ser Thr Leu Gly Pro Lys Arg Asn Ser Met Val
1               5                   10                  15

Leu Asp Val Ala Phe Val Leu Glu Gly Ser Asp Lys Ile Gly Glu Ala
            20                  25                  30

Asp Phe Asn Arg Ser Lys Glu Phe Met Glu Glu Val Ile Gln Arg Met
        35                  40                  45

Asp Val Gly Gln Asp Ser Ile His Val Thr Val Leu Gln Tyr Ser Tyr
    50                  55                  60

Met Val Thr Val Glu Tyr Pro Phe Ser Glu Ala Gln Ser Lys Gly Asp
65                  70                  75                  80

Ile Leu Gln Arg Val Arg Glu Ile Arg Tyr Gln Gly Gly Asn Arg Thr
                85                  90                  95

Asn Thr Gly Leu Ala Leu Arg Tyr Leu Ser Asp His Ser Phe Leu Val

```
                100                 105                 110
Ser Gln Gly Asp Arg Glu Gln Ala Pro Asn Leu Val Tyr
        115                 120                 125

<210> SEQ ID NO 3
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Val Thr Gly Asn Pro Ala Ser Asp Glu Ile Lys Arg Leu Pro Gly
1               5                  10                  15

Asp Ile Gln Val Val Pro Ile Gly Val Gly Pro Asn Ala Asn Val Gln
            20                  25                  30

Glu Leu Glu Arg Ile Gly Trp Pro Asn Ala Pro Ile Leu Ile Gln Asp
        35                  40                  45

Phe Glu Thr Leu Pro Arg Glu Ala Pro Asp Leu Val Leu Gln Arg
    50                  55                  60

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Leu Leu Gly Val Ser Thr Leu Gly Pro Lys Arg Asn Ser Met
1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Ser Met Val Leu Asp Val Ala Phe Val Leu Glu Gly Ser Asp
1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Asp Lys Ile Gly Glu Ala Asp Phe Asn Arg Ser Lys Glu
1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Ser Lys Glu Phe Met Glu Glu Val Ile Gln Arg Met Asp Val Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Val Gly Gln Asp Ser Ile His Val Thr Val Leu Gln Tyr Ser
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Tyr Ser Tyr Met Val Thr Val Glu Tyr Pro Phe Ser Glu Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Glu Ala Gln Ser Lys Gly Asp Ile Leu Gln Arg Val Arg Glu
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Arg Glu Ile Arg Tyr Gln Gly Gly Asn Arg Thr Asn Thr Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Thr Gly Leu Ala Leu Arg Tyr Leu Ser Asp His Ser Phe Leu
1               5                   10                  15

<210> SEQ ID NO 13
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Ser Phe Leu Val Ser Gln Gly Asp Arg Glu Gln Ala Pro Asn Leu Val
1               5                   10                  15

Tyr

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Lys Gly Asp Ile Leu Gln Arg Val Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Leu Gln Arg Val Arg Glu Ile Arg Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Arg Glu Ile Arg Tyr Gln Gly Gly Asn
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Gly Glu Ala Asp Phe Asn Arg Ser Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

-continued

```
His Val Thr Val Leu Gln Tyr Ser Tyr Met
1               5                   10

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcagcgggtg cgagcgatcc gctaccagg                                      29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctggtagcg gatcgctcgc acccgctgc                                      29
```